United States Patent [19]
Gee et al.

[11] Patent Number: 5,869,258
[45] Date of Patent: Feb. 9, 1999

[54] DETECTION SYSTEM FOR MUTAGENS THAT IDENTIFIES MUTAGENIC CHANGES

[75] Inventors: Pauline Gee, Berkeley; Dorothy M. Maron, Orinda; Bruce N. Ames, Berkeley, all of Calif.

[73] Assignee: The Regents of the University of California, Oakland, Calif.

[21] Appl. No.: 865,348

[22] Filed: May 28, 1997

Related U.S. Application Data

[63] Continuation of Ser. No. 137,627, Oct. 15, 1993, Pat. No. 5,681,737.
[51] Int. Cl.$^6$ .............................. C12Q 1/68; C12Q 1/02; C12N 1/21
[52] U.S. Cl. ............................ 435/6; 435/29; 435/252.3; 435/252.8
[58] Field of Search .............................. 435/252.3, 252.8, 435/29, 6

[56] References Cited

U.S. PATENT DOCUMENTS

| | | | |
|---|---|---|---|
| 4,072,574 | 2/1978 | Loeb et al. | 435/6 |
| 4,302,535 | 11/1981 | Skopek et al. | 435/6 |
| 4,345,026 | 8/1982 | Lew | 435/4 |
| 4,359,535 | 11/1982 | Pieczenik | 435/320.1 |
| 4,469,786 | 9/1984 | Garro et al. | 435/5 |
| 4,532,220 | 7/1985 | Lavi | 436/501 |
| 4,792,520 | 12/1988 | Stambrook et al. | 435/6 |

FOREIGN PATENT DOCUMENTS

US94/11617  10/1994  WIPO.

OTHER PUBLICATIONS

Levin et al, Environmental Mutagenesis, vol. 8: pp. 9–28 (1986).
Agnese, et al., "Statistical evaluation of inter–and intra–laboratory variations of the Ames test, as related to the genetic stability of Salmonella tester strains," Mutation Research 130:27–44 (1984).
Artz, et al., "Use of M13mp phages to study gene regulation, structure and function: cloning and recombinational analysis of genes of the *Salmonella typhimurium* histidine operon," Gene 26:147–158 (1983).
Blum, et al., "Gene Replacement and Retrieval with Recombinant M13mp Bacteriophages," *J. Bacteriol.* 171:538–546 (1989).
Bowie, et al., "Deciphering The Message In Protein Sequences: Tolerance To Amino Acid Substitutions," *Science*, 247:1306–1310 (1990).
Brzovic, et al., "Substitution of Glutamic Acid 109 by Aspartic Acid Alters the Substrate Specifically and Catalytic Activity of the Beta–Subunit in the Tryptophan Synthase Bienzyme Complex from *Salmonella typhimurium*," *Biochemistry* 31(4):1180–1190 (1992).
Buckingham, "Codon context," *Experientia* 46:1126–1133 (1990).

Carlomagno et al., "Structure and Function of the *Salmonella typhimurium* and *Escherichia coli* K–12 Histidine Operons," *J. Mol. Biol.* 203:585–606 (1988).
Carlomagno, et al., Gene Organization in the Distal Part of the *Salmonella typhimurium* Histidine Operon and Determination and Sequence of the Operon Transcription Terminator, Mol. Gen. Genet. 191:413–420 (1983).
Claxton, et al., "Assessing the use of known mutagens to calibrate the *Salmonella typhimurium* mutagenicity assay: I. Without exogenous activation," *Mutation Research* 253:137–147 (1991).
Claxton, et al., "Assessing the use of known mutagens to calibrate the *Salmonella typhimurium* mutagenicity assay: II. With exogenous activation," *Mutation Research* 253:149–159 (1991).
Cupples, et al., "A set of lacZ mutations in *Escherichia coli* that allow rapid detection of each of the six base substitutions," *Proc. Natl. Acad. Sci. USA* 86:5345–5349 (1989).
Freifelder, *Molecular Biology*, Jones and Bartlett Pub., Boston, pp. 347, 438–439, 456 and 467 (1983).
Hampsey, "A Tester System for Detecting Each of the Six Base–Pair Substitutions in *Saccharomyces cerevisiae* by Selecting for an Essential Cysteine in Iso–1–Cytochrome c," Genetics 128:59–67 (1991).
Haroun, et al., "Mutagenicity of Selected Chemicals in the Salmonella/Microsome Mutagenicity Test," *Comparative Chemical Mutagenesis*, Chapter 4, F.J. deSerres and M.C. Shelby eds., Plenum Press, N.Y., pp. 27–68 (1977).
Hartman, et al., "Classification and Mapping of Spontaneous and Induced Mutations in the Histidine operon of Salmonella," *Adv. Genetics* 16:1–34 (1971).
Hartman, et al., "Target sequences for mutagenesis in Salmonella histidine–requiring mutants," *Environmental Mutagenesis* 8:631–641 (1986).
Kiss, et al., "Characterization of *Pseudomonas aeruginosa* Isolated from Drinking Water by Serogrouping, Phage Sensitivity and Pyocin Pattern," *Acta Microbiol Hungary* 32(1):99–106 (1985).
Kramer, et al., "Mechanisms of mutagenicity and toxicity of sodium selenite ($Na_2SeO_3$) in *Salmonella typhimurium*," *Mutation Research* 201:169–180 (1988).
Kunkel, et al., "Rapid and Efficient Site–Specific Mutagenesis without Phenotypic Selection," *Methods in Enzymology* 154:367–382 (1987).

(List continued on next page.)

*Primary Examiner*—Terry A. McKelvey
*Attorney, Agent, or Firm*—Karen S. Smith; Mart T. Kresnak; Flehr Hohbach Test Albritton & Herbert LLP

[57] ABSTRACT

Six sets of *Salmonella typhimurium* strains are provided, all strains having low spontaneous mutation rates, and each set being sensitive to and diagnostic of one of the six possible base substitutions in DNA. Also provided are methods for making and using these *S. typhimurium* strains to detect, and establish the type of specific base substitution mutation induced by, mutagenic agents.

9 Claims, 16 Drawing Sheets

OTHER PUBLICATIONS

Lim, et al., "A model for interacting codon–antiocodon duplexes located at the ribosomal A–and P–sites," *FEBS Letters* 313:133–137 (1992).

Maldonado–Rodriques, et al., "Influence of neighboring base sequence on mutagenesis induced by in vitro misincorporation in the lacI gene of *Escherichia coli,*" *Mutation Research* 251:217–226 (1991).

Marnett, et al., "Naturally occurring carbonyl compounds are mutagens in *Salmonella* tester strain TA104," *Mutation Research* 148:25–34 (1985).

Maron, et al., "Revised methods for the Salmonella mutagenicity test," *Mutation Research* 113:173–215 (1983).

McCann, et al., "Detection of Carcinogens as Mutagens; Bacterial Tester Strains with R Factor Plasmids," *Proc. Natl. Acad. Sci. USA* 72:979–983 (1975).

Mehta, et al., "Evolutionary relationships among aminotransferases: Tyrosine aminotransferase, histidinol–phosphate aminotransferase, and aspartate aminotransferase and homologous proteins," *Eur. J. Biochem.* 186:249–253 (1989).

Murgola, et al., "Codon Context Effects in Missense Suppression," *J. Mol. Biol.* 175:19–27 (1984).

Oeschger, et al., "ICR–Induced Frameshift Mutations in the Histidine Operon of *Salmonella,*" *J. Bacteriol.* 101:490–504 (1970).

Pages, et al., "Suppression of a double missense mutation by a mutant tRNA$^{Phe}$ in *Escherichia coli,*" *Nucl. Acids Res.* 19:867–869 (1991).

Paigen, et al., "A New Method of Screening for Inherited Disorders of Galactose Metabolism," *J. Lab. Clin. Med.* 99(6):895–907 (1982).

Rick, "Lipopolysaccharide Biosynthesis," *Escherichia coli* and *Salmonella typhimurium, Cellular and Molecular Biology,* pp. 648–662 (1987).

Saiki, et al., "Primer–Directed Enzymatic Amplification of DNA with a Thermostable DNA Polymerase," *Science* 239:487–491 (1988).

Sanderson, et al., "Influence of Lipopolysaccharide and Protein in the Cell Envelope on Recipient Capacity in Conjunction of *Salmonella typhimurium,*" *J. Bacteriol.* 148:283–293 (1981).

Sanderson, et al., "*Salmonella typhimurium* Strains Used in Genetic Analysis," *Escherichia coli* and *Salmonella Typhimurium, Cellular and Molecular Biology,* Frederick C. Neidhardt, ed., Washington DC: *Amer. Soc. Microbiol* (1987), Selected unnumbered pages.

Sandlin, et al., "Role of Phosphoglucomutase in Lippoligosaccharide Biosynthesis in *Neisseria gonorrhoeae,*" *J. Bacteriol.* 176(8):2930–2937 (1994).

Schaff, et al., "Mouse transgenes in human cells detect specific base substitutions," *Proc. Natl. Acad. Sci. USA* 87:8675–8679 (1990).

Śedziewska–Gójska, et al., "Mutagenesis of *Escherichia coli:* a method for determining mutagenic specificity by analysis of tRNA suppressors," *Mutagenesis* 7:41–46 (1992).

Sorenson, et al., "Absolue in Vivo Translation Rates of Individual Codons in *Escherichia coli,* The Two Glutamic Acid Codons GAA and GAG are Translated with a Threefold Difference in Rate," *J. Mol. Biol.* 222:265–280 (1991).

Wilkinson, et al., "Non–smooth Mutants of *Salmonella typhimurium:*Differentiation by Phage Sensitivity and Genetic Mapping," *J. Gen. Microbiol.* 70:527–532 and 537 (1972).

Gee, et al., "Detection and Classification of Mutagens: A Set of Base–Specific Salmonella Tester Strains," *Proc. Natl. Acad. Sci.,* 91(24):11606–11610 (1994).

FIG._1

| | | |
|---|---|---|
| | | FIG._1A |
| | | FIG._1B |

```
ATG TTA GAC AAC ACC CGC TTA CGC ATA GCT ATT CAG AAA TCA GGC CGT        48
Met Leu Asp Asn Thr Arg Leu Arg Ile Ala Ile Gln Lys Ser Gly Arg
 1               5                  10                  15

TTA AGC GAT GAT TCA CGA GAA TTG CTG GCC CGC TGC GGC ATA AAA ATT        96
Leu Ser Asp Asp Ser Arg Glu Leu Leu Ala Arg Cys Gly Ile Lys Ile
            20                  25                  30

AAT TTA CAC ACT CAG CGC CTG ATT GCG ATG GCG GAA AAC ATG CCG ATT       144
Asn Leu His Thr Gln Arg Leu Ile Ala Met Ala Glu Asn Met Pro Ile
        35                  40                  45

GAT ATC CTG CGC GTG CGT GAT GAT GAC ATT CCG GGT CTG GTA ATG GAT       192
Asp Ile Leu Arg Val Arg Asp Asp Asp Ile Pro Gly Leu Val Met Asp
    50                  55                  60

GGC GTG GTC GAT CTC GGT ATT ATC GGC GAA AAC GTG CTG GAA GAA GAG       240
Gly Val Val Asp Leu Gly Ile Ile Gly Glu Asn Val Leu Glu Glu Glu
65                  70                  75                  80

CTA CTC AAC CGC CGC GCA CAG GGC GAA GAT CCA CGC TAT TTA ACC CTG       288
Leu Leu Asn Arg Arg Ala Gln Gly Glu Asp Pro Arg Tyr Leu Thr Leu
                85                  90                  95

CGC CGT CTT GAC TTC GGC GGC TGC CGT TTA TCG CTG GCA ACA CCG GTT       336
Arg Arg Leu Asp Phe Gly Gly Cys Arg Leu Ser Leu Ala Thr Pro Val
            100                 105                 110

GAC GAA GCC TGG GAC GGC CCG GCC GCG CTG GAC GGT AAA CGT ATC GCT       384
Asp Glu Ala Trp Asp Gly Pro Ala Ala Leu Asp Gly Lys Arg Ile Ala
        115                 120                 125

ACC TCA TAT CCG CAC CTC CTC AAA CGC TAC CTC GAC CAG AAA GGC GTC       432
Thr Ser Tyr Pro His Leu Leu Lys Arg Tyr Leu Asp Gln Lys Gly Val
    130                 135                 140
```

FIG._1A

```
TCT TTT AAA TCG TGT CTG TTA AAT GGT TCT GTC GAA GTC GCG CCG CGC          480
Ser Phe Lys Ser Cys Leu Leu Asn Gly Ser Val Glu Val Ala Pro Arg
145                 150                 155                 160

GCG GGG CTG GCC GAC GCT ATC TGC GAT TTG GTC TCT ACC GGC GCG ACG          528
Ala Gly Leu Ala Asp Ala Ile Cys Asp Leu Val Ser Thr Gly Ala Thr
                165                 170                 175

CTT GAA GCT AAC GGC CTG CGT GAA GTC GAA GTT ATC TAC CGC TCT AAA          576
Leu Glu Ala Asn Gly Leu Arg Glu Val Glu Val Ile Tyr Arg Ser Lys
            180                 185                 190

GCC TGT CTG ATT CAG CGC GAC GGT GAG ATG GCA CAG AGC AAG CAA GAG          624
Ala Cys Leu Ile Gln Arg Asp Gly Glu Met Ala Gln Ser Lys Gln Glu
        195                 200                 205

CTG ATC GAT AAA TTG CTG ACC CGT ATT CAG GGC GTG ATT CAG GCG CGC          672
Leu Ile Asp Lys Leu Leu Thr Arg Ile Gln Gly Val Ile Gln Ala Arg
    210                 215                 220

GAA TCG AAA TAC ATC ATG ATG CAC GCG CCA AGT GAA CGC CTG GAA GAG          720
Glu Ser Lys Tyr Ile Met Met His Ala Pro Ser Glu Arg Leu Glu Glu
225                 230                 235                 240

GTT ATC GCC CTG CTG CCA GGC GCC GAA AGG CCG ACA ATT CTG CCG CTG          768
Val Ile Ala Leu Leu Pro Gly Ala Glu Arg Pro Thr Ile Leu Pro Leu
                245                 250                 255

GCA GGC GAG CAA CAG CGC GTG GCG ATG CAC ATG GTC AGC AGC GAA ACG          816
Ala Gly Glu Gln Gln Arg Val Ala Met His Met Val Ser Ser Glu Thr
            260                 265                 270

TTG TTC TGG GAA ACC ATG GAG AAA CTG AAA GCG CTT GGC GCC AGC TCG          864
Leu Phe Trp Glu Thr Met Glu Lys Leu Lys Ala Leu Gly Ala Ser Ser
        275                 280                 285

ATT CTG GTA CTG CCG ATC GAG AAG ATG ATG GAG TGA                          900
Ile Leu Val Leu Pro Ile Glu Lys Met Met Glu
    290                 295                 300
```

| | |
|---|---|
| | FIG._2A |
| | FIG._2B |

```
ATG AGC ACT GAA AAC ACT CTC AGC GTC GCT GAC TTA GCC CGT GAA AAT     48
Met Ser Thr Glu Asn Thr Leu Ser Val Ala Asp Leu Ala Arg Glu Asn
 1               5                  10                  15

GTC CGC AAC CTG GTA CCG TAT CAG TCT GCC CGC CGT CTG GGC GGT AAC     96
Val Arg Asn Leu Val Pro Tyr Gln Ser Ala Arg Arg Leu Gly Gly Asn
             20                  25                  30

GGC GAT GTC TGG CTG AAC GCG AAT GAA TTC CCG ACA GCG GTG GAG TTT    144
Gly Asp Val Trp Leu Asn Ala Asn Glu Phe Pro Thr Ala Val Glu Phe
                 35                  40                  45

CAG CTC ACC CAA CAA ACG CTT AAC CGC TAC CCG GAA TGC CAG CCA AAG    192
Gln Leu Thr Gln Gln Thr Leu Asn Arg Tyr Pro Glu Cys Gln Pro Lys
         50                  55                  60

GCC GTG ATT GAA AAC TAC GCG CAA TAT GCT GGC GTA AAG CCG GAG CAG    240
Ala Val Ile Glu Asn Tyr Ala Gln Tyr Ala Gly Val Lys Pro Glu Gln
 65                  70                  75                  80

GTG CTG GTC AGC CGC GGC GCG GAT GAA GGG ATC GAG CTG GTG ATC CGC    288
Val Leu Val Ser Arg Gly Ala Asp Glu Gly Ile Glu Leu Val Ile Arg
                 85                  90                  95

GCC TTC TGT GAA CCG GGG AAA GAC GCC ATT CTC TAC TGT CCG CCC ACT    336
Ala Phe Cys Glu Pro Gly Lys Asp Ala Ile Leu Tyr Cys Pro Pro Thr
             100                 105                 110

TAC GGT ATG TAC AGC GTC AGC GCC GAA ACC ATT GGC GTA GAG CGC CGG    384
Tyr Gly Met Tyr Ser Val Ser Ala Glu Thr Ile Gly Val Glu Arg Arg
         115                 120                 125

ACG GTT CCC GCG CTT GAA AAC TGG CAG CTG GAT CTA CAG GGG ATT TCC    432
Thr Val Pro Ala Leu Glu Asn Trp Gln Leu Asp Leu Gln Gly Ile Ser
 130                 135                 140
```

FIG._2A

```
GAC AAC CTT GAC GGC ACA AAA GTG GTG TTC GTT TGT AGC CCC AAT AAT      480
Asp Asn Leu Asp Gly Thr Lys Val Val Phe Val Cys Ser Pro Asn Asn
145                 150                 155                 160

CCT ACC GGA CAA CTT ATC AAC CCG CAG GAT CTG CGC ACG CTG CTG GAG      528
Pro Thr Gly Gln Leu Ile Asn Pro Gln Asp Leu Arg Thr Leu Leu Glu
                    165                 170                 175

TTG ACA CGC GGT AAA GCG ATA GTC GTC GCC GAC GAA GCT TAT ATT GAG      576
Leu Thr Arg Gly Lys Ala Ile Val Val Ala Asp Glu Ala Tyr Ile Glu
                180                 185                 190

TTT TGC CCG CAG GCC ACG CTG ACA GGC TGG CTG GTT GAA TAT CCT CAT      624
Phe Cys Pro Gln Ala Thr Leu Thr Gly Trp Leu Val Glu Tyr Pro His
            195                 200                 205

CTG GTT ATC CTG CGC ACA TTG TCG AAA GCT TTT GCG CTG GCG GGT CTG      672
Leu Val Ile Leu Arg Thr Leu Ser Lys Ala Phe Ala Leu Ala Gly Leu
                210                 215                 220

CGC TGC GGC TTT ACA CTG GCT AAT GAA GAG GTG ATC AAC CTG CTG TTA      720
Arg Cys Gly Phe Thr Leu Ala Asn Glu Glu Val Ile Asn Leu Leu Leu
225                 230                 235                 240

AAA GTG ATC GCC CCT TAT CCG CTT TCT ACG CCA GTG GCG GAT ATC GCC      768
Lys Val Ile Ala Pro Tyr Pro Leu Ser Thr Pro Val Ala Asp Ile Ala
                    245                 250                 255

GCC CAG GCG CTG TGC CCG CAG GGA ATA AAC GCA ATG CGC GAT CGC GTG      816
Ala Gln Ala Leu Cys Pro Gln Gly Ile Asn Ala Met Arg Asp Arg Val
                260                 265                 270

GCG CAG ACA GTG CAG GAA CGT CAG TAT CTG GTG AAT GCC CTG CAA CAG      864
Ala Gln Thr Val Gln Glu Arg Gln Tyr Leu Val Asn Ala Leu Gln Gln
            275                 280                 285

ACC GCC TGC GTA GAA CAC GTC TTT GAC TCT GAA ACC AAC TAT ATT CTG      912
Thr Ala Cys Val Glu His Val Phe Asp Ser Glu Thr Asn Tyr Ile Leu
        290                 295                 300

GCG CGG TTT ACC GCC TCC AGC AGC GTG TTT AAA TCC TTA TGG GAT CAG      960
Ala Arg Phe Thr Ala Ser Ser Ser Val Phe Lys Ser Leu Trp Asp Gln
305                 310                 315                 320

GGC ATT ATC TTA CGC GAT CAG AAT AAA CAA CCT TCT TTA AGC GGC TGC     1008
Gly Ile Ile Leu Arg Asp Gln Asn Lys Gln Pro Ser Leu Ser Gly Cys
                325                 330                 335

CTG CGG ATT ACG GTC GGC ACC CGC CAG GAA AAC CAG CGC GTC ATT GAC     1056
Leu Arg Ile Thr Val Gly Thr Arg Gln Glu Asn Gln Arg Val Ile Asp
                340                 345                 350

GCC TTA CGT GCG GAG CCA GTA TGA                                     1080
Ala Leu Arg Ala Glu Pro Val
            355                 360
```

FIG._2B

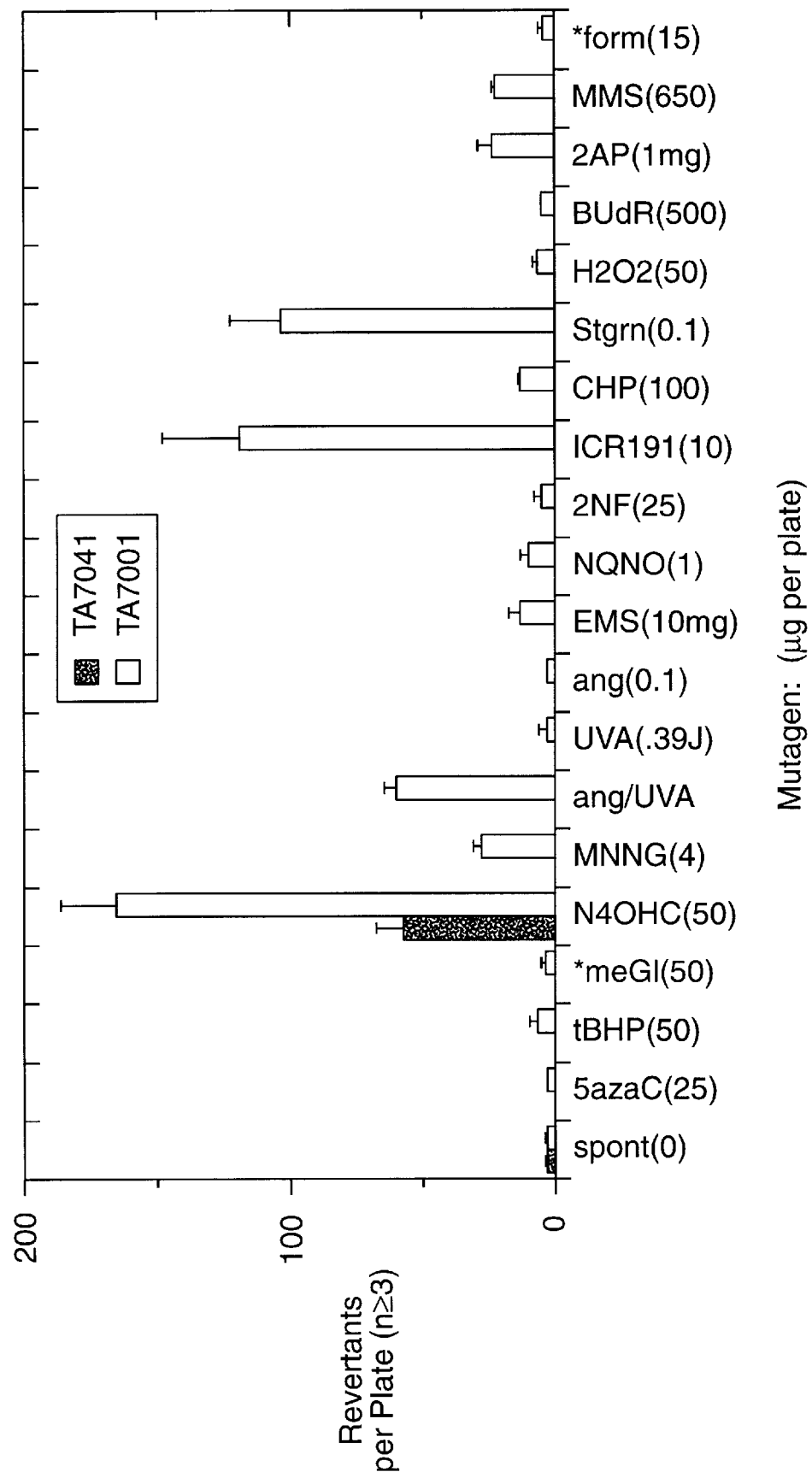
FIG._3

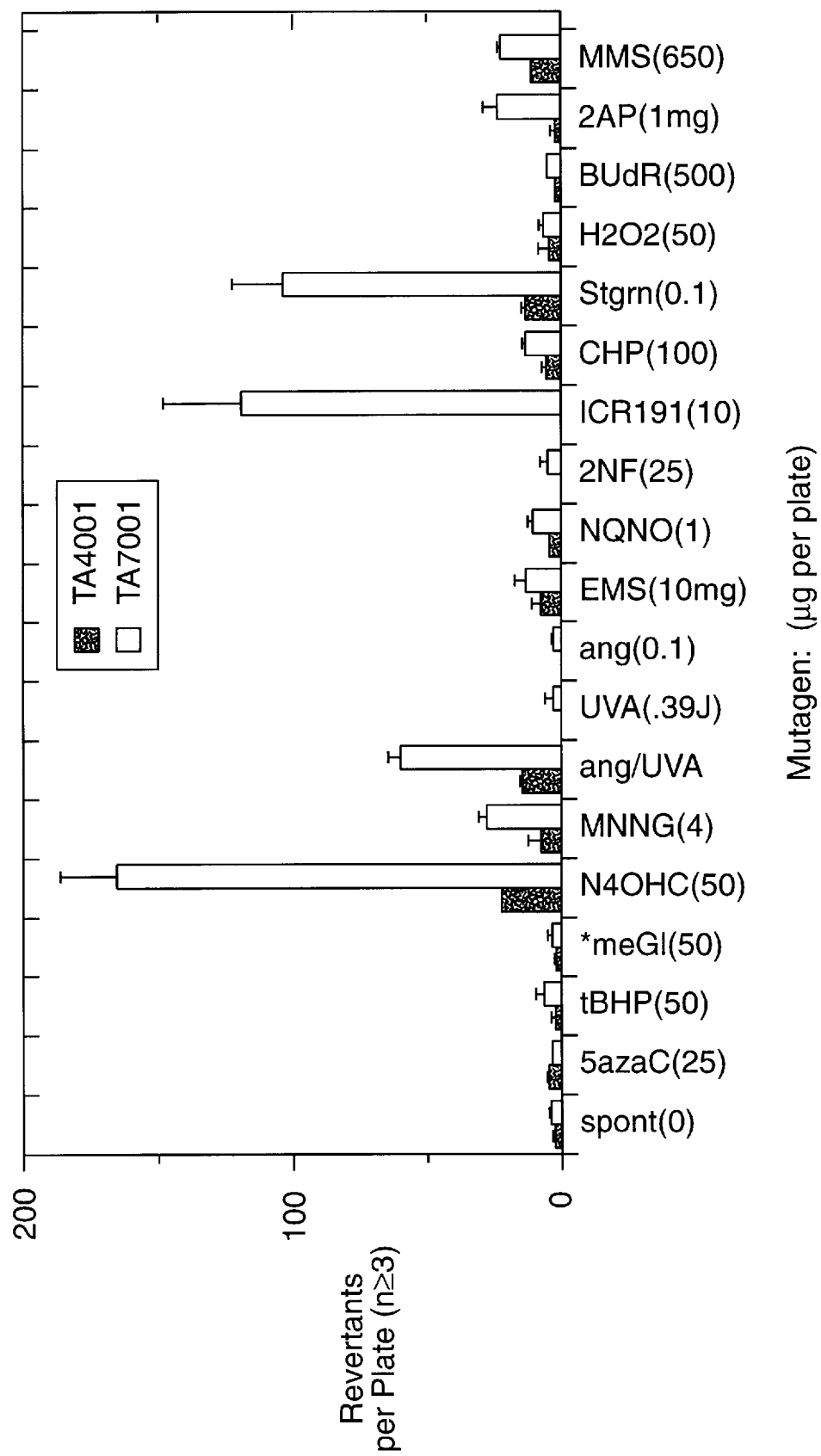
FIG._4

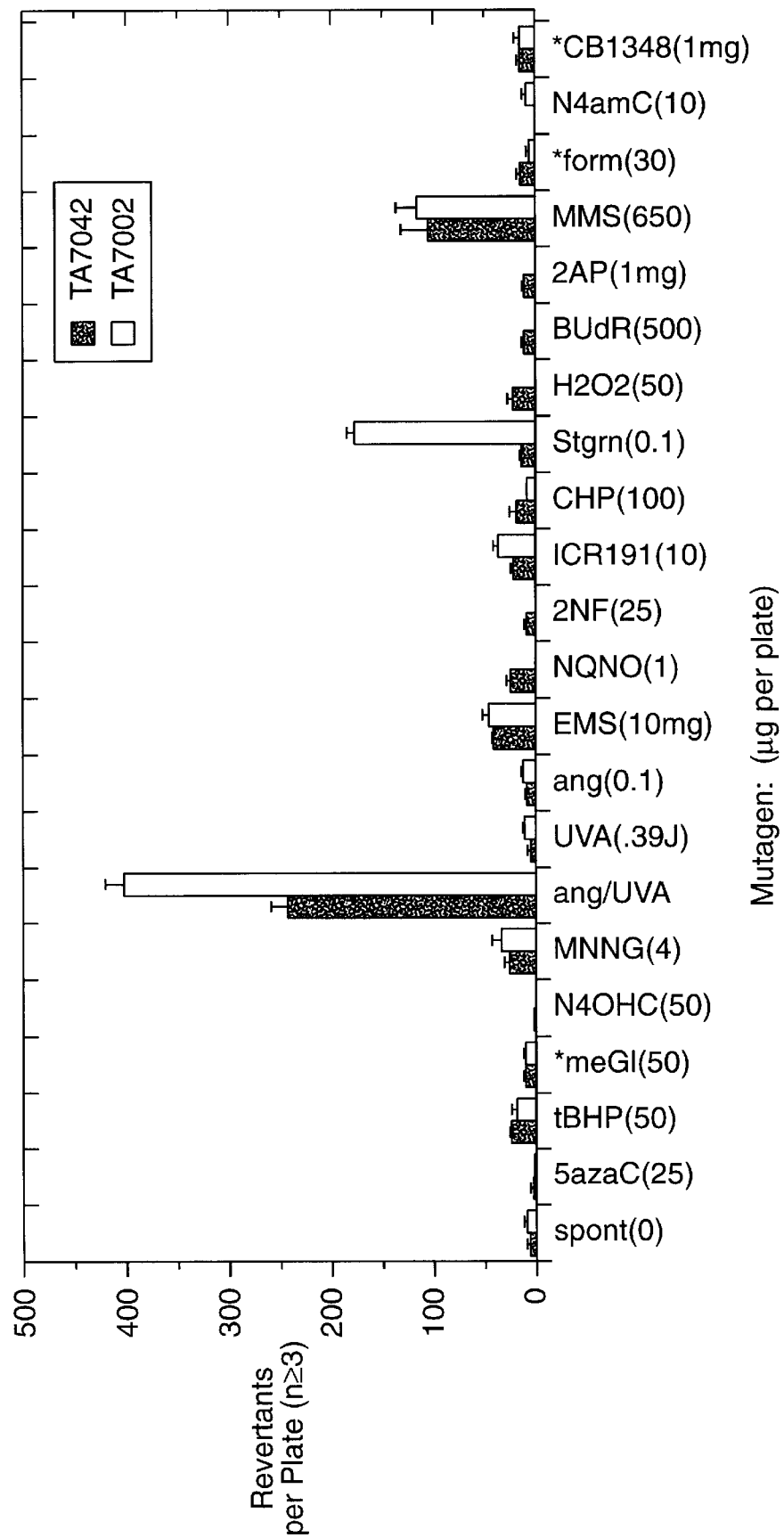
FIG._5

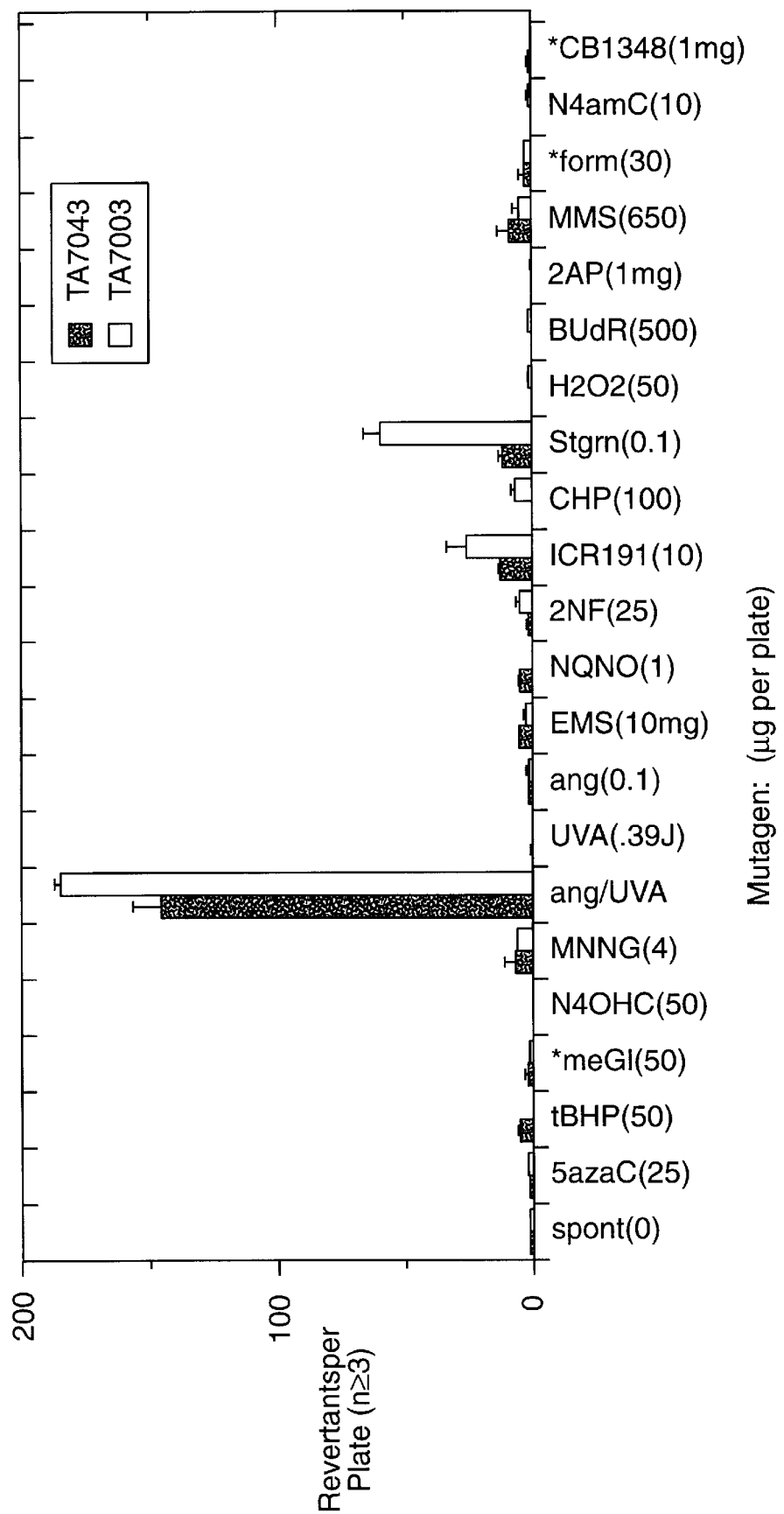
FIG._6

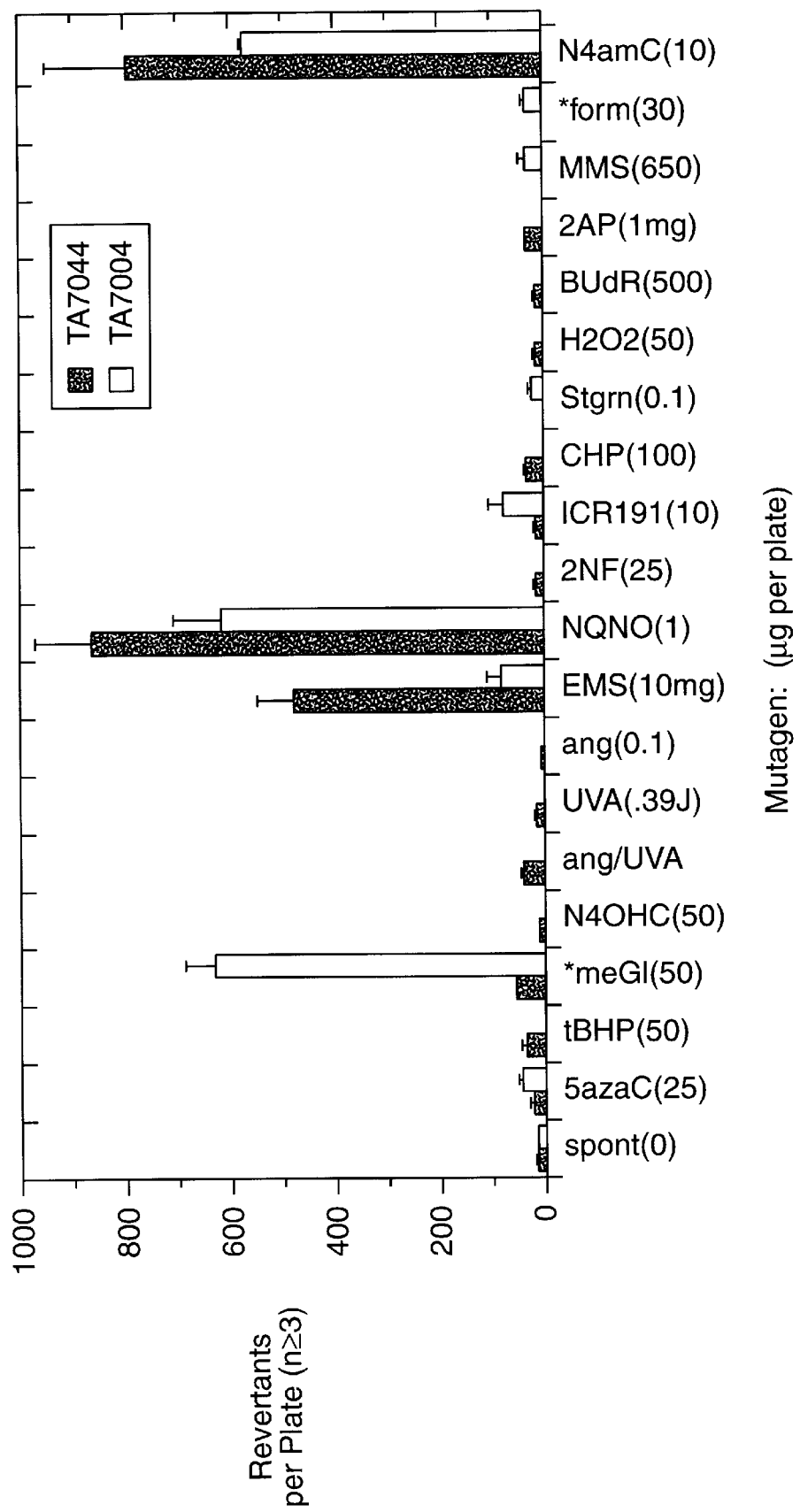
FIG._7

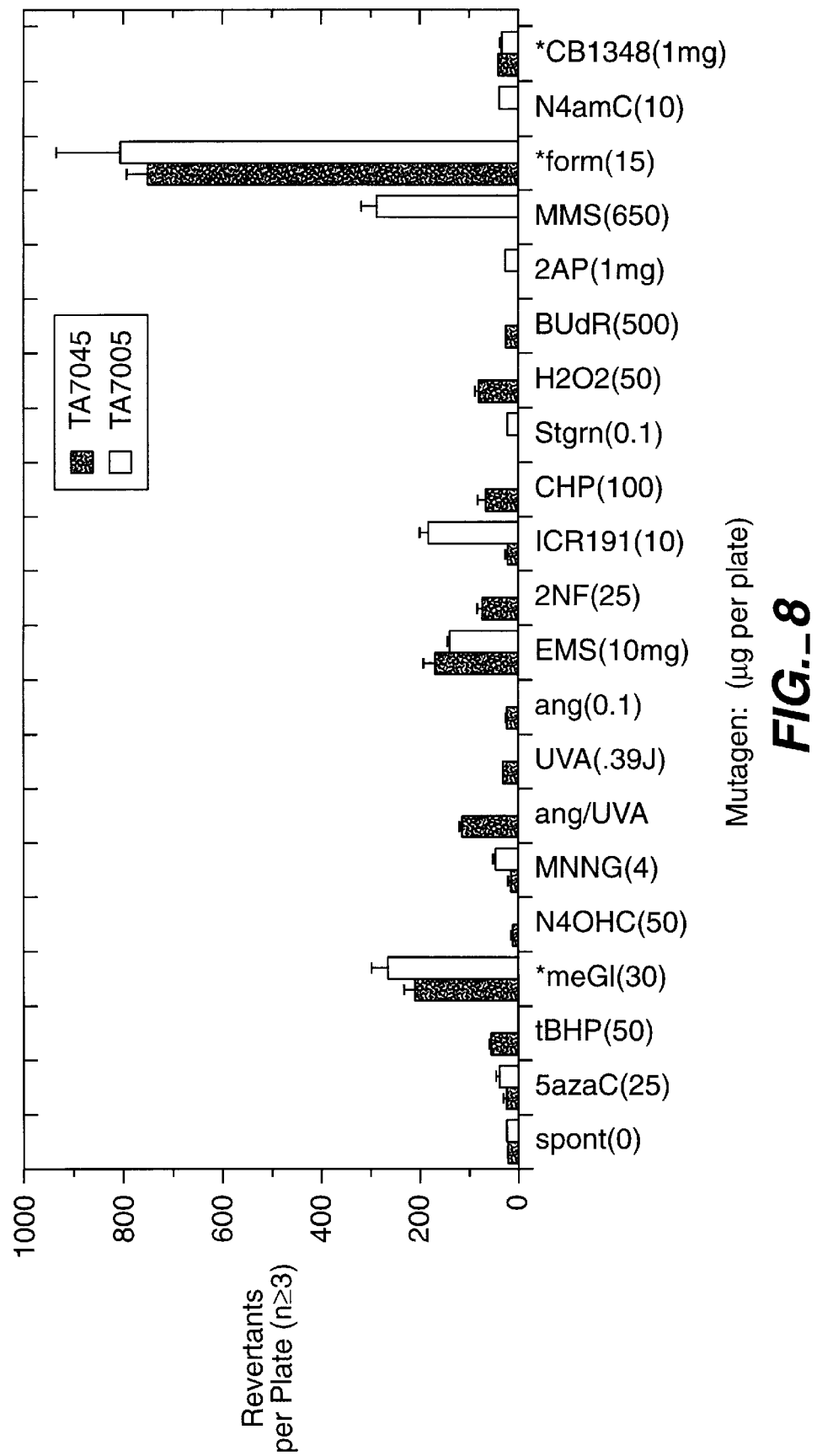
FIG._8

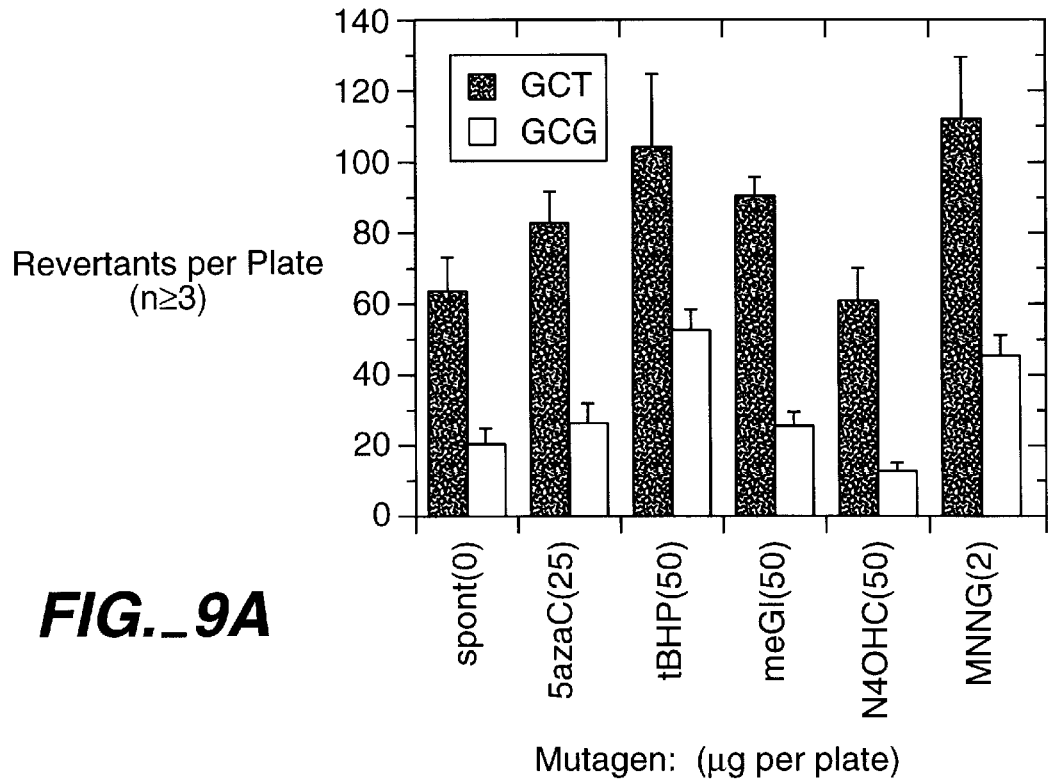
FIG._9A
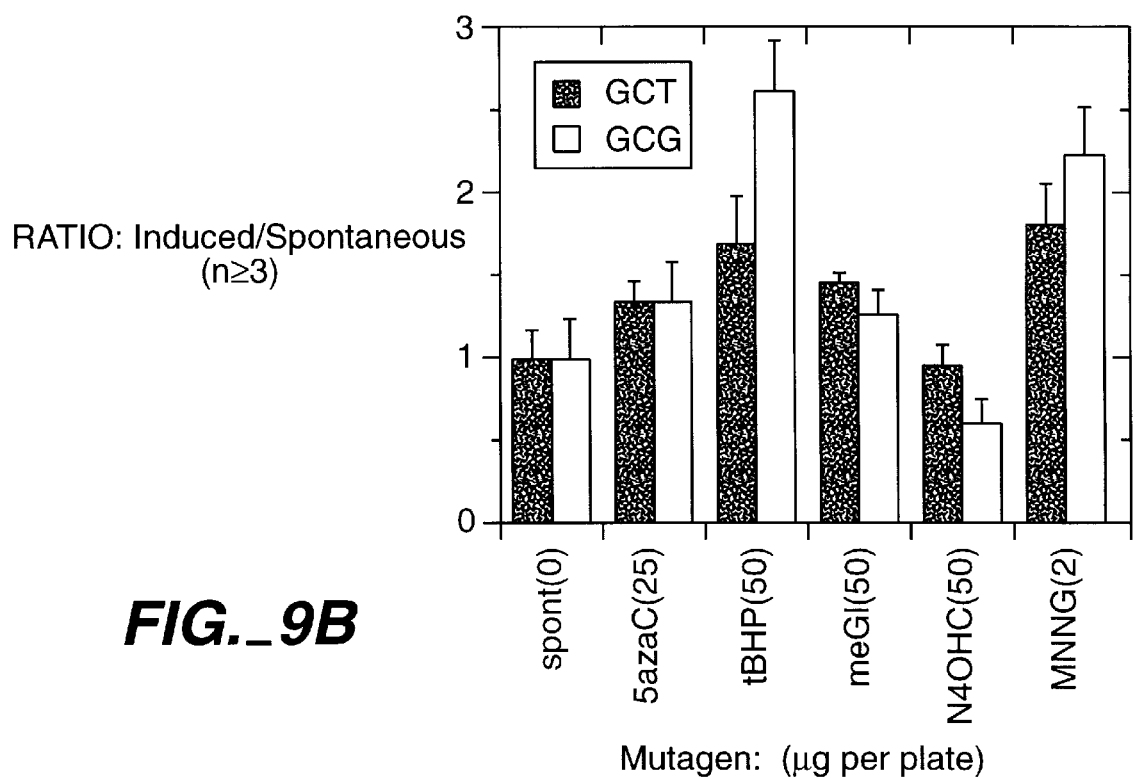
FIG._9B

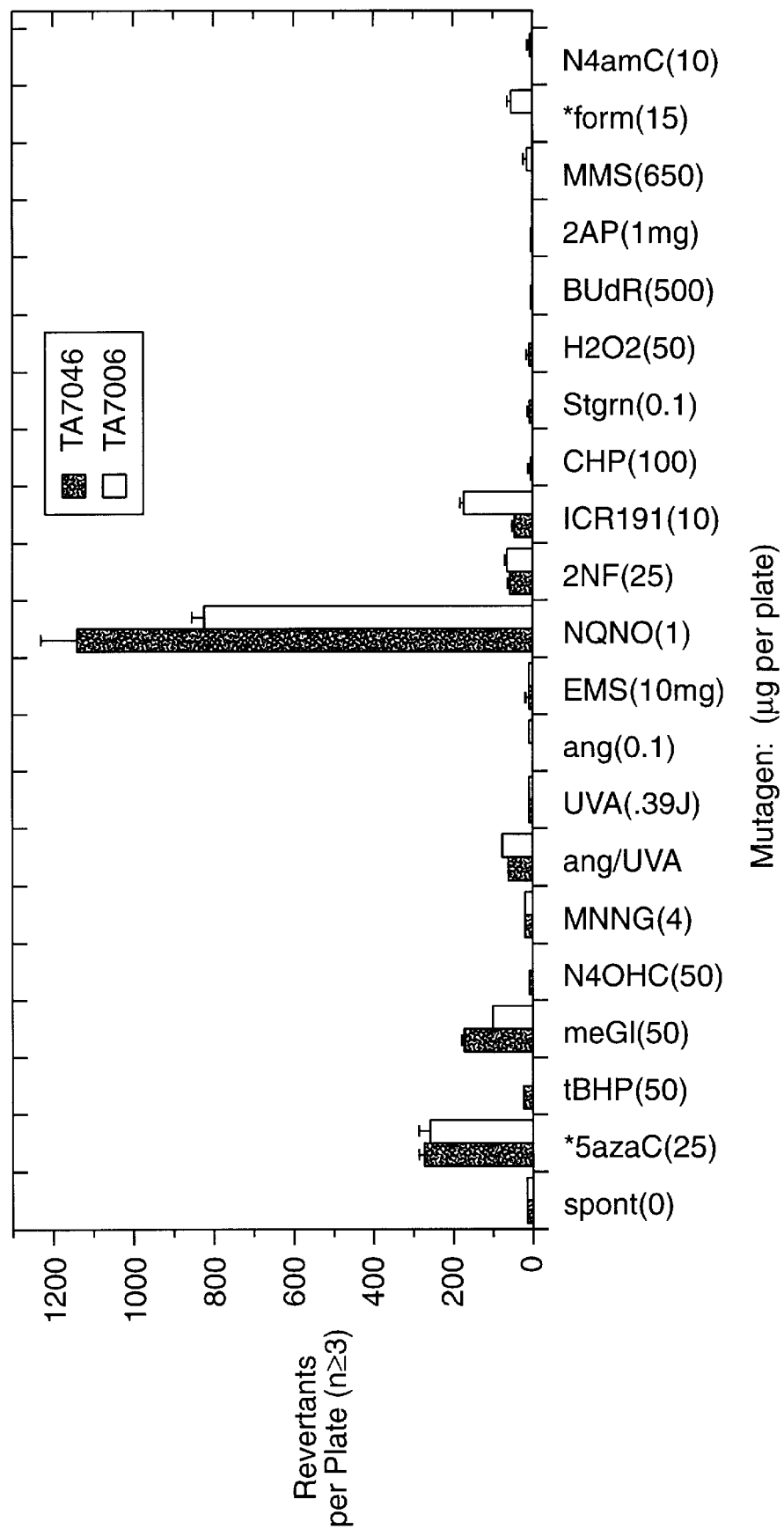

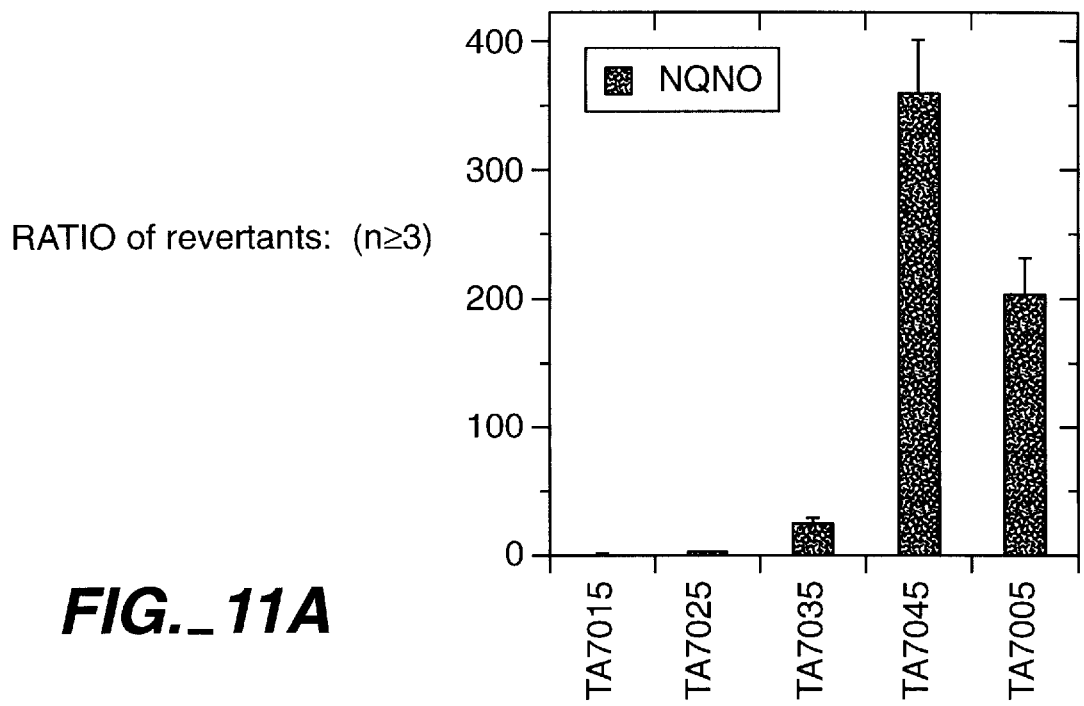
FIG._11A
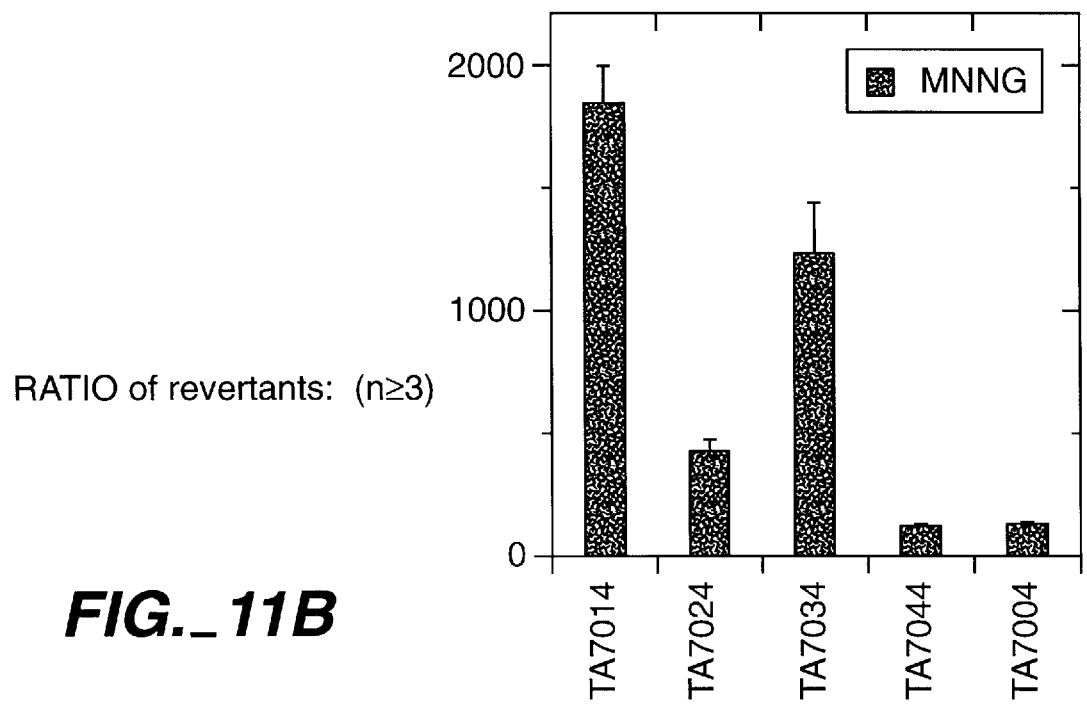
FIG._11B

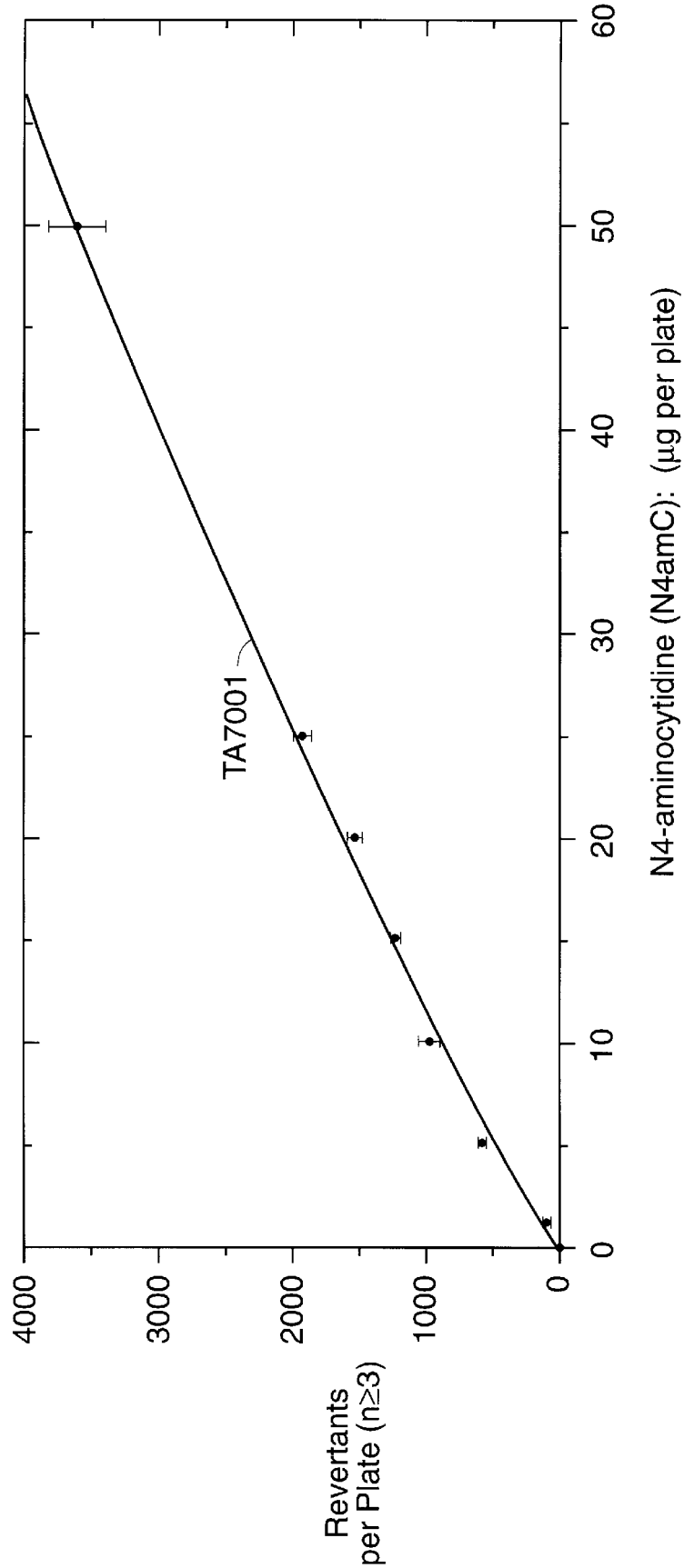
FIG._12

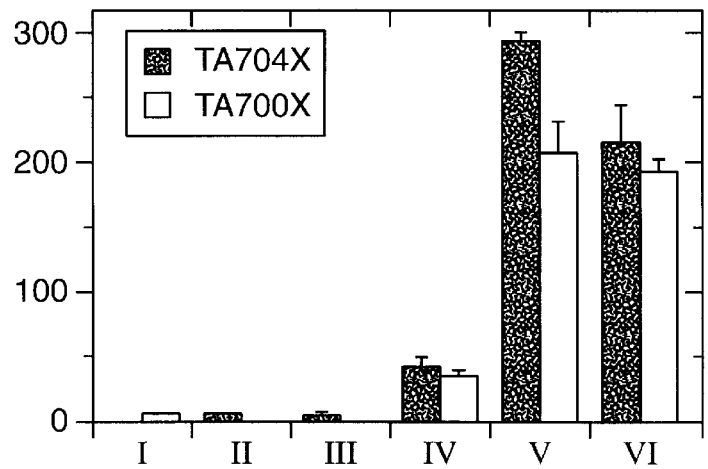
FIG._13A
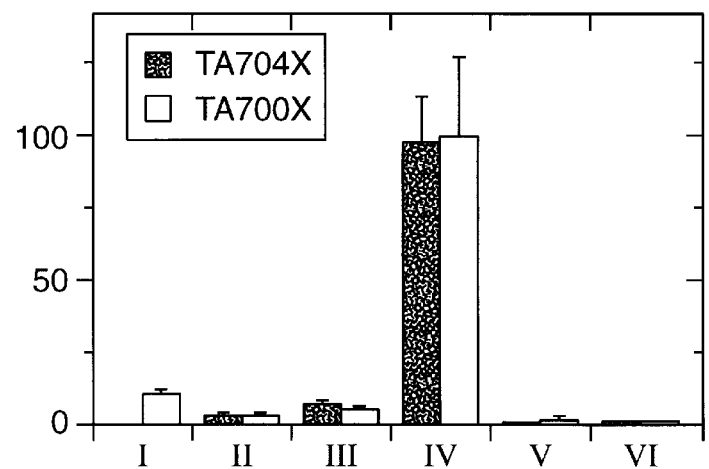
FIG._13B
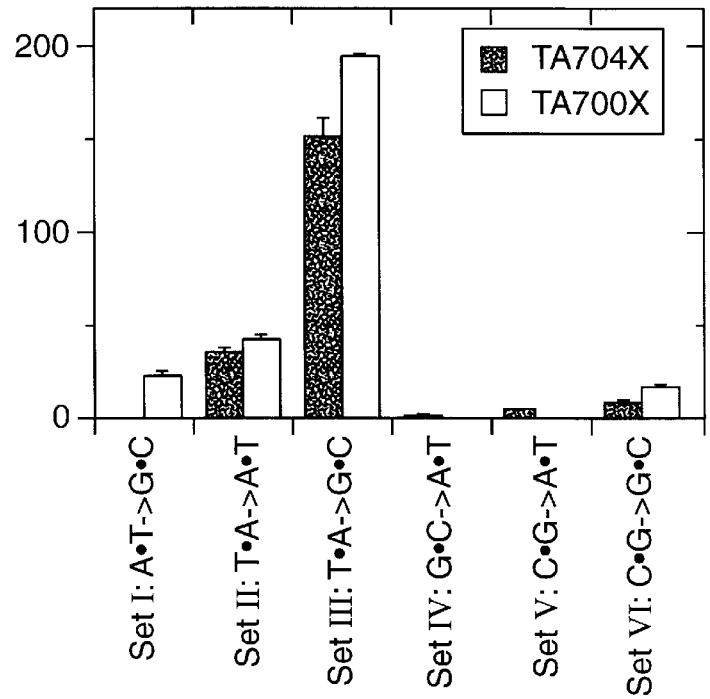
FIG._13C

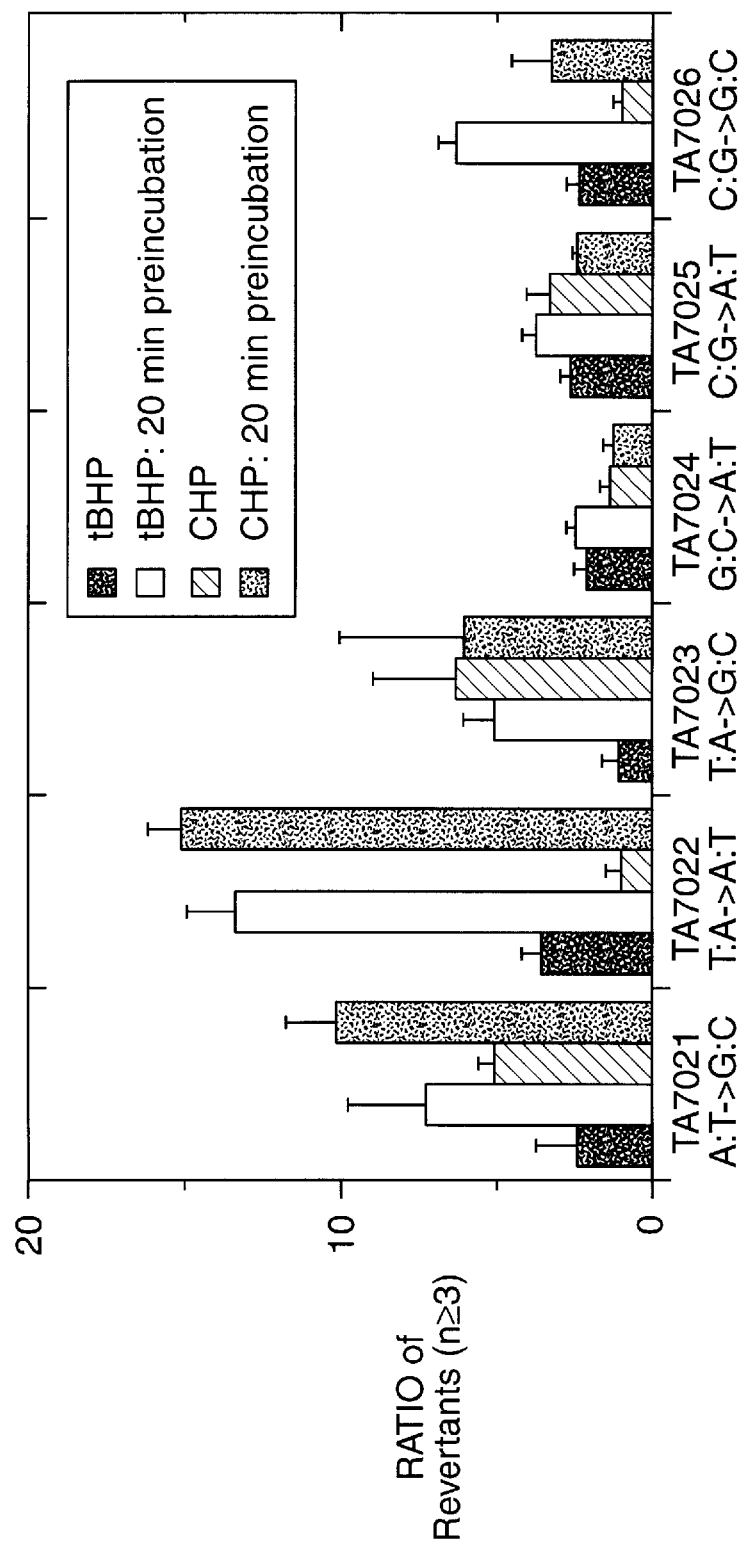
FIG._14

DETECTION SYSTEM FOR MUTAGENS THAT IDENTIFIES MUTAGENIC CHANGES

This is a continuation of application Ser. No. 08/137,627 filed Oct. 15, 1993, now U.S. Pat. No. 5,681,737.

TECHNICAL FIELD

The field of this invention concerns the construction of auxotrophic Salmonella strains diagnostic of each of the six types of base substitution mutations induced by mutagenic agents.

BACKGROUND

Several Salmonella typhimurium strains have been used widely in what is known as the Ames test to detect mutagenic agents. In this test, bacterial strains that require histidine for growth (His–), are mutated or reverted to wild type (His+) when treated with the test mutagenic agent. Thus the presence of a mutagen is indicated by the reversion of auxotrophic strains (His–) to wild type phenotype (His+). Many such strains, e.g., TA97a, TA98, TA100, TA102 and TA104 etc., are known in the art. While these bacterial strains allow the detection of mutagens they do not provide information on which of the six possible base pair substitution mutations are caused by the mutagen.

Three systems, employing cells other than Salmonella, exist in the art for detecting each of the six possible base substitution mutations (Cupples et al., 1989; Hampsey, 1991; Schaff et al., 1990; Stambrook et al., 1988). Six strains of Escherichia coli with mutations in the lacZ gene have been used by Cupples et al. (1989). These were developed for detecting specific base substitution mutations based on phenotypic reversion to wild type. However, these strains have not been widely used because of the unwieldiness of the mutagenicity assays and because phenotypic reversion has not been demonstrated conclusively to result exclusively from a specific base substitution mutation.

Another system has been developed using six yeast strains capable of detecting specific base substitution mutations without DNA sequence analysis, by reversion of the mutants to the wild type phenotype (Hampsey, 1991). However, yeast are more difficult to maintain and the mutagenicity assay requires almost two weeks to complete compared to 48 h for the Salmonella assay. Similar to the E. coli system of Cupples et al. (1989), phenotypic revertants of the yeast strains have not been sequenced adequately to confirm reversion via a single base substitution mutation. Thus, the possibility of other mechanisms of reversion, e.g., by missense suppression cannot be eliminated as causative of the observed phenotypic reversion.

Tester mammalian cells capable of detecting specific point mutations have also been reported (Schaff et al. 1990; Stambrook et al, 1988; U.S. Pat. No. 4,792,520). These references are essentially by the same authors and disclose similar subject matter. The references relate to a cell assay for specific base substitutions and frame shift mutations using non-reverting mammalian tester cells engineered to contain a mutated mouse adenine phosphoribosyl-transferase (APRT) gene. Specific point mutations are tested by treating tester cells (APRT–) with a mutagen and observing phenotypic reversion to APRT+. However, mammalian cells are much more expensive and too cumbersome for routine screening of mutagenic agents. The method of producing the mammalian tester cells relies on targeting the nucleotide sequence at one of the intron/exon junctions in the APRT gene. This method is clearly not relevant to prokaryotic cells like Salmonella typhimurium, as splicing of RNA is not characteristic of prokaryotic cells.

SUMMARY OF THE INVENTION

This invention relates to a system that is designed to detect mutational events and to identify which of the six possible base substitutions occur during those mutational events. The test system consists of six sets of strains of Salmonella typhimurium that carry base substitution mutations in the genes for histidine biosynthesis such that each set can be reverted to a normal wild type gene by a particular base pair substitution, e.g., A:T to G:C; T:A to A:T; T:A to G:C; G:C to A:T; C:G to A:T or C:G to G:C, or its equivalent, respectively, T:A to C:G; A:T to T:A; A:T to C:G; C:G to T:A; G:C to T:A or G:C to C:G. (Unless otherwise stated, in this application reference to a particular base pair substitution automatically includes its equivalent substitutions.) These particular base substitutions were confirmed by direct DNA sequence analysis of over 800 independent revertant colonies that grew in response to over twenty known mutagens. The new strains have considerably lower rates of spontaneous reversions and are about as sensitive as the current Ames strains. Thus, each set of the instant strains carries a unique codon as the target of mutational events so that when the predicted specific base change occurs at the codon, the reverted cells can grow, like wild type strains, without the addition of histidine.

As in the original Ames Salmonella mutagenicity assay, the invention is used as follows. The number of colonies of bacteria that grow following exposure to a test agent is a measure of the rate or frequency of mutations caused by that test agent. An agent capable of mutagenesis may consist of a single compound of known chemical purity and structure; or a mixture of chemical compounds such as that found in industrial wastes; or a complex biological mixture of unknown chemical composition such as crude extracts from plants; or radiation of different charges and energy levels; or any combination thereof. The test agent can be applied in any physical state, i.e., gaseous, liquid or solid. Induced mutation rates must be shown to increase in a dose-dependent manner at sub-lethal concentrations of the test agent. The initial slope of the dose-dependent curve (Bernstein et al., 1982) can be used to compare the potency of the newly tested compound to reference compounds (Claxon et al., 1991 (a) and (b)) or other established mutagens.

The test system is based on target mutations such that back-mutation or reversion of the target mutation results from a unique, and predictably specific, base change about 99% of the time. Thus, all bacterial colonies visible to the naked eye after 48 h of incubation at 37° C. represent unique base substitutions as predicted from each set of strains. The six target mutations are stable and revert at very low spontaneous frequencies, but at the same time are very sensitive to reversion when exposed to mutagens to provide quantitative measurements of the mutagenic potential of test agents.

BRIEF DESCRIPTION OF THE FIGURES

FIGS. 1 and 1A–1B show the DNA (SEQ ID NO:1) and amino acid (SEQ ID NO:2) sequence of wild type Salmonella typhimurium hisG gene.

FIGS. 2 and 2A–2B show the DNA (SEQ ID NO:3) and amino acid (SEQ ID NO:4) sequence of wild type Salmonella typhimurium hisC gene.

FIG. 3 is a graph showing reversion of Set I strains TA7041 and TA7001 by A:T to G:C transitions.

FIG. 4 is a graph showing a comparison of the sensitivity to mutagens of Set I strain, TA7001, and TA4001.

FIG. 5 is a graph showing reversion of Set II strains, TA7042 and TA7002 by T:A to A:T transversions.

FIG. 6 is a graph showing reversion of Set III strains TA7043 and TA7003 by T:A to G:C transversions.

FIG. 7 is a graph showing reversion of Set IV strains TA7044 and TA7004 by G:C to A:T transitions.

FIG. 8 is a graph showing reversion of Set V strains TA7045 and TA7005 by C:G to A:T transversions.

FIG. 9A is a graph showing the effect of context change from GCT to GCG on the mutagenic frequency for C:G to A:T transversions, expressed as the number of revertants.

FIG. 9B is a graph showing the effect of context change from GCT to GCG on the mutagenic frequency for C:G to A:T transversions expressed as the ratios of spontaneous frequencies.

FIG. 10 is a graph showing reversion of Set VI strains TA7046 and TA7006 by C:G to G:C transversions.

FIG. 11A is a graph showing reversion of Set V strains in response to treatment with 1 μg of NQNO (4-nitroquinoline-1-oxide).

FIG. 11B is a graph showing reversion of Set IV strains in response to treatment with 4 μg of MNNG (N-methyl-N'-nitro-N-nitroso-guanidine).

FIG. 12 shows a dose response curve of TA7001 revertants treated with different concentrations of $N^4$-aminocytidine.

FIGS. 13(A)–13(C) are graphs showing reversion of Sets I, II, III, IV, V and VI to 4-nitroquinoline-1-oxide (1 μg) (A), N-methyl-N'-nitro-N-nitroso-guanidine (4 μg) (B), and angelicin/UVA (C).

FIG. 14 is a graph showing the effect of a 20 min period of liquid preincubation prior to plate incorporation on the number of revertants of the strains in the TA702X series induced by t-butyl hydroperoxide (tBHP) and cumene hydroperoxide (CHP).

DESCRIPTION OF THE SPECIFIC EMBODIMENTS

The invention provides, in part, Salmonella strains capable of detecting mutagenic agents and diagnosing each of the six base substitution mutations induced in DNA by mutagens.

The following testing agents and their abbreviations used in this application are defined as follows:

| | |
|---|---|
| spont (0) | spontaneous at zero concentration of mutagens/plate |
| 5azaC (25) | 5-azacytidine at 25 μg/plate |
| tBHP (50) | t-butyl hydroperoxide at 50 μg/plate |
| meGl (50) | methyl glyoxal at 50 μg/plate |
| N4OHC (50) | $N^4$-hydroxycytidine at 50 μg/plate |
| MNNG (4) | N-methyl-N'-nitro-N-nitrosoguanidine at 4 μg/plate |
| ang/UVA | angelicin at 0.1 μg/plate and UVA at 0.39 ± 0.01 J/plate (J = joules) |
| UVA (0.39J) | UVA (0.39 ± 0.01 J) without angelicin |
| ang (0.1) | angelicin at 0.1 μg/plate without UVA |
| EMS (10 mg) | ethyl methanesulfonate at 10 mg or 10000 μg/plate |
| NQNO (1) | 4-nitroquinoline-1-oxide at 1 μg/plate |
| 2NF (25) | 2-nitrofluorene at 25 μg/plate |
| ICR191 (10) | (Institute for Cancer Research no. 191) 2-chloro-6-methoxy-9-[3-(2-chloroethyl)aminoethylamino]-1-azaacridine dihydrochloride at 10 μg/plate |
| CHP (100) | cumene hydroperoxide at 100 μg/plate |
| Stgrn (0.1) | streptonigrin at 0.1 μg/plate |
| H2O2 (50) | hydrogen peroxide at 50 μg/plate |
| BUdR (500) | bromouracil deoxyribose at 500 μg/plate |
| 2AP (1 mg) | 2-aminopurine at 1 mg or 1000 μg/plate |
| MMC (0.5) | mitomycin C at 0.5 μg/plate |
| MMS (650) | methyl methanesulfonate at 650 μg or 0.5 μl equivalents/plate |
| form (30) | formaldehyde at 30 μg/plate |
| N4amC (10) | $N^4$-aminocytidine at 10 μg/plate |
| CB1348 (1 mg) | chlorambucil at 1 mg or 1000 μg/plate |

All testing agents were purchased from Sigma, St. Louis, Mo. or Aldrich, Milwaukee, Wis. with the following exceptions: N4-hydroxycytidine (N4OHC) was synthesized according to Janion (1978). Angelicin (ang) was purchased from HRI Associates, Emeryville, Calif. and the UVA source was purchased from Thomas, Philadelphia, Pa. The acridine, ICR191 was purchased from Terochem, Edmonton, AB, Canada. The streptonigrin (Stgrn) was purchased from Flow Laboratories, McLean, Va. and the formaldehyde (form) was purchased from Fluka Chemika-BioChemika, Buchs, Switzerland.

As used herein, the terms "primary Salmonella bacterium", "primary bacterium", "primary cell" and equivalents thereof are used interchangeably to refer to any Salmonella cell having wild type or pseudo wild type DNA sequences. A pseudo wild type DNA sequence may differ from the wild type DNA sequence, however, there will be no physiological difference between a cell expressing the pseudo wild type sequence and one expressing the wild type sequence. The terms "derivative Salmonella bacterium", "derivative bacterium", "derivative cell" and equivalents are intended to refer to a Salmonella cell having the same DNA sequence as the primary Salmonella bacterium from which it is derived, with the exception that the DNA sequence of the derivative bacterium contains a thymine substituted for an adenine or for a guanine, an adenine substituted for a guanine, a guanine substituted for an adenine, a cytosine substituted for an adenine or a cytosine substituted for a guanine in the sense strand of a DNA sequence in the primary bacterial cell. Further, this substitution renders the derivative bacterium non-selectable for a characteristic for which the primary bacterium is selectable. Derivative bacterial cells may be constructed from primary bacterial cells by treatment of the primary bacterial cells with mutagens capable of interacting with and changing nucleic acids. Further, derivative bacterial cells may be constructed using recombinant DNA methods such as site-directed mutagenesis, polymerase chain reaction (PCR), and the like.

In one embodiment, the invention is directed to a derivative Salmonella bacterium derived from a primary Salmonella bacterium by substituting a thymine for adenine at a specific site in the sense strand of a DNA sequence in the primary Salmonella bacterium. Further, the derivative Salmonella bacterium is capable of reverting to the primary bacterium only as a result of a single substitution of the thymine at the specific DNA site with adenine, and in the absence of missense suppression. Reversion of derivative to primary cells may be brought about by treatment of the derivative cells with an agent that causes base substitution of adenine for thymine. Examples of such agents include angelicin activated by UVA$_{(320-400\ nm)}$ irradiation (ang/ UVA), chlorambucil (CB1348), streptonigrin (Stgrn) and t-butyl hydroperoxide (tBHP). Furthermore, the substituted thymine in the derivative Salmonella bacterium is stable, spontaneously reverting to adenine at a very low rate in the absence of an agent effecting an adenine-for-thymine substitution. Thus the spontaneous reversion of the derivative bacterium is preferably not more than about 5 revertants in $10^8$ derivative cells, more preferably not more than about 1 revertant in $10^8$ derivative cells and most preferably not more than about 8 revertants in $10^{10}$ derivative cells.

In another embodiment, the invention provides for a derivative Salmonella bacterium derived from a primary Salmonella bacterium in which a thymine is substituted for a guanine at a specific site in the sense strand of a DNA sequence contained in the primary Salmonella bacterium. Further, the derivative Salmonella bacterium reverts to the primary Salmonella bacterium as a result only of a single substitution of the thymine at the specific site in the derivative bacterium with guanine, and in the absence of missense suppression. Reversion of derivative to primary cells may be effected by treating the derivative cells with an agent that causes base substitution of guanine for thymine. Examples of such agents include ang/UVA, Stgrn and N-methyl-N'-nitro-N-nitrosoguanidine (MNNG). Furthermore, the substituted thymine in the derivative Salmonella bacterium is stable, i.e., spontaneously reverts to guanine in the absence of an agent effecting an guanine-for-thymine substitution at a very low rate. Thus the spontaneous reversion of the derivative bacterium is preferably not more than about 2 revertants in $10^8$ derivative cells, more preferably not more than about 1 revertant in $10^9$ derivative cells and most preferably not more than about 8 revertants in $10^{11}$ derivative cells.

In other embodiments, the invention comprises four other derivative Salmonella bacteria in which either an adenine is substituted for a guanine, a guanine is substituted for an adenine, a cytosine is substituted for an adenine or a cytosine is substituted for a guanine at a specific site in the sense strand of a DNA sequence of a primary Salmonella bacterial cell. Further, each of these derivative bacteria reverts to its respective primary Salmonella bacterium only as the result of a single base substitution of, respectively, guanine for adenine, adenine for guanine, adenine for cytosine or guanine for cytosine at the specific site. Again reversion of a derivative cell to its respective primary cell is effected by treating the derivative cell with an agent that causes the particular base substitution.

The DNA sequence of the primary bacterial cell prior to the thymine-for-adenine, thymine-for-guanine, adenine-for-guanine, guanine-for-adenine, cytosine-for-adenine or cytosine-for-guanine substitution may be any sequence encoding a polypeptide which confers to the cell a characteristic for which the cell may be selected in the presence of a selection agent. It is preferable that the selectable characteristic conferred on the primary bacterium be phenotypic. Most preferably, the selectable phenotypic characteristic would render primary bacterial cells capable of growth in the absence of a selection agent. It is also preferred that the non-selectable derived bacterium, which is non-selectable for the particular characteristic, be able to grow only in the presence of the same selection agent. Many examples of selectable characteristics that allow cell growth in the absence of a selection agent exist. For example, primary bacterial cells may be chosen that are selectable for prototrophic growth in the absence of supplements, such as amino acids like histidine or tryptophan, or a carbon source like lactose or glycerol.

The term "specific site" as used herein refers to a particular site in a DNA sequence of the primary bacterium or to the corresponding site in the DNA sequence of the derivative bacterium. The term "specific site" in the DNA of the primary bacterium herein has a functional definition and refers to a site in the DNA which when mutated by a thymine-for-adenine, adenine-for-guanine, guanine-for-adenine, cytosine-for-adenine or cytosine-for-guanine or by a thymine-for-guanine substitution renders the bacterium non-selectable for a characteristic for which the primary bacterium is selectable. The specific site in a DNA sequence at which a specific substitution may be introduced to render selectable cells non-selectable for a given characteristic may be determined from X-ray crystallography of the polypeptide encoded by the DNA of interest using methods well known in the art.

It is preferred that the specific site in the primary bacterium reside in a codon encoding an amino acid to be translated by only a small number of tRNA isoacceptors, each coded by genes in low copy number. For example, only one tRNA species has been found for the amino acids, cysteine, tryptophan and phenylalanine in E. coli. Furthermore, each tRNA gene is present in only one copy (Komine et al., 1990).

More preferably, the specific DNA site in the primary bacterium should encode an amino acid having no equivalent amino acids. Equivalent amino acids are amino acids having similar size, and/or charge, and/or similar degrees of hydrophobicity, such as tyrosine and phenylalanine, glutamate and aspartate, and leucine and isoleucine. Further, equivalent amino acids are functionally defined by their ability to replace other amino acids in a polypeptide without altering the biological activity of the polypeptide.

Most preferably, the specific site in the DNA in the primary bacterium should encode for an essential amino acid which when replaced with any other amino acid renders the polypeptide inactive. Essential amino acids may reside in the active site or co-factor binding site of a polypeptide or reside between two functional domains to provide the exact geometry of a regulatory site which is essential for activity. For example, amino acids which are determined from X-ray crystallography data of the polypeptide to participate in the active site or co-factor binding site may be selected with advantage. The appropriate base substitutions may be made using methods known by those of ordinary skill in the art as in the substitution of thymine for adenine or guanine bases in codons encoding for the amino acids in the polypeptide active site.

Further, where the DNA sequence of interest encodes a polypeptide having between about 15% and 25% homology to the amino acid sequence of a peptide in the same or another organism and the homologous peptide includes conservative amino acid residue substitutions, essential amino acids may be determined by aligning small segments of the polypeptide encoded by the DNA sequence of interest with the homologous peptide. Overall amino acid homologies of between 15% and 25% are generally considered trivial, but the resulting three-dimensional structures of the polypeptides may share the same physical geometries in critical regions of the protein. With homologies lower than 40%, small segments of different polypeptides can be analyzed by using a multiple sequence editor such as that developed by Mehta et al. (1989), to display segments of different peptides in parallel. Standard programs such as AALIGN and AACOMP (DNASTAR Inc., Microcomputer Systems, Madison, U.S.A.), based on the FASTP program (Lipman and Pearson, 1985) and the Needleman-Wunsch algorithm (Needleman and Wunsch, 1970) can be used to align amino acids in each segment. Gaps of varying lengths are introduced liberally between peptide segments to facilitate contiguous alignment of entire polypeptides with each other. The type and location of essential amino acids may be determined from invariant amino acid residues resulting from such alignments of the polypeptides encoded by the DNA sequence of interest.

Essential amino acids may be further determined, using methods known in the art (Saiki et al., 1988), by sequencing of DNA in derivative bacterial cells having a DNA mutation which renders these cells non-selectable for the desired characteristic and by comparing this DNA sequence with that in primary bacterial cells selectable for the same characteristic. It is preferred that the DNA sequences in primary and derivative bacterial cells be determined by direct sequencing. Where comparison of DNA sequences in primary and derivative bacterial cells shows a single nucleic acid substitution in a codon wherein the substituted codon encodes a different amino acid from a primary amino acid encoded by the equivalent codon in the selectable primary cell, the primary amino acid may be essential.

To ascertain whether an amino acid is an essential amino acid one may substitute the single nucleic acid base, using methods known in the art, in the first or second positions of the codon encoding the amino acid of interest with another base to produce a derivative codon such that the derivative codon encodes an amino acid which is different from the amino acid of interest. Cells containing derivative codons encoding each of the known amino acids other than the primary amino acid are tested for selectability for the characteristic of interest. Amino acids which when replaced by any other amino acid result in a cell non-selectable for the characteristic of interest are essential amino acids. Thus, essential amino acids are functionally defined as those amino acids which when replaced with any other amino acid result in abrogation of the activity of the polypeptide wherein they are disposed.

In one preferred embodiment, the derivative bacterium comprises a thymine substituted for an adenine at +650 in the hisC gene or a homologue thereof, wherein this substitution renders the derivative cells incapable of growth in the absence of histidine.

In yet another preferred embodiment, the derivative bacterium contains a thymine substituted for a guanine at +458 in the hisG gene or a homologue thereof, such that derivative cells having the thymine-for-guanine substitution do not grow in the absence of histidine.

A nucleic acid hisG homologue or hisC homologue is initially identified by substantial nucleic acid sequence homology to the nucleic acid sequences shown in, respectively, FIG. 1 (SEQ ID NO:1) and FIG. 2. (SEQ ID NO:3). Furthermore, a nucleic acid hisG homologue or hisC homologue may also be identified by substantial amino acid sequence homology to the amino acid sequences shown in, respectively, FIG. 1 (SEQ ID NO:2) and FIG. 2. (SEQ ID NO:4). Thus, such homology can be based upon the overall nucleic acid or amino acid sequence. Where the homology is based on the amino acid sequence, it is preferred that the overall homology of the amino acid sequence be greater than 40%, more preferably greater than 65% and most preferably greater than 80% homologous. Homology based on nucleic acid sequence is commensurate with amino acid homology but takes into account the degeneracy in the genetic code. Accordingly, the nucleic acid sequence homology may be substantially lower than that based on protein sequence.

Thus, where nucleic acid sequence homology is employed, the overall homology of the nucleic acid sequence is preferably greater than 35%, more preferably greater than 60% and most preferably greater than 75% homologous.

A hisG or hisC homologue can be readily identified by standard methods utilizing the nucleic acid sequence depicted in, respectively, FIG. 1 (SEQ ID NO:1) and FIG. 2. (SEQ ID NO:3). For example, labelled probes corresponding to the hisG or hisC nucleic acid sequences can be used for in situ hybridization to detect the presence of a homologue in a particular cell. In addition, such probes can be used to screen genomic or cDNA libraries of different Salmonella species or to identify one or more bands containing all or part of a homologue by hybridization to an electrophoretically separated preparation of genomic DNA from different Salmonella strains digested with one or more restriction endonucleases.

The hybridization conditions (Hames and Higgins, 1987) will vary depending upon the probe used. Hybridization is preferably carried out under low stringency conditions. For example, prehybridization of filters carrying genomic or cDNA is incubated at 42° C. for 6 h or more in 30% formamide (1.65 ml formamide, 1.375 ml 20× SSPE, 0.55 ml 100× Denhardt's reagent, 0.275 ml 20% SDS, 1.1 ml water, 0.25 ml sheared salmon sperm DNA). This is followed by hybridization for a minimum of 24 h at 42° C. in 30% formamide (1.8 ml formamide, 1.5 ml 20× SSPE, 0.12 ml 100× Denhardt's reagent, 1.5 ml water, 0.096 ml sheared salmon sperm DNA and 0.624 ml denatured DNA probe labelled with $^{32}$P).

Once the homologue is identified, it can be cloned and, if necessary, its constituent parts recombined. Once isolated from its natural source, e.g., contained within a plasmid or other vector or excised therefrom as a linear nucleic acid segment, the homologue can be further used as a probe to identify and isolate other homologues.

In another aspect, Salmonella bacteria having two substituted nucleic acids in hisC or hisG are provided. In one embodiment, the Salmonella bacteria contain a hisG, or homologue thereof, having a guanine at site +506, i.e., in the second position of the codon, and a guanine at site +507, i.e., in the third, or wobble, position of the same codon. The position of the codon in a hisG homologue can be determined by finding a functionally equivalent codon by aligning the hisG nucleic acid sequence with the amino acid sequence of the homologue.

In another embodiment, Salmonella bacteria are provided having a hisG, or homologue thereof, containing a cytosine at site +506, i.e., in the second position of the codon, and a guanine at site +507, i.e., in the wobble position of the same codon.

Yet another aspect, the invention is directed to providing Salmonella typhimurium mutants capable of detecting specific base substitution mutations. As herein described, unless otherwise indicated, the base substitutions and mutations refer to the sense strand of DNA but also encompass the appropriate equivalents. For example, a base substitution of thymine for guanine would also include the substitution of adenine for cytosine in the complementary strand. Included are Salmonella typhimurium mutants capable of detecting A:T to G:C substitutions consisting of the strains TA7001, TA7021, TA7031 and TA7041. Also included are Salmonella typhimurium mutants which detect T:A to A:T substitutions consisting of the strains TA7002, TA7012, TA7022, TA7032 and TA7042. Further included are Salmonella typhimurium strains diagnostic of T:A to G:C substitutions consisting of the strains TA7003, TA7013, TA7023, TA7033 and TA7043. Also provided are *Salmonella typhimurium* mutants capable of detecting G:C to A:T substitutions consisting of the strains TA7004, TA7014, TA7024, TA7034 and TA7044. Other *Salmonella typhimurium* mutants which detect C:G to A:T substitutions are also provided and consist of strains TA7005, TA7015, TA7025, TA7035 and TA7045. In addition, *Salmonella typhimurium* mutant strains diagnostic of C:G to G:C mutations are also provided and consist of TA7006, TA7026, TA7036 and TA7046.

In yet a further aspect, the invention provides DNA sequences comprising hisC, or homologues thereof, having a thymine at site +650. Other DNA sequences provided by the invention include a hisG homologue containing a thymine at site +458, or a guanine at site +507 with either a guanine or cytosine at site +506.

Another embodiment provides for autonomously replicating, transferable DNA molecules harboring the hisC or hisG homologues having substituted nucleic acids. The term "autonomously replicating" refers to any DNA sequence capable of replicating in a cell and of directing expression of heterologous sequences disposed therein. The term "transferable" refers to DNA sequences that can be introduced into a host cell. Such autonomously replicating and transferable DNA sequences include plasmids, bacteriophages, and animal or plant viruses, with or without inserted heterologous sequences. The DNA sequence will contain transcription and translation regulatory sequences, transcription and translation stop signals and at least one restriction site sequence for a given restriction enzyme.

Still another embodiment of the invention is directed to host cells comprising autonomously replicating, transferable DNA molecules containing the hisC or hisG homologues having substituted nucleic acids. The DNA elements can be transferred to a suitable host cell by appropriate means including transformation, transfection, or infection. Host cells bearing, replicating and expressing the inserted DNA sequences are then subjected to conditions appropriate for growth of the host cell.

A wide variety of organisms may be employed as hosts, particularly those having polypeptides with homologous bioactivitiy to the activity of the polypeptide translational products of hisC and hisG. Host cells having rfa mutations are desirable because they receive autonomously replicating transferable DNA easily and also bulky test agents. Further, host cells should be devoid of the pSLT plasmid (Sanderson et al., 1983) which may be associated with virulence properties in Salmonella. In addition, host cells that have specific defects in their DNA repair systems, such as mutations which inactivate genes responsible for recombinatorial and mismatch repair, may increase the spectrum of mutagenic agents detected in hisC and hisG. Other species include *Salmonella abony*, but of particular interest are subspecies of *Salmonella typhimurium*, including LT2, LT7 and LT22 (Sanderson et al., 1987).

In yet another aspect, a kit is provided for characterizing each of the six specific base substitution mutations induced by a mutagenic agent. The kit comprises at least one series of derivative Salmonella bacteria strain from each of the six sets, each derivative bacterium being capable of detecting one of the six base substitution mutations, namely A:T to G:C, T:A to A:T, T:A to G:C, G:C to A:T, C:G to A:T and C:G to G:C. The kit finds use in, for example, determining the type and relative proportion of specific substitution mutations induced by therapeutic agents. Many compounds used in therapy have undesirable genotoxic effects on non-target cells.

Where specific base substitution mutations are implicated in the genotoxic effects of a therapeutic compound, strategies may be devised to redesign that part of the compound responsible for the genotoxic effects without destroying its therapeutic usefulness. The kit may be used to screen for the efficacy of redesigned therapeutic compounds in inducing specific DNA base substitutions. Further, several compounds are used desirably for their genotoxic effects, on for example tumor cells. The design of these compounds may be manipulated to enhance the compound's activity in producing specific DNA base substitution mutations causative of cell toxicity. The kit finds use in screening derivative compounds for the spectrum of the type and relative proportion of specific substitution mutations.

Each of the derivative bacteria in the kit is derived from a primary bacterium. The primary bacterium from which each of the derivative bacteria are constructed may be the same or a different bacterium, provided that the primary bacterium of each of the derivative bacteria is selectable for a given characteristic.

Furthermore, each of the strains from the six sets of derivative bacteria are non-selectable for the same characteristic for which the primary bacteria are selectable. Additionally, each of the non-selectable derivative bacteria reverts to a cell selectable for that characteristic only as a result of one of the six possible base substitutions for which the revertant bacterium is diagnostic and in the absence of missense suppression. This reversion can be brought about either as a result of treatment with an agent which causes the specific base substitution of interest or spontaneously, i.e., in the absence of such agents. However, spontaneous reversion is a relatively rare event. The derivative bacteria used to diagnose the specific mutations preferably have a spontaneous reversion rate no greater than about 0.00002% (50 revertants in $4\times10^8$ cells). It is preferable that derivatives specific for substituting A:T with G:C, T:A with A:T, T:A with G:C, G:C with A:T, C:G with A:T and C:G with G:C, are respectively incapable of more than about 0.000003%, 0.000005%, 0.000002%, 0.00001%, 0.00001% and 0.000005% spontaneous reversion. More preferably, these derivatives do not revert, respectively, more than about 0.0000003%, 0.000001%, 0.0000001%, 0.000002%, 0.000003% and 0.0000005%. It is most preferable that spontaneous reversion of these derivatives is respectively not more than about 0.00000003%, 0.00000008%, 0.000000008%, 0.0000001%, 0.0000001% and 0.00000003%.

Another specific embodiment is directed to a kit wherein the derivative bacteria capable of detecting each of the six specific base substitutions are *Salmonella typhimurium* strains having a mutation in hisC or hisG of the his operon and which do not grow in the absence of histidine in the culture medium. As shown in Table 1, the derivatives diagnostic of A:T to G:C substitutions are selected from the strains TA7001, TA7011, TA7021, TA7031 and TA7041, those diagnostic of T:A to A:T substitutions are selected from the strains TA7002, TA7012, TA7022, TA7032 and TA7042, those diagnostic of T:A to G:C substitutions are selected from TA7003, TA7013, TA7023, TA7033 and TA7043, those diagnostic of G:C to A:T substitutions are selected from TA7004, TA7014, TA7024, TA7034 and TA7044, those diagnostic for C:G to A:T substitutions are selected from TA7005, TA7015, TA7025, TA7035 and TA7045, and those diagnostic for C:G to G:C substitutions are selected from TA7006, TA7016, TA7026, TA7036 and TA7046.

Yet a further embodiment comprises kits for characterizing each of the six possible base substitution mutations.

Many cancers are known to result from a specific, or limited repertoire of, base substitution mutations in critical genes, such as oncogenes. It is therefore desirable to provide kits which can detect agents capable of inducing the specific substitution mutations of interest. Thus, in a preferred embodiment, kits are provided for characterizing specific substitution of guanine for adenine, adenine for thymine, guanine for thymine, adenine for guanine, adenine for cytosine, or guanine for cytosine.

In a further aspect, a method is provided for characterizing specific classes of DNA base substitution mutations induced by mutagenic agents. The method to detect types of base transition mutations employs use of two Salmonella strains, each being non-selectable for a given characteristic, and each capable of reverting to a cell selectable for the same characteristic exclusively as a result of only one of two possible base transition mutations, and, therefore, in the absence of missense suppression. The mutagenic agent is contacted separately with each of the strains under conditions permitting base transition in the DNA of the strains by the mutagen. As a positive control, both tester strains should also be treated, separately, with a reference mutagen $N^4$-aminocytidine (N4amC), which is known to induce both A:T to G:C and G:C to A:T transitions.

Furthermore, a method to detect types of transversion mutations employs use of four Salmonella strains, each being non-selectable for a given characteristic, and each capable of reverting to a cell selectable for the same characteristic exclusively as a result of only one of four possible base transversion mutations and, therefore, in the absence of missense suppression. The mutagenic agent is contacted separately with each of the strains under conditions permitting base transversion in the DNA of the strains by the mutagen. As a positive control, the tester strains should also be treated, separately, with a reference mutagen known to induce the specific base transversion (Table 2) for which the tester strain is diagnostic.

These conditions of treatment vary depending on such factors as the stability of the mutagenic agent, e.g., temperature or light sensitivity, solubility in solvents compatible with the tester strains and chemical nature of the mutagen, e.g., the concentration required to cause base substitution mutation in combination with a minimal effect on the viability of the tester strains.

Following contacting of the tester strains with the mutagenic agent, or the reference mutagens, the treated cells are cultured under appropriate conditions which select for revertant cells having the desired selectable characteristic using conventional methods well known in the art for culturing Salmonella cells, such as those described by Maron et al. (1983). The treated cells are grown for a sufficient length of time, e.g., about 48 h when incubated at 37° C., to allow formation of colonies from cells having the desired selectable characteristic. Observation of colonies derived from a strain treated with the mutagen indicates that the mutagen induces the specific base substitution mutation for which that strain is diagnostic. Thus, each of the base substitution mutations caused by the mutagen can be determined.

In yet another aspect, the invention is directed to a method for reducing missense suppression of a mutation at a specific site in a derivative codon in a DNA sequence, wherein the derivative codon is derived from a primary codon, the mutation in the derivative codon is present in either the base at the first or second site in the codon, and wherein the primary and derivative codons have the same base in the wobble, i.e., third, site. The derivative codon can be obtained from the primary codon by treating the DNA sequence wherein the codon is disposed with mutagenic agents or by site-directed mutagenesis and the like. The method consists of substituting the base in the wobble site of the derivative codon with a different base, with the proviso that if the base in the wobble site of the primary codon were substituted with the substitute base, this substitution would result in a pseudo primary codon which encodes an amino acid that is equivalent to the amino acid encoded by the primary codon.

A further aspect of the invention provides for a method for reducing missense suppression of a mutation at the first or second site of a codon, by substituting the base in the wobble, i.e., third, site of the same codon with a guanine.

In yet a further aspect, a method is provided for making a mutation in the first or second position of a codon, wherein the mutation is not suppressed by an extragenic element. The term "extragenic element" herein refers to the gene product of a nucleic acid sequence that is not present in the gene sequence wherein the codon of interest is contained. An example of an extragenic element includes a gene encoding a tRNA sequence. The term "suppression" in this context refers to an abolishment of the phenotype expressed by a mutation. In this example, the term "suppressed" refers to the translation of a particular codon, which encodes a particular amino acid, to another amino acid other than the particular amino acid for which this codon encodes. The method comprises, in any order, substituting the base in the first or second codon positions with another base that is different from the base it is substituting and substituting the base in the wobble position of the codon with a guanine.

Methods for reducing missense suppression of a mutation or for making mutations that are not suppressible find use in, for example, producing cells that require no DNA sequencing by an investigator to confirm that any are diagnostic of specific base substitution mutations.

TABLE 1

SETS OF TESTER STRAINS

| SET | BASE CHANGE DETECTED | his MUTATION | ADDITIONAL FEATURES | | | STRAIN DESIGNATION |
|---|---|---|---|---|---|---|
| | | | REPAIR[1] | LPS[2] | R FACTOR[3] | |
| I | A:T→G:C | hisG1775 | Δara9 ΔuvrB | rfa1041 | pKM101 | TA7001 |
| | " | " | " | — | — | TA7011 |
| | " | " | " | — | pKM101 | TA7021 |
| | " | " | " ΔuvrB | galE503 | — | TA7031 |
| | " | " | " ΔuvrB | galE503 | pKM101 | TA7041 |

TABLE 1-continued

SETS OF TESTER STRAINS

| SET | BASE CHANGE DETECTED | his MUTATION | ADDITIONAL FEATURES REPAIR[1] | LPS[2] | R FACTOR[3] | STRAIN DESIGNATION |
|---|---|---|---|---|---|---|
| II  | T:A→A:T | hisC9138 | Δara9 ΔuvrB | rfa1042 | pKM101 | TA7002 |
|     | "       | "        | "           | —       | —       | TA7012 |
|     | "       | "        | "           | —       | pKM101  | TA7022 |
|     | "       | "        | ΔuvrB       | galE503 | —       | TA7032 |
|     | "       | "        | ΔuvrB       | galE503 | pKM101  | TA7042 |
| III | T:A→G:C | hisG9074 | Δara9 ΔuvrB | rfa1043 | pKM101  | TA7003 |
|     | "       | "        | "           | —       | —       | TA7013 |
|     | "       | "        | "           | —       | pKM101  | TA7023 |
|     | "       | "        | ΔuvrB       | galE503 | —       | TA7033 |
|     | "       | "        | ΔuvrB       | galE503 | pKM101  | TA7043 |
| IV  | G:C→A:T | hisG9133 | Δara9 ΔuvrB | rfa1044 | pKM101  | TA7004 |
|     | "       | "        | "           | —       | —       | TA7014 |
|     | "       | "        | "           | —       | pKM101  | TA7024 |
|     | "       | "        | ΔuvrB       | galE503 | —       | TA7034 |
|     | "       | "        | ΔuvrB       | galE503 | pKM101  | TA7044 |
| V   | C:G→A:T | hisG9130 | Δara9 ΔuvrB | rfa1045 | pKM101  | TA7005 |
|     | "       | "        | "           | —       | —       | TA7015 |
|     | "       | "        | "           | —       | pKM101  | TA7025 |
|     | "       | "        | ΔuvrB       | galE503 | —       | TA7035 |
|     | "       | "        | ΔuvrB       | galE503 | pKM101  | TA7045 |
| VI  | C:G→G:C | hisC9070 | Δara9 ΔuvrB | rfa1046 | pKM101  | TA7006 |
|     | "       | "        | "           | —       | —       | TA7016 |
|     | "       | "        | "           | —       | pKM101  | TA7026 |
|     | "       | "        | ΔuvrB       | galE503 | —       | TA7036 |
|     | "       | "        | ΔuvrB       | galE503 | pKM101  | TA7046 |

[1] Strains carrying the uvrB mutation are deficient in excision repair of bulky lesions as measured by their lack of survival due to bulky lesions induced by $UV_{254}$ irradiation.
[2] Mutations that affect the lipopolysaccharide (LPS) component of the cell envelope: Strains carrying the galE503 mutation lack epimerase activity and therefore cannot synthesize UDP-galactose which is the donor of galactose residues for the outer core of the LPS component. Strains carrying rfa mutations have alterations in the core structure of the LPS component, which increase the cells permeability as measured by zones of inhibition of growth by crystal violet dye.
[3] The R factor is a plasmid which carries mucAB genes to compensate for the weak SOS-mediated mutagenic activities of the two umu-like operons in Salmonella.

EXPERIMENTAL

Outline of Construction of Tester Strains

In order to find histidine-requiring mutants that met the criteria described above, over 100 existing His-mutants were sequenced to identify the type and physical location of the mutations responsible for the His-phenotype. Sets I and VI were constructed on pre-existing mutants, hisG1775 (Hartman et al., 1971) and hisC9070 (Levin and Ames, 1986), respectively (See, Table 1). Although the mutations in these mutants had not been identified, hisG1775 and hisC9070 were used to make tester strains, TA4001 and TA4006, respectively, as previously reported (Levin and Ames, 1986). Over 50 specific changes were made at codons of different amino acid residues thought to be critical for enzyme activity by in vitro site-directed mutagenesis to locate targets that met the criteria for tester strain status. The mutations for Sets II, III, IV and V (Table 1) were designed and constructed on clones in vitro and transferred to the chromosome (Blum et al., 1989).

Mutations were introduced into TA4490 (hisD3052 Δara9 Δchl1004 (bio chlD uvrB chlA) galE503/pKM101; described later in this application) by P22 transductions (Zinder and Lederberg, 1952) to allow testing of both SOS-dependent and independent mutagenic agents. Revertants from mutagenicity testing of the transductants, TA704X (where X is the Set number, 1, 2, 3, 4, 5 or 6 (Table 1)), were sequenced to verify the specificity of the base substitution mutations.

DNA fragments were obtained from asymmetric amplification of freshly resuspended revertant colonies purified on minimal glucose plates (Maron and Ames, 1983) containing 3 μM biotin, by polymerase chain reaction (PCR; Saiki et al., 1988). Excess primers and buffer salts were removed from the asymmetric PCR products by Quick Spin columns (Sephadex G50 fine, Boehringer Mannheim, Indianapolis, Ind.). Sequencing primers were 5'-end labelled with $[^{32}P]$-gamma-ATP (Amersham, Arlington Heights, Ill.) using T4 polynucleotide kinase (United States Biochemical, Cleveland, Ohio). The asymmetric PCR products obtained from the revertant colonies were dideoxy sequenced using Sequenase Version 2.0 (United States Biochemical).

If the revertants were of wild type sequence at the site of the target mutation and the strain was sensitive to reversion by mutagenic agents known to make that particular base substitution mutation, then the rfa derivative of TA704X was made. The resulting derivatives were designated as complete tester strains, TA700X, and were retested with key mutagenic agents. If the rfa derivative retained sensitivity to reversion by these agents, the specificity of reversion was determined again by direct PCR sequencing.

When TA700X was confirmed to be specific for the predicted base substitution mutation, then other derivatives of the set were constructed and tested for sensitivity to reversion. The target mutations were transferred to SB8052 (hisD3052 Δara9; Hartman et al., 1971) by P22 transduction to make the series, TA701X, which carry just the target mutations without any of the additional features that enhance mutagenic sensitivity. The R factor, pKM101

(Mortelmans, 1975), was introduced into TA701X by conjugation with TA4593 (argB69/pKM101; described later in this application) to make the TA702X derivatives. The target mutations were transferred to TA2684 (hisD3052 Δara9 Δchl1004 (bio chlD uvrB chlA) galE503/pKM101; Levin and Ames, 1986) to make the TA703X derivatives (Table 1).

The target mutation was confirmed by direct PCR sequencing in each derivative in all sets of strains. Each of these strains was tested with appropriate mutagens and the specificity of a sample of revertants induced by a wide variety of mutagens was confirmed by direct PCR sequencing. Thus the reversion of each set of strains from His- to His+ by the single base substitution unique to the set, not only quantitates the potency of the mutagenic agent, but the subset of six sets of strains which responds to the mutagen indicates the molecular pathways of mutagenesis recruited by the mutagenic agent.

Construction of Recipient and Donor Strains

The intermediate strains, SB8052, TA4593 and TA4490, used in the construction of the tester strains are described below. SB8052 provided a common genetic background to all six target mutations in the his operon (Salmonella Genetic Stock Centre internal stock number SBSC2559). SB8052 has also been deposited at the American Type Culture Collection (ATCC) in Rockville, Md. and has been assigned deposit number ATCC 55480. TA4593 was constructed from TA94 (Salmonella Genetic Stock Centre internal stock number SGSC2560) and SA4757 (Salmonella Genetic Stock Centre internal stock number SA4757 because this strain designation was assigned by the Salmonella Genetic Stock Centre). TA94 and SA4757 have been deposited at the ATCC and have been assigned deposit numbers ATCC 69451 and ATCC 55481, respectively. The parents of TA4490 were TA2684 (Salmonella Genetic Stock Centre internal stock number SGSC2561) and TA4593. TA2684 has been deposited at the ATCC and has been assigned deposit number ATCC 55479. Thousands of Salmonella strains derived from the wild type typhimurium, LT2, LT7 and other less common species, and many associated bacteriophages are freely available upon request from the Salmonella Genetic Stock Centre, University of Calgary, 2500 University Drive N.W., Calgary, AB T2N 1N4, Canada. Requests are accepted by telephone, 403 220 6792; by FAX, 403 289 9311 and by electronic mail, kesander@acs.ucalgary.ca.

1. SB8052 (hisD3052 Δara9)

The mutant, SB8052 (hisD3052 Δara9) forms the basis of the recipient strains and became the genetic background of all of the subsequent tester strains of the invention. It was isolated from penicillin enrichment of mutagenesis by the non-alkylating derivative of the acridine half-mustard, ICR354-OH (2-chloro-6-methoxy-9-[2-(2-hydroxyethyl) aminoethylamino]-1-azaacridine dihydrochloride) of a stable deletion mutant, Δara9 (Oeschger and Hartman, 1970). Cells carrying the Δara9 mutation cannot grow on L-arabinose as a carbon source. The hisD3052 mutation is a deletion of a C:G base pair at position 896 of the DNA sequence of the hisD gene in the histidine biosynthetic operon so that the hisD protein is translated out of frame after $ala_{298}$. This results in a stop codon (TGA) only three amino acids downstream from $ala_{298}$ and consequently the truncated hisD protein, histidinol dehydrogenase, is inactive and the cells cannot grow on histidinol. Therefore, this mutant is phenotypically, both His- and Hol- (histidinol-).

Histidinol is the last intermediate in the biosynthesis of histidine. Thus, growth on histidinol was used as the positive selection for recombination events necessary in the transfer of His- mutations in hisG and hisC to tester strain backgrounds.

The hisD3052 mutation was mapped to the genetic regions IV-VA of the hisD gene by complementation to a set of deletion strains of the his operon (Hartman et al., 1971). No other mutations in SB8052 were found in the his operon when compared to the wild type DNA sequence (Barnes, 1981; Carlomagno et al., 1988). The nucleotide sequence of the hisD3052 mutation was derived from a comparison of the amino acid sequence of peptides from the wild type hisD gene and the revertants of SB8052 (Isono and Yourno, 1974).

The mutations, hisG1775, hisC9138, hisG9074, hisG9133, hisG9130 and hisC9070, for each of Sets I, II, III, IV, V, and VI (See Table 1), respectively, were transferred to SB8052 by transduction with the bacteriophage, P22int4 HT (Smith and Levine, 1967; Schmieger, 1972). Transductions were selected for growth on minimal 0.4% glucose plates (Maron and Ames, 1983) containing 300 μM histidinol (Sigma). These plates were incubated at 37° C. for 36 to 48 h. Fifteen to twenty transductants were picked and purified for single colony isolates on nutrient agar plates (Maron and Ames, 1983) and incubated at 37° C. for 24 h to check for P22 lysogens. A healthy medium size colony from each original transductant was tested for a His-, Hol+ phenotype. Colonies which appeared to have a concentric ring on the surface to give a donut-like appearance were suspected to be P22 lysogens, and the largest colonies were often tested to be of wild type phenotype in both hisG or hisC and hisD (His+Hol+). Of the His-Hol+ isolates, one isolate was chosen for a fast growth rate, a low spontaneous reversion frequency and a high sensitivity to SOS-independent mutagens and designated TA701X.

2. TA4593 (argB69/pKM101)

TA4593, an arginine auxotroph, is the donor strain in this study for pKM101, which confers ampicillin resistance to the recipient. In addition to the β-lactamase gene which is responsible for ampicillin resistance, the R factor, pKM101 (Mortelmans, 1975), also carries the mucAB genes.

The fidelity of DNA repair in the bacterial cell is thought to be compromised by inducing the mucAB genes (muc: mutagenesis: UV and chemical; Langer et al., 1981; Perry et al., 1982; and Elledge et al., 1983), which code for a very active SOS system. These genes are induced when damage to the DNA blocks replication and/or transcription. Elevated concentrations of these SOS-related proteins enhance the misincorporation of bases and/or allows the polymerases to bypass the DNA lesion.

Three different mutants, ΔpyrE125 (Turnbough and Bochner, 1985), argB69 and argD10 (Demerec et al., 1960) were considered for constructing a donor strain for the R factor, pKM101, to replace TA2000 (McCann et al., 1975) which was used in the construction of previous Ames strains. TA2000 (purF145/pKM101) was constructed by transferring pKM101 from SL3379 (Mortelmans et al., 1975) to purF145 (TR6770, Downs and Roth, 1987). It was suspected that TA2000 was carrying a cryptic prophage that was defective in some way since its release as a plaque-forming particle was not predictable and was transferred to some of our strains. Inconsistently, about ten or less very faint plaques were observed on a lawn of cells during mutagenicity testing. Induction of these plaques was not reproducible when testing was repeated using the same testing components. Further, plaque formation could not be enriched by plating the actual culture used for testing on rich medium. This indicated that neither the bacterial culture nor the reagents used during the testing was contaminated with an exogenous bacteriophage. However plaques were observed only when the strain used for testing had been constructed with TA2000 as an intermediate derivative.

Furthermore, TA2000 was used as the donor of pKM101 in the construction of all Salmonella tester strains from 1975 (McCann et al., 1975) including the widely distributed strains, TA97a, TA98, TA100, TA102, TA104 (Maron and Ames, 1983) and more recently, TA4001 and TA4006 (Levin and Ames, 1986). However there have been no reports of plaque formation in any of these strains by any of the numerous labs who use these strains routinely for mutagenicity testing. The variability in the mutagenic response between experiments and between laboratories (Kier et al., 1986; Agnese et al., 1984; Grafe et al., 1981) may be a result of unpredictable plaque formation which may have escaped observation.

Using TA92 (hisG46/pKM101; TA92=SL3379; McCann et al., 1975) as the donor, pKM101 was transferred to ΔpyrE125 (Turnbough and Bochner, 1985) to construct TA4488. This strain failed to eliminate plaques. However, using this strain as the pKM101 donor only made a slight improvement in the robustness of the completed tester strain. Further, fewer faint plaques were observed, and these appeared less frequently during testing of the same strains. No consistent pattern of release of plaque-forming particles was found with a given mutagen or a particular derivative or a set of strains. Since the histidine biosynthetic pathway uses ATP and PRPP as the initial substrates, it is tied into intermediary metabolism of the purines, pyrimidines, pyridines and tryptophan. It has been shown that when the mutant, purF145 (the mutation carried in TA2000 as the basis of selection for conjugation), is starved for purines, plaques sometimes form but not consistently (Downs and Roth, 1987). Theoretically, only the episome should be transferred during conjugation for which the R factor donor strains are used and not any of the markers associated with the purF145 or ΔpyrE125. However, it appears that episome transfer sometimes included a factor that is associated with induction of phage particles.

Both the possibility of carrying cryptic prophage(s) and the conditions that might predispose the induction of prophage particles were minimized to avoid compromising cell growth and its mutagenic response. As histidine biosynthesis is known to be related to biosynthesis of the nucleotides and some amino acids, two mutants, argB69 and argD10 (Demerec et al., 1960) were chosen because arginine biosynthesis is not affected by histidine biosynthesis. Other mutants such as SA2841 (trpC2) and SA1117 (metA22) (Sanderson and Stocker, 1987; Salmonella Genetic Stock Centre, internal stock numbers SA2841 and SA1117), respectively, may also have suitable auxotrophies for the construction of a donor strain for pKM101.

ArgB69 was chosen as the faster growing mutant on rich nutrient agar plates and was assigned the strain designation, SA4757 (Salmonella Genetic Stock Centre, argD10 is available at the Salmonella Genetic Stock Centre but was not assigned a strain designation). Two single colony isolates of SA4757 were picked and reisolated on minimal 0.4% glucose plates containing 0.6 mM arginine. A single large colony was picked and grown overnight (12 h) in a shaking incubator at 37° C. A 100 µl aliquot of the freshly grown culture of SA4757 was spotted in the center of a minimal 0.4% glucose plate. A 10 µl aliquot of fresh overnight culture of TA94 (hisD3052/pKM101, Haroun and Ames, 1977; Salmonella Genetic Stock Centre internal stock number SGSC2560) was spotted immediately on top of SA4757. A mixture of 95 µl ampicillin (16 mg/ml with final plate concentration of 50 µg/ml) and 125 µl arginine (145 mM with final concentration of 0.6 mM) was added and all were spread immediately until the liquid was absorbed by the plate. This was incubated for 24 h at 37° C. along with control plates which were prepared in the same manner except TA94 was left out in one and SA4757 was left out of another. There was no growth on either control plate since TA94 cannot grow without histidine and SA4757 was not resistant to ampicillin. Six isolates were picked from different areas of confluent growth and were streaked for single colony isolates twice on minimal 0.4% glucose plates containing 0.6 mM arginine and 50 µg/ml ampicillin. A large single colony was chosen and designated TA4593 (argB69/pKM101). TA4593 was used as the donor of pKM101 for all the TA7000 series strains (See Table 1) and there has been no reoccurrence of plaque formation.

3. TA4490: hisD3052 Δara9 Δchl1004 (bio chlD uvrB chlA) galE503/pKM101

Other mutations which compromise repair of damaged DNA include mutations that affect the excision of bulky adducts which distort the alpha-helical structure of DNA. These mutations include a complete deletion of the uvrB gene (uvr: WV repair) which directs the bulky excision repair complex, (uvrA$_2$BC$_2$) to the specific location of the DNA adduct formed by agents like UVC irradiation or 4-nitroquinoline-1-oxide (NQNO). Thus a deletion of uvrB increases the concentration of pre-mutagenic lesions to enhance the probability of a mutation in response to the lesion instead of its removal.

Mutations that increase cell membrane permeability to mutagens also increase the sensitivity of cells to mutagens. The point mutation, galE503 (HN202, M1, Fukasawa and Nikaido, 1961; Salmonella Genetic Stock Centre internal stock number SGSC2563) is sufficient to inactivate the UDP-galactose-4-epimerase which prevents the utilization of galactose as a carbon source and renders the cell susceptible to lysis from UDP-galactose when galactose concentrations are too high in the growth medium. Also, the lipopolysaccharide of the outer membrane lacks all sugars distal to the first glycosyl residue (Rick, 1987). Other point mutations such as galE496 (SL1657) and galE856 (LB5010) (and smaller deletions in the gal operon) are available from the Salmonella Genetic Stock Centre under their strain designation SL1657 and LB5010, respectively. They may prove to be as suitable as galE503 (HN202) but this mutation was used in the selection of rfa mutations because it had been well characterized.

Similarly, over 1500 mutations are available in the rfa operon (which consists of nine genes) that result in 'rough' appearing colonies as compared to smooth wild type colonies. Isolates with mutation(s) in the rfa operon were selected on the basis of best growth (doubling time of about 30 min) and permeability to the high molecular weight dye, crystal violet. Permeability to crystal violet is measured by the size of the zone of growth inhibition of the rfa mutant by crystal violet and simulates the accessibility of large test compounds for the purposes of mutagenicity assay. Mutations in the rfa operon are believed to play a pivotal role in determining whether a given concentration of chemical is toxic enough to induce the SOS response and undergo mutagenesis, or is so toxic as to kill or arrest the growth of the cell, which prevents mutagenesis. Thus the rfa mutation may contribute to the sensitivity of the strains in the detection of some mutagenic agents like N4OHC when tested on TA7001 as represented by the hatched bar (right side of graph), which is the rfa derivative of TA7041 as represented by the solid bar (left side) in FIG. 3. Or the rfa mutations may detract from the sensitivity of the strains in the detection of other mutagenic agents like NQNO when tested on TA7004as represented by the hatched bar (right side), which is the rfa derivative of TA7044 as represented by the solid bar (left side) in FIG. 7.

Each of the mutagenicity enhancing features have been optimized to increase the sensitivity of the present strains with the least effect on the growth rate of the resulting strain. For example, hisG9074, the mutation of Set III was transferred into a genetic background where a large deletion removed a substantial part of the gal operon (galE, galT, galK; TA4338) which is mapped to 18 min of the Salmonella genetic map (Sanderson and Hurley, 1990). This deletion extends past uvrB to include chlA which is more than 0.6 min away on the genetic map. This constitutes approximately 28 kbp of DNA. In this genetic background, the hut operon (histidine utilization genes); glnp, (high affinity glutamine transporter); bio, (biotin synthesis); chlD and chlA which is responsible for resistance to chlorate were deleted in addition to the deletion which inactivated gal and uvrB. TA4338 (hisG9074 Δchl1043 (gal hut glnP bio chlD uvrB chlA) rfa/pKM101) was made to optimize the contributions of mutations in gal and uvrB. Since this deletion was so large, these genes would not be recovered by reversion and these secondary characteristics would be very stable, however, TA4338 was not as sensitive as the current Set III strains which carry a smaller deletion that starts at bio and extends through chlD, and uvrB, and ends in chlA.

Using TA4593, pKM101 was transferred to TA2684 (hisD3052 Δara9 Δchl1004 (bio chlD uvrB chlA) galE503; Levin and Ames, 1986) by conjugation. A 10 μl aliquot of a fresh overnight culture of TA4593 was placed on top of 100 μl of a similar culture of TA2684 and spread on a minimal 0.4% glucose plate (Maron and Ames, 1983) containing 260 μM histidine, 3 μM biotin and 50 μg/ml ampicillin. Conjugate cells were picked from six different areas of confluent growth and streaked for single colony purification on plates used in the original selection. Six isolates were repurified and the fastest growing isolate that tested His–Hol+, and resistant to ampicillin was designated TA4490 (hisD3052 Δara9 Δchl1004 (bio chlD uvrB chlA) galE503/pKM101.

TA4490 was used as the recipient strain in the first step of strain construction because it allowed the testing of both SOS-dependent and independent mutagenic agents. The mutations in hisG and hisC for each of Sets I to VI were transferred to TA4490 by P22 transduction to growth on minimal 0.4% glucose plates (Maron and Ames, 1983) containing 300 μM histidinol, 3 μM biotin and 50 μg/ml ampicillin. These plates were unincubated at 37° C. for 36 to 48 h. Fifteen to twenty transductants were picked and purified for single colony isolation on nutrient agar plates (Maron and Ames, 1983) and incubated for 24 h at 37° C. A healthy medium size colony from each original transductant was tested for a His+Hol+ phenotype. Of the His+Hol+ isolates, one was chosen according to a high growth rate on histidine; and a low spontaneous reversion frequency in the absence of histidine and a high degree of inducibility by SOS-dependent and independent mutagens and designated TA704X.

Validation of Tester Strains

1. Set I Strains: A:T→G:C Transitions (a) Target mutation: hisG1775

The codon for Set I was found by sequencing the pre-existing mutant, hisG1775, which was isolated from N-methyl-N'-nitro-N-nitroso-guanidine (MNNG) mutagenesis and enriched by penicillin selection (Hartman et al., 1971).

The type and location of the mutation in the pre-existing, hisG1775 mutant was identified as:

$$\text{asp}_{153}$$
5'-GT CTG TTA AAT GAT TCT GTC-3' (mutant)
(SEQ ID NO: 5)

5'-GT CTG TTA AAT GGT TCT GTC-3' (wild type)
$$\text{gly}_{153}$$ (SEQ ID NO: 6)

(See, FIG. 1) where the middle G in the $\text{gly}_{153}$ codon had been replaced with an A, so that the reversion to wild type requires a A:T to G:C transition.

TA4071 (hisG1775 supE zbf98::Tn10/F42 finP301 lac$^+$) was constructed by mating hisG1775 with SA2197 (purC7/F42 finP301 lac$^+$; Sanderson et al., 1981; Salmonella Genetic Stock Centre internal stock number SA2197) and rendered supE by P22 transduction with TT2342 (supE zbf98::Tn10 hisC527 leu-414; Johnston and Roth, 1981) to allow for infection by M13 bacteriophage. The hisG1775 mutation of TA4071 was transferred to the clone, M13mp9::his4 (Artz et al., 1983), which has a deletion in the region homologous to the hisG1775 mutation. Recombinant phage were purified and single stranded DNA was prepared for single stranded M13 dideoxy sequencing. The hisG1775 mutation was identified to be a G:C to A:T transition where $\text{asp}_{153}$ (GAT) has replaced the wild type, $\text{gly}_{153}$ (GGT). This single mutation was responsible for the histidine requirement of hisG1775. Although three other pre-existing mutants, hisG72, hisG1769 and hisG1792 (Hartman et al., 1971), were found to carry an identical $\text{asp}_{153}$ (GAT) mutation at $\text{gly}_{153}$ (GGT), hisG1775 was selected because some mutagenicity data were available (Levin and Ames, 1986).

(b) Construction of TA7011, TA7021, TA7031, TA7041 and TA7001

The high frequency transducing phage, P22int4HT, was grown on hisG1775 and phage lysate carrying this mutation was used to transduce TA4490. The transductant was selected for growth on histidinol, and designated, TA7041 (hisG1775 Δara9 Δchl1004 (bio chlD uvrB chlA) galE503/pKM101). It was checked for His–Hol+ phenotype and was PCR sequenced to verify the transfer of the mutation. TA7041 was screened for resistance to lysis by bacteriophage C21 (Wilkinson et al., 1972) to select for its rfa derivative, TA7001 (hisG1775 Δara9 Δchl1004 (bio chlD uvrB chlA) galE503 rfa1041pKM101) which constitutes the complete tester strain. Other derivatives carrying different repair and mutagenic enhancing features, TA7011 (hisG1775 Δara9) and TA7031 (hisG1775 Δara9 Δchl1004 (bio chlD uvrB chlA) galE503), were made by P22 transduction of the hisG1775 mutation to SB8052, and TA2684 (Levin and Ames, 1986), respectively (Table 1). The R factor, pKM101, was introduced to TA7011 by conjugation with TA4593 to make TA7021 (hisG1775 Δara9/pKM101) (Table 1).

(c) Mutagenicity Testing: Sensitivity of Reversion of Set I

Although all derivatives were tested, TA7001 was tested extensively as represented by the hatched bars in FIG. 3, instead of TA7041 as represented by the solid bars in FIG. 3 because it was desirable to check that the addition of the rfa1041 mutation did not decrease the mutagenic response by more than about 50% for compounds such as N[4]-aminocytidine (N4amC). The plate incorporation assay (Maron and Ames, 1983) was used with only a minor modification. The concentration of glucose in the agar plates was decreased from 2% to 0.4%. Both methyl glyoxal (meGl) and formaldehyde (form) were preincubated with TA7001 for 20 min before plating. Revertant colonies of TA7041 and TA7001 were counted after 48 h incubation and purified on minimal 0.4% glucose plates containing 3 μM biotin and single colonies were picked for sequencing. Derivatives of Set I responded very well to N4amC mutagenesis, so N4amC was chosen as the positive control mutagen for Set I strains. N4amC induced 2120±35 revertants per plate when tested with TA7041 and 990±55 revertants per plate when tested with TA7001, the complete tester strain carrying the rfa1041 mutation. These data are included in Table 2 but are not included in FIG. 3 because the scale would have been so large as to obscure data obtained from other mutagenic agents. Strains for Set I responded well to an appropriate subset of the different mutagenic agents tested and have met the sensitivity criteria as tester strains (FIG. 3).

(d) Verification of Reversion Specificity of Set I

Revertants induced by different mutagens were suspended in sterile water ($10^{17}$ ohms resistivity) and whole cells were used as templates for 40 cycles of asymmetric PCR using primer ratios of 1:100. DNA obtained was sequenced directly using a $^{32}$P-end-labelled primer. Over 100 independent, spontaneous revertants and mutagen-induced revertants, from the mutagens set forth in FIG. 3, were sequenced and found to have only the wild type sequence, GGT; therefore, this mutant codon reverts specifically by A:T to G:C transitions. About 10 revertants induced by N[4]amC were sequenced from each representative strain from Set I (i.e., TA7001, TA7011, TA7021, TA7031 and TA7041; see, Table 1) to confirm that the mutagen chosen as the positive control for these strains induced specifically A:T to G:C base changes in all derivatives of the hisG1775 mutation.

(e) Comparison of Set I strains with TA4011 and TA4001

Although hisG1775 was assumed to be a C:G to T:A transition (Hartman et al., 1971), the location and the type of this mutation was not identified until hisG1775 was sequenced. It was confirmed to be G:C to A:T by sequence analysis. Both of these changes are classified as Set I since only the DNA strands are inverted; it was decided to name the sense strand of the actual mutation first. This mutation was carried in the previously described tester strains, TA4001 (hisG1775 galE503ΔuvrB bio chl1004 rfa1031/pKM101) and TA4011 (hisG1775) which were presumed to revert specifically by T:A to C:G transitions (Levin and Ames, 1986). Approximately 40 independent spontaneous and mutagen induced revertants of TA4001 and TA4011 were sequenced in the course of the present study to verify that the specificity of reversion was of wild type sequence only. This sequencing was undertaken because although assumptions are made in the art regarding the type and specificity of reversion of mutations in Salmonella mutant strains, as many as 50% of such assumptions tested by DNA sequencing were found to be incorrect.

For example, of the 4 mutants that were identified by the system of Levin and Ames (1986), to revert by specific base mutations, 2 mutants, hisC9072 and hisA9071 (unpublished), did not revert by single, and specific base substitutions. hisC9072 was thought to revert only by T:A to G:C transversions (Set III strains) because it reverted exclusively to ang/UVA and not to tBHP. The mutation was determined to be $lys_{214}$ (AAA) in place of the wild type $thr_{214}$ (ACA) by direct PCR analysis. However sequence analyses of both mutagen induced and spontaneous revertants revealed that only 57% were reverting by the expected A:T to C:G transversion (equivalent to Set III strains) of which only 14% were to the wild type thr (ACA) and the other 43% were to $asn_{214}$ (AAC). The remaining 43% reverted by A:T to T:A transversions also to $asn_{214}$ (AAT). The mutation in the other mutant, hisA9071, was thought to revert by C:G to T:A transitions (equivalent to Set IV strains) because it responded very well to MNNG and not much else. The mutation was identified to be a $pro_{16}$ (CCC) in place of $leu_{16}$ (CTC). From both mutagen-induced and spontaneous revertants, 45% reverted by C:G to T:A transitions to wild type $leu_{16}$ (CTC), but 36% reverted by C:G to A:T transversions to $his_{16}$ (CAC) and the remaining 19% retained the mutant sequence, CCC for $pro_{16}$ which was indicative of missense suppression.

TA4001 and TA4011 were reisolated and tested with several mutagens in addition to those already reported (Levin and Ames, 1986). Although TA4001 reverted specifically to wild type sequence, it was not sensitive enough to be useful because its average reversion rate was not even 5±1 times let alone 10 times greater than the spontaneous frequency when treated with approximately 20 mutagenic agents (See, FIG. 4). TA4001 is represented by the open bars in FIG. 4. The complete tester strain, TA4001 did not show the requisite sensitivity for inclusion in Set I. (In contemplating an acceptable level of sensitivity it should be noted that usually a 10 fold above background sensitivity is considered a minimal detection limit in a measurement system.) Therefore, a new set of strains, designated TA70X1, were constructed for Set I.

As reversion of TA4001 and TA4011 was specific, the mutant allele, hisG1775 was retained in the construction of strains in Set I (TA7001, TA7041, TA7031, TA7021 and TA7011) using the herein described novel recipient and donor strains. Construction of Set I strains using TA4593 and TA4490 resulted in strains that are more genetically stable and were sensitive to mutagenic agents. No plaque formation has been observed during the extensive testing of all representative strains of Set I.

Treatment of hisG1775 with N4OHC was reported to induce 135 revertants per plate with a spontaneous frequency of 1 revertant per plate (Table IV in Levin and Ames, 1986). TA4001, the complete tester strain carrying the rfa1031 mutation, was previously derived from hisG1775, but no values were reported for N4OHC (Levin and Ames 1986). However, when TA4001 was tested in the course of the present study, only 21±2 revertants per plate with N4OHC were obtained. By comparison, the equivalent representative strain from Set I, TA7001 (rfa1041), was reverted at 166±21 per plate by N4OHC. Therefore, TA7001 (as represented by the hatched bars in FIG. 4) was approximately 8 fold more sensitive than TA4001 (as represented by the open bars in FIG. 4), to N4OHC, since the Levin and Ames 1986 spontaneous reversion rates were very similar (2.5 and 2 revertants per plate respectively). A standard number of $8\pm4\times10^8$ cells per plate was always used in the present studies as well as in the 1986, Levin and Ames study to test the induction of reversion by mutagenic agents as detailed in Maron and Ames (1983).

Streptonigrin (Strgn), a bulky agent that requires the presence of a rfa mutation for maximal induction was found to induce 13±1 revertants per plate in TA4001 as compared to 103±19 revertants per plate in TA7001. These represent sensitivity ratios of less than 7 for TA4001 and greater than 40 for TA7001. The present study repeated the testing of TA4001 with to angelicin/UVA (ang/UVA) to obtain 14±1 revertants per plate which was the same as the published value of 14 revertants per plate (Levin and Ames, 1986). By comparison, 60±4 revertants were induced in TA7001, which is greater than 20 fold over spontaneous. Furthermore, TA7001 was induced to a greater extent by all mutagenic agents tested when compared to TA4001 (See FIG. 4). For TA7001, the average of the sensitivity ratios for the 18 mutagens tested was about 14 and the individual ratios ranged from 0.3 to 66 fold over spontaneous; as compared to an average of only 2.7 with ratios ranging from 0.3 to 11 fold over spontaneous reversion rates for TA4001. This was critical for mutagenic agents that induced A:T to G:C transitions only weakly such as tBHP, 2NF, BUdR and 2AP because they were not detected by TA4001.

2. Set II Strains: T:A→A:T Transversions (a) Target Mutation: hisC9138

More than 50 separate classical and in vitro mutagenesis experiments were conducted to find a suitable candidate that reverted by T:A to A:T transversions. None of the enzymes in the Salmonella histidine biosynthetic operon have been crystallized, including the enzyme, histidinol-phosphate aminotransferase which is coded by the hisC gene. However, Mehta et al. (1989) aligned the E. coli histidinol-phosphate and aspartate aminotransferases with 21 vertebrate mitochondrial and cytosolic aminotransferases to find 12 invariant amino acid residues. Based on the crystal structure of aspartate aminotransferase from E. coli, one of these 12 invariant amino acids, a lysine residue, was determined to be responsible for binding the cofactor, pyridoxal phosphate (Kamitori et al., 1990). While there was less than 20% amino acid sequence identity between aspartate and non-aspartate aminotransferases, there was 86.9% amino acid homology between the E. coli histidinol-phosphate aminotransferase and the S. typhimurium histidinol-phosphate aminotransferase (Carlomagno et al., 1988). After careful analysis of these two sequences, $lys_{217}$ in hisC (See FIG. 2) of the S. typhimurium enzyme was chosen as the target site of in vitro mutagenesis.

In order to work in the hisC gene, it was necessary to construct clones that contained hisC and strains that would serve as recipients of the genetically engineered mutations and serve in complementation assays for expression of the clones carrying hisC. The male-specific F plasmid was transferred from SA2197 (Sanderson et al., 1981) to TA812 Δhis129 (hisDC) (Hartman et al., 1971) to make the recipient strain, TA4302 (Δhis129 (hisDC)/F42 finP301 lac$^+$) which allowed its infection by male-specific M13 clones. Strain TA4302 has been deposited at the ATCC and has been assigned deposit number ATCC 55482. TA4303 (Δhis129 (hisDC) supE zbf::Tn10/F42 finP301 lac$^+$), a supE derivative of TA4302, was made by P22 transduction with TT2342 (Johnston and Roth, 1981). The endpoints of the deleted region in TA4302 were determined by direct PCR sequence analyses. The 5' endpoint of the deletion started in the hisD gene such that enough was deleted to render TA4302 Hol– and extended through almost 80% of hisC including the region that corresponded to the $lys_{217}$ codon.

The structural genes of hisD and hisC were excised sequentially with NarI and EcoRV from PHS10000 (Carlomagno et al., 1983) which had been propagated in the E. coli strain, TA4308 (Δhis416 (hisOGDCBGHAFIE)/F42 finP301 lac$^+$). TA4308 has been deposited at the ATCC and has been assigned deposit number ATCC 69450. The 692 bp fragment was restricted further with HindIII to yield a 498 bp HindIII to EcoRV fragment, which, together with a 2210 bp EcoRV to NarI fragment, was subcloned into the bacteriophage, M13mp8, using the HindIII and AccI sites of the polylinker (Boehringer Mannheim) to construct the clone, M13mp8::hisDC1. This included approximately 225 bp of the hisB gene downstream from hisC at the 3' end of the insert and 150 bp of the hisG gene 5' to the hisD gene. The flanking regions provided sufficient overlap on both sides of Δhis129 for homologous recombination into TA4302. The hisD gene was included as the selectable marker for growth on histidinol and is the adjacent gene upstream of hisC which provided a continuous fragment to complete the deleted region in TA4302. M13mp8::hisDC1 was able to complement both Δhis129(hisDC) in TA4303 and hisD3337 in AZ1457 (Artz et al., 1983) to His+Hol+. Therefore, the hisD and hisC genes in the clone, M13mp8::hisDC1, were expressed correctly.

The codon for $lys_{217}$ (AAA) of hisC was changed to $ile_{217}$ (ATA) using PCR to generate a DNA fragment to fix the mutation which was synthesized in a 22 bp oligomer. The sequence of the single-stranded 22-bp DNA oligomer which contained the mutation for hisC9138 was made in the sense strand:

$ile_{217}$
5'-CGC ACA TTG TCG <u>ATA GCT TTT</u> G-3' (mutant)
(SEQ ID NO: 7)

5'-CGC ACA TTG TCG AAA GCT TTT G-3' (wild type)
$lys_{217}$ (SEQ ID NO: 8)

The middle A of the $lys_{217}$ codon was changed to a T, and the reversion of the $ile_{217}$ mutant to lysine requires a T:A to A:T transversion. The underlined sequences indicate the actual DNA oligomer that was synthesized to introduce the target mutation.

This synthetic 22 bp DNA oligomer was used to generate a DNA fragment by PCR that was subcloned into the clone, M13mp8::hisDC1. The subsequent $ile_{217}$ clone was found to be His+ and Hol+. This indicated that changing lys to ile was sufficient to inactivate the histidinol-phosphate transferase coded by hisC to the extent that it would no longer support growth without histidine. The ile mutation was then transferred to the chromosome of TA4302 by M13 transduction (Blum et al., 1989) using histidinol selection. The transductant was cured for lysogeny and was designated the mutant allele, hisC9138 (See, Table 1). P22int4HT was grown on this transductant and the resulting phage lysate, (P22int4HT::hisC9138) was used to carry the $ile_{217}$ (ATA) mutation into tester strain backgrounds.

(b) Construction of TA7012, TA7022, TA7032, TA7042 and TA7002

Construction of tester strain derivatives of Set II followed strategies similar to those used for Set I (Table 1). TA7042 (hisC9138 Δara9 Δchl1004 (bio chlD uvrB chlA) galE503/pKM101) was made by P22 transduction of hisC9138 to TA4490 by selection on histidinol. TA7002 (hisC9138 Δara9 Δchl1004 (bio chlD uvrB chlA) galE503 rfa1042/pKM101) was isolated by resistance to lysis by C21. TA7012 (hisC9138 Δara9) and TA7032 (hisC9138 Δara9 Δchl1004 (bio chlD uvrB chlA) galE503) were constructed by P22 transduction into SB8052 and TA2864 respectively and TA7022 (hisC9138 Δara9/pKM101) was made from conjugation of TA7012 with TA4593.

(c) Mutagenicity Testing: Sensitivity of Reversion of Set II

Primarily, TA7042 (represented by the solid bars in FIG. 5, left side) and TA7002 (represented by the hatched bars in FIG. 5, right side) were tested using the standard plate incorporation assay (Maron and Ames, 1983) to characterize the reversion pattern of hisC9138 with the exception of meGl, form and chlorambucil (CB1348). These last three mutagenic agents were preincubated for 20 min before plating. In addition to the 20 min of liquid preincubation at 37° C. (Maron and Ames, 1983) to optimize induction by t-butyl hydroperoxide (tBHP) and cumene hydroperoxide (CHP) the Set II representative strain, TA7022, was used as shown in FIG. 14. 40 μg of tBHP and CHP per plate induced the reversion of TA7022, 14 and 16 fold above spontaneous frequencies for tBHP (hatched bar, FIG. 14) and CHP (stippled bar, FIG. 14), respectively. This can be compared to about three and two times above spontaneous frequencies, respectively, in the standard plate incorporation assay for TA7042 and TA7002 as seen in FIG. 5. The reversions of both TA7042 and TA7002 were induced by angelicin mutagenesis after $UVA_{(320-400\ nm)}$ activation (ang/UVA) at a frequency greater than 200 times above the background (FIG. 5). Therefore, $UVA_{(320-400\ nm)}$/angelicin was chosen as the positive control for strains in Set II.

The mutagenic agent, angelicin activated by $UVA_{(320-400\ nm)}$ irradiation, required some preparation before cells are plated in the standard plate incorporation assay. The tester strains, TA7002 in this example, is grown overnight (12 h) in oxoid broth as indicated in Maron and Ames (1983). However 5.5 ml of this culture is centrifuged at 1080×g for 10 min. The broth is removed to prevent confounding effects from UVA irradiation of components in the broth. The cell pellet is resuspended in 1×VBC (Maron and Ames, 1983) to a concentration comparable to the original overnight culture as measured by absorbance at 650 nm. 7.5 μl of angelicin (200 μg/ml) was added to 1.5 ml of cell suspension and shaken at 37° C. for 30 min. This mixture is transferred to a petri dish (60×15 mm) and placed on a gently rotating platform to facilitate uniform irradiation, 10 cm from a near-UV light source (Gates-Raymaster from Thomas, Philadelphia, Pa.) which has a UVA spectrum of 320 to 400 nm. The dose at 10 cm from the light source is measured at 4.6 J/m²/s. An exposure of 7.5 min results in a dose of 5.9±0.1 J/dish. Control plates included cells that were exposed to UVA only or to angelicin without UVA activation. 100 μl of this mixture was plated as in the standard plate incorporation assay (Maron and Ames, 1983). All mutagenesis experiments using the mutagenic agent, ang/UVA, were standardized to 0.1 μg ang and 0.39±0.01 J/plate.

(d) Verification of Mutagenic Specificity of Set II

A sampling of independent revertants were obtained from each mutagenic agent (See, FIG. 5) and resuspended for asymmetric PCR and subsequently sequenced in much the same fashion as the revertants obtained from Set I. Only the wild type sequence was found in over 100 revertants sequenced. Thus the mutation $ile_{217}$ (ATA) reverts specifically at the target codon by T:A to A:T transversions to $lys_{217}$ (AAA).

In summary, the $ile_{217}$ mutation introduced in place of wild type $lys_{217}$ inactivated the enzyme sufficiently to inhibit growth, and reversion of the strains built on this hisC9138 mutant allele was specifically by T:A to A:T transversions only. Further, the $ile_{217}$ mutants were sensitive to mutagenic agents which specifically induce T:A to A:T mutations.

3. Set III Strains: T:A→G:C Transversions (a) Target Mutation: hisG9074

The target mutation of Set III strains (Table 1) was based on the mutant codon identified for hisG1775. The base change, G:C to T:A, was constructed by in vitro site-directed mutagenesis in which $gly_{153}$ (GGT) of hisG (FIG. 1) was replaced by $val_{153}$ (GTT). This mutation was synthesized in a 20 bp DNA oligomer and was used to prime a single stranded template of M13mp9::his1 (Artz et al., 1983).

The sequence of the 20 bp DNA oligomer which carried the mutation for hisG9074 was synthesized in the antisense strand:

5'-GAC AGA AAC ATT TAA CAG AC-3' (SEQ ID NO:9)

The sense strand is shown as its reverse complement. The oligomer is the bottom strand:

$gly_{153}$
5'-GT CTG TTA AAT GGT TCT GTC-3' (wild type)
(SEQ ID NO: 6)

3'-CA GAC AAT TTA CAA AGA CAG-5' (mutant)
(SEQ ID NO: 9)

T was inserted in the top or sense strand opposite the A in the bottom strand in subsequent rounds of replication and was fixed as GTT which was translated as valine:

$val_{153}$
5'-GT CTG TTA AAT GTT TCT GTC-3' (mutant)
(SEQ ID NO: 10)

5'-GT CTG TTA AAT GGT TCT GTC-3' (wild type)
$gly_{153}$ (SEQ ID NO: 6)

The $val_{153}$ mutant reverts to wild type $gly_{153}$ by a T:A to G:C transversion.

The mutant clone was enriched by methods as described by Kunkel et al. (1987) with some minor modifications. The $val_{153}$ mutation was transferred to the chromosome by M13 transduction (Blum et al., 1989) and assigned the allele number, hisG9074. Although no pre-existing $val_{153}$ (GTT) mutants were found, three alternate Set I mutants, $ser_{153}$ (AGT), hisG8643, hisG3048 and hisG3085 (Hartman et al., 1971), were found using direct PCR sequencing.

(b) Construction of TA7013, TA7023, TA7033, TA7043 and TA7003

The mutation, hisG9074, was transferred to TA4490 by P22 transduction using histidinol selection. Transductants were single colony isolated and the fastest growing isolate was designated TA7043 (hisG9074 Δara9 Δchl1004 (bio chlD uvrB chlA) galE503/pKM101). The rfa derivative, TA7003 (hisG9074 Δara9 Δchl1004 (bio chlD uvrB chlA) galE503 raf1043/pKM101), was isolated from resistance to lysis from bacteriophage, C21 (Wilkinson et al., 1972). To construct the remaining derivatives, the mutation, hisG9074 was transferred to SB8052 and TA2864 by P22 transduction to make TA7013 (hisG9074 Δara9) and TA7033 (hisG9074 Δara9 Δchl1004 (bio chlD uvrB chlA) galE503), respectively; while TA7023 (hisG9074 Δara9/pKM101) was made by conjugation with TA4593 (Table 1).

(c) Mutagenicity Testing: Sensitivity and Specificity of Reversion of Set III

Although the $val_{153}$ (GTT) mutation in all strains of Set III reverted at a spontaneous frequency of less than one colony per plate (from one colony in two to ten plates, Table 2), the conservative estimate of one colony per plate ($8\times10^8$ cells/plate) was used to determine sensitivity or responsiveness of strains based on this mutation. The mutagenic agent, angelicin/UVA was selected as the positive control for the strains of Set III. This agent induces reversion approximately 150 times, for TA7043 (as represented by the solid bars in FIG. 6), and about 190 times, for TA7003 (as represented by the hatched bars in FIG. 6), above their respective spontaneous frequencies. As in Set II, meGl, form and CB1348 were preincubated for 20 min before plating. Although not shown in FIG. 6, low levels of mutagenicity were detected on using t-butylhydroperoxide (tBHP; hatched bars) and cumene hydroperoxide (CHP; stippled bars) at about five times above spontaneous frequencies for TA7023 when tested with 20 min of liquid preincubation (Maron and Ames, 1983) before plating (FIG. 14).

Set I responded to mutagens such as N4OHC and N4amC which are known to cause A:T to G:C transitions but do not cause T:A to G:C transversions. As expected, neither TA7043 nor TA7003 was reverted by these mutagens, as N4OHC and N4amC, do not induce T:A to G:C transversion. On the other hand, mutagenic agents like ang/UVA were capable of inducing primarily T:A to G:C transversion (FIG. 6), but also T:A to A:T transversions (FIG. 5), and to a lesser extent, A:T to G:C transitions (FIG. 3) and C:G to G:C transversions (FIG. 10).

(d) Verification of Reversion Specificity of Set III

Revertants were chosen from each of the mutagens tested (FIG. 6) and were resuspended for asymmetric PCR and sequenced as in previous sets. Over 100 independent revertants of TA7043 and TA7003 resulting from the mutagenicity assays as depicted in FIG. 6 were sequenced and found to be of only wild type sequence, thereby confirming the specificity of the T:A to G:C transversions in the reversion of strains in Set III.

4. Set IV Strains: G:C→A:T Transitions (a) Target Mutation: hisG9133

Strains in Set IV and Set V were constructed by base substitution in a non-wobble site of a codon in which the wild type wobble site was altered to enhance the precision of reading by tRNA at the mutated codon. While much is known about the context parameters that govern the efficiency of translation (Maden, 1993; Sorensen and Pederson, 1991; Shpaer, 1986; Bossi and Roth, 1980) in relation to evolutionary and species bias of codon selection (Osawa et al., 1990), there is no known coupling factor(s) to suggest that increased efficiency of translation affects a target of mutagenesis. Mutant suppressor tRNA species have been used to study the effects of codon context on the efficiency of suppression of nonsense and missense mutations (Pages et al., 1991; Maldonado-Rodriguez et al., 1991; Buckingham, 1990; Buckingham et al., 1990(a); Tucker et al., 1989; Murgola et al., 1984; Winston et al., 1979; Simarov et al., 1971) and in some cases where sufficient detail is known (Sledziewska-Gojska et al., 1992; Levin and Ames, 1986), suppressor tRNA species have been used to imply mutagenic specificity.

The target mutation for Set IV was indirectly based on the pre-existing mutant, hisG3096 (Hartman et al., 1971). This mutant was isolated from MNNG mutagenesis using methods identical to those for hisG1775. The mutant allele, hisG3096, was identified by direct PCR sequencing to carry the $asn_{169}$ (AAT) mutation which had replaced the wild type residue, $asp_{169}$ (GAT). Approximately 40 to 50 spontaneous and mutagen-induced revertants from tester strains made with hisG3096 were sequenced and all were found to be wild type. This site was changed by PCR mutagenesis to carry $gly_{169}$ (GGT) and subcloned into M13mp9::his1 (Artz et al., 1983). However, about 25% of the revertants from strains made with the $gly_{169}$ (GGT) mutant remained of mutant sequence (GGT not GAT). This indicated that about 25% of the reversion of this mutant was due to extragenic suppression of the $gly_{169}$ (GGT) mutation and the mutational events which led to the wild type phenotype were not directed at the $gly_{169}$ (GGT) codon.

The effect of changing the context of the target mutation on the incidence of missense suppression was investigated. The third base at the $asp_{169}$ codon, GAT, was not completely degenerate and a change to a G to maximize the precision of tRNA selection according to the wobbling rules based on the inherent degeneracy of the DNA code, changed the amino acid residue from $asp_{169}$ (GAT) to $glu_{169}$ (GAG). This conservative substitution was made using PCR mutagenesis methods which fixed the mutation into a DNA fragment that was subcloned into M13mp9::his1 (Artz et al., 1983) to determine the effect of $glu_{169}$ on the activity of ATP-phosphoribosyltransferase. A 21 bp DNA oligomer containing the context change was made as the anti-sense strand:
5'-GAC CAA CTC GCA GAT AGC GTC-3' (SEQ ID NO:11)

The oligomer, as the bottom, anti-sense strand, is shown with its reverse complement, the sense strand:

$asp_{169}$
5'-GAC GCT ATC TGC GAT TTG GTC-3' (wild type)
(SEQ ID NO: 12)

3'-CTG CGA TAG ACG CTC AAC CAG-5' (pseudo wild type)
(SEQ ID NO: 11)

The C in the bottom strand becomes a G in the top (i.e., sense strand) in the next round of replication and is fixed as GAG which translates to glutamate:

$glu_{169}$
5'-GAC GCT ATC TGC GAG TTG GTC-3' (pseudo wt)
(SEQ ID NO: 13)

3'-CTG CGA TAG ACG CTC AAC CAG-5'
(SEQ ID NO: 11)

The ATP-phosphoribosyltransferase remained active to give a His+ phenotype in complementation assays when glutamate was substituted for the wild type, aspartate residue in this position. This $glu_{169}$ (GAG) change was transferred to the chromosome (Blum et al., 1989). There was no detectable difference in the growth rate of cells carrying glutamate as compared to those carrying the wild type aspartate. Therefore, there was no selective advantage for the back-mutation of glutamate to aspartate. This context change in the glutamate mutant was phenotypically silent and therefore was designated as the psuedo wild type reference for Sets IV and V.

The base change for Set IV was engineered as $gly_{169}$ (GGG) based on $glu_{169}$ (GAG) as the wild type using methods similar to those used for constructing the GAG pseudo wild type. The mutation for hisG9133, fixed in a 23 bp DNA oligomer was synthesized in the anti-sense strand:
5'-GA GAC CAA CCC GCA GAT AGC GTC-3' (SEQ ID NO:14)

The mutant DNA oligomer is the bottom strand and is shown below with its reverse complement, the sense strand:

glu$_{169}$
5'-GAC GCT ATC TGC GAG TTG GTC TC-3' (pseudo wt)
(SEQ ID NO: 15)

3'-CTG CGA TAG ACG CCC AAC CAG AG-5' (mutant)
(SEQ ID NO: 14)

A G was inserted in the top sense strand opposite the C in the bottom strand in the next round of replication and was fixed as GGG which is translated as glycine:

gly$_{169}$
5'-GAC GCT ATC TGC GGG TTG GTC TC-3' (mutant)
(SEQ ID NO: 16)

3'-CTG CGA TAG ACG CCC AAC CAG AG-5'
(SEQ ID NO: 14)

The gly$_{169}$ mutant was designed to revert to the glu$_{169}$ pseudo wild type by a G:C to A:T transition.

The mutation carried in a PCR fragment was subcloned into M13mp9::his1 (Artz et al, 1983) and transferred to the chromosome by M13 transduction (Blum et al., 1989). P22int4HT was grown on the M13 transductant (hisG9133) and this phage was used to transfer this mutant allele, hisG9133, into tester strain backgrounds.

(b) Construction of TA7014, TA7024, TA7034, TA7044 and TA7004

TA7044 (hisG9133 Δara9 Δchl1004 (bio chlD uvrB chlA) galE503/pKM101) was made by P22 transduction using TA4490 as the recipient strain. The rfa derivative was isolated from C21 resistance and designated TA7004 (hisG9133 Δara9 Δchl1004 (bio chlD uvrB chlA) galE503 rfa1044/pKM101). The mutant allele, hisG9133, was transferred in a similar fashion to SB8052 and TA2864 to construct TA7014 (hisG9133 Δara9) and TA7034 (hisG9133 Δara9 Δchl1004 (bio chlD uvrB chlA) galE503), respectively. TA7014 was mated with TA4593 to make the R factor derivative, TA7024 (hisG9133 Δara9/pKM101).

(c) Mutagenicity Testing: Sensitivity of Reversion of Set IV

TA7044 (represented by the solid bars in FIG. 7) and TA7004 (represented by the hatched bars in FIG. 7) were tested extensively. This set was very responsive to MNNG which is known to induce primarily G:C to A:T transitions although it induces, to a lesser extent, all six possible base substitutions and other secondary mutations. MNNG induced 1800±170 revertants per plate which was over 100 times the spontaneous frequencies in TA7004. The reversion data for MNNG is shown in Table 2 but have been left out of FIG. 7 because the scale would obscure the mutagenic response from the other mutagens. Based on the high response of TA7004, MNNG was selected as the positive control for strains of Set IV.

The frequency of spontaneous revertants was decreased for GGG$_{gly}$ to approximately 50% of the rate for GGT mutant, probably due to the elimination of non-specific pathways of reversion as a result of the context change. In addition to its sensitivity to MNNG, TA7044 as represented by solid bars in FIG. 7 and TA7004 represented by hatched bars in FIG. 7 were found to detect a subset of mutagens such as ethyl methanesulfonate (EMS), 4-nitroquinoline-1-oxide (NQNO) and N4amC, approximately 20 to 50 times over spontaneous frequencies (See, FIG. 7). Both meG1 and formaldehyde (form) were preincubated for 20 min before plating.

(d) Verification of Mutagenic Specificity of Set IV

In spite of the different classes of mutagens that were readily detected by Set IV strains, sequence analyses of the revertants induced by these different classes were of the pseudo-wild type sequence (GAG) only. This confirmed that from over 100 spontaneous and induced revertants obtained from exposure to several different-acting mutagens, strains in Set IV carrying the mutant allele, hisG9133, reverted by expected G:C to A:T transitions only.

(e) Changing the Context of the Target Mutation to Eliminate Extragenic Pathways of Reversion for Set IV and Set V Although there exists a database on mutagenic agents and their mechanisms of action, (e.g., transitions, transversions, frameshifts, etc.), the properties governing the pathways of mutagenesis are not understood well enough to predict the behavior of mutagens in a physiological system. Nevertheless, because such a large proportion of mutations were reverting via extragenic pathways, strategies to restrict pathways of reversion to the target mutation were developed.

The revertants by definition are His+, and those that retain the mutant sequence must have a functional enzyme which has the appropriate amino acid residue at the target site even if the DNA codes for a mutant nonfunctional protein. It was speculated that the translational machinery was inserting the wild type amino acid; either by charging the tRNA complementing the mutant codon in the mRNA with the incorrect wild type amino acid, or the wild type amino acid is charged to its correct tRNA but the anticodon has been mutated to recognize the mutant mRNA. Since aminoacylation undergoes chemical proofreading by the synthetase, the amino acid is charged to its isoacceptor tRNA's with high accuracy. A mutation in the active site of the synthetase to accommodate very different amino acids such as val and glu seems unlikely. One possible explanation is that a single mutation in the anticodon of the tRNA correctly charged with the wild type amino acid allows recognition of mutant MRNA.

Since there was no practical way to eliminate tRNA genes as a target for mutagenic agents even though many tRNA genes have been mapped in E. coli K12 (Komine et al., 1990), strategies were devised to exclude the mutant charged tRNA's from the translational apparatus by reducing their efficiency during elongation of the polypeptides. It was thought that the MRNA could be changed to demand higher precision from cognate tRNA's, since the wobble position exists due to the inherent degeneracy of the genetic code. One way to decrease the wobble in the third position of the codon of mRNA or the first position of the anticodon of the incoming tRNA is to change the base which sometimes carries no unique information anyway. A single tRNA can recognize more than one codon. The base pairing between the first two codon positions follows the usual G:C and A:U pairing. The third base of the codon allows pairing between G and U as well as G and C which means that an A in the third position of the codon in the mRNA no longer carries unique information (because the U on the anticodon that reads it must also accommodate G). And C in the third position of the codon in the MRNA is no longer unique because the G on the anticodon that reads it must also read U. Therefore it is possible to recognize unique codons only when the third base of the codon in the mRNA is a G or U. U is never in the third position where it has to convey unique information which leaves G as the most precise base in the wobble position of the codon.

In addition, changes were made in the first position of the leu$_{170}$ (TTG) codon which is 3' of the target mutation, asp$_{169}$ (GAT) in hisG, since the detailed evidence at specified loci such as the lys and glu codons of trpA from *E. coli* (Murgola et al., 1984; Buckingham et al., 1990(b)) pointed to context effects for codons both 5' and 3' of the target mutation (3-1 doublet rule). Leu can be coded by CTG as well as the wild type TTG, but strains from this context change unexpectedly increased the frequency of suppression from about 35% to about 55% for the target mutation while the base that was changed to provide a different context remained the same.

5. Set V Strains: C:G→A:T Transversions (a) Target Mutation: hisG9130

The target mutation for Set V was made in parallel with Set IV. The derivatives of this set were based on ala$_{169}$ (GCG) substitution for the pseudo wild type, glu$_{169}$ (GAG) previously described in the construction of Set IV derivatives. The mutation for hisG9130 was carried in a 23 bp DNA oligomer which was synthesized in the anti-sense strand:

5'-GA GAC CAA CGC GCA GAT AGC GTC-3' (SEQ ID NO:17)

The DNA oligomer is shown as the bottom strand with its reverse complement the sense strand:

glu$_{169}$
5'-GAC GCT ATC TGC GAG TTG GTC TC-3' (pseudo wt)
(SEQ ID NO: 15)

3'-CTG CGA TAG ACG CGC AAC CAG AG-5' (mutant)
(SEQ ID NO: 17)

The G in the bottom strand directs a C to be inserted in the top sense strand in the next round of replication and is fixed as GCG which translates to alanine:

ala$_{169}$
5'-GAC GCT ATC TGC GCG TTG GTC TC-3' (mutant)
(SEQ ID NO: 18)

3'-CTG CGA TAG ACG CGC AAC CAG AG-5'
(SEQ ID NO: 17)

The ala$_{169}$ mutant reverts to the glu$_{169}$ pseudo-wild type by a C:T to A:T transversion.

The spontaneous frequency of reversion of the GCG$_{ala}$ mutant was reduced to about 70% of the GCT$_{ala}$ version. This reduction suggested that one or more pathways of reversion were made less prominent by the context change. The GCG$_{ala}$ mutation was transferred to the chromosome by M13 transduction as in Set IV and the resulting transductant was designated, hisG9130. P22int4HT was grown on hisG9130 and sterile phage lysate was used to transfer the mutation into tester strain backgrounds.

(b) Construction of TA7015, TA7025, TA7035, TA7045 and TA7005

The mutation, hisG9130, was transferred into TA4490 to make TA7045 (hisG9130 Δara9 Δchl1004 (bio chlD uvrB chlA) galE503/pKM101) by P22 transduction and TA7005 (hisG9133 Δara9 Δchl1004 (bio chlD uvrB chlA) galE503 rfa1045/pKM101) was isolated from resistance to C21 lysis. TA7015 (hisG9130 Δara9) and TA7035 (hisG9133 Δara9 Δchl1004 (bio chlD uvrB chlA) galE503) were made by P22 transduction into SB8052 and TA2864, respectively, while TA7025 (hisG9130 Δara9/pKM101) was made by conjugation with TA4593.

(c) Mutagenicity Testing: Reversion Sensitivity of Set V

All strains of Set V were very sensitive to 4-nitroquinoline-1-oxide (NQNO) mutagenesis. NQNO induced on average 4700±130 revertants per plate which was about 200 fold above the spontaneous frequency of reversion and thus was chosen as the positive control for this set of strains. The data for NQNO are shown in Table 2 but were not included in FIG. 8 because the scale would obscure the other mutagens in the subset that were detected to make C:G to A:T transversions. The subset of mutagens detected by Set V is shown in FIG. 8, where the solid bars represent reversion of TA7045 and the hatched bars represent reversion of TA7005. The mutagenic agents, meGl, form and CB1348, were preincubated for 20 min before plating.

(d) Verification of Mutagenic Specificity of Set V

Of all spontaneous and induced colonies of Set V derivatives obtained from reversion by NQNO that were sequenced, only the pseudo-wild type sequence, GAG, was observed. Similarly, the sequence of over 100 revertants induced by other mutagenic agents (FIG. 8) capable of inducing different changes, were found to be of only pseudo-wild type sequence for TA7045 and TA7005. Thus this set was specific for C:G to A:T transversions.

(e) Effect of Context change on Set V

Mutations were engineered for Sets II, IV, and V from a single degenerate mutant primer which incorporated the context change. To determine the effect of the context change for the target mutation in Set V (GCT and GCG), strains carrying just the mutation, TA4532 (GCT) and TA7015 (GCG) were tested with the SOS-independent mutagens, 25 μg 5-azacytidine (5azaC), 50 μg t-butylhydroperoxide (tBHP), 50 μg methyl glyoxal (meGl), 50 μg N4-hydroxycytidine (N4OHC) and 2 μg N-methyl-N'-nitro-N-nitrosoquanidine (MNNG) as shown in FIG. 9A and 9B.

The overall reduction in the number of revertants was approximately correlated with the exclusion of missense suppression pathways of mutagenesis as implied by the absence of mutant sequence in the revertants analyzed after the context change. This difference is illustrated by comparing the hatched bars (new GCG context) to the corresponding solid bars (original GCT wild type context) in FIG. 9A. The extent of suppression differed according to the mutagenic agent. The induced frequencies expressed as the ratio of spontaneous frequencies were increased for tBHP and MNNG; but remained the same for 5azaC and meGl; and were decreased for N4OHC (FIG. 9B). Therefore, in spite of the overall reduction in the numbers of revertants, the background levels were decreased by the context change to a larger extent than the induced frequencies.

The response induced by tBHP and MNNG, which were barely detectable in the higher background, rose clearly above background levels in the new context. In summary, the context change restricted the pathways of reversion to the target codon, ala$_{169}$ (GCG) in this example, and increased the signal to noise ratio for specific C:G to A:T transversions.

6. Set VI Strains: C:G→G:C Transversions (a) Target Mutation: hisC9070

The mutant, hisC9070 was obtained from 5-azacytidine mutagenesis and selected by two rounds of penicillin enrichment (Levin and Ames, 1986). The mutation was identified by PCR sequencing to be a G:C to C:G transversion in which the wild type $gly_{163}$ (GGA) was replaced by $arg_{163}$ (CGA).

$arg_{163}$
5'-AAT CCT ACC CGA CAA CTT ATC-3' (mutant)
(SEQ ID NO: 19)

5'-AAT CCT ACC GGA CAA CTT ATC-3' (wild type)
$gly_{163}$ (SEQ ID NO: 20)

The first G in the $gly_{163}$ codon was replaced with a C, so that the reversion of the arginine to the wild type glycine requires a C:G to G:C transversion.

$arg_{163}$
5'-AAT CCT ACC CGA CAA CTT ATC-3' (mutant)
(SEQ ID NO: 19)

5'-AAT CCT ACC CCA CAA CTT ATC-3' (pseudo-wild type)
$pro_{163}$ (SEQ ID NO: 21)

However the $arg_{163}$ mutant also reverts to proline, which results in an active histidinol-phosphate aminotransaminase. Therefore the $pro_{163}$ codon, CCA has been designated as a pseudo wild type sequence, and is obtained by a G:C to C:G transversion in the middle position of the $arg_{163}$ codon, CGA.

(b) Construction of TA7016, TA7026, TA7036, TA7046 and TA7006 hisC9070 was transduced into TA4490 to construct TA7046 (hisC9070 Δara9 Δchl1004 (bio chlD uvrB chlA) galE503/pKM101) and its rfa derivative was isolated from C21 lysis and designated, TA7006 (hisC9070 Δara9 Δchl1004 (bio chlD uvrB chlA) galE503 rfa1046/pKM101). TA7016 (hisC9070 Δara9) and TA7036 (hisC9070 Δara9 Δchl1004 (bio chlD uvrB chlA) galE503) were constructed by P22 transduction of hisC9070 to SB8052 and TA2864, respectively. TA7026 (hisC9070 Δara9/pKM101) was constructed by mating TA7016 with TA4593.

(c) Mutagenicity Testing: Sensitivity of Reversion of Set VI

Set VI shares NQNO with Sets IV and V as the positive control for mutagenicity testing, although the response to 5-azacytidine (5azaC) induction is unique to strains of Set VI. The reversion of TA7046 (represented by solid bars, left side) and TA7006 (represented by hatched bars, right side) induced by different compounds is shown in FIG. 10. It was interesting that ang/UVA gave a positive response by C:G to G:C transversions. Agents that are activated by UV irradiation generally prefer pyrimidines, and A is inserted in its place, not G. However, revertants of TA7006 induced by ang/UVA were sequenced and C:G to G:C transversions were confirmed. Both meGl and formaldehyde (form) were preincubated for 20 min before plating.

(d) Verification of Mutagenic Specificity of Set VI

Reversion of these strains resulted from changes in one of two possible pathways but not via missense suppression. However, both base changes found in the reversion events are within Set VI. The $arg_{163}$ (CGA) reverts via C:G to G:C to give the wildtype $gly_{163}$ (GGA) and reverts via G:C to C:G to give the pseudo-wild type, $pro_{163}$ (CCA). There was no measurable difference in the growth rate of cells carrying $gly_{163}$ or $pro_{163}$ in hisC. It is hypothesized that $gly_{163}$ functions as a hinge between two folding domains in this enzyme and that $pro_{163}$ approximates the same angle of folding between the two domains of the *Salmonella typhimurium* histidinol-phosphate aminotransminase, since no other amino acid substitutions were found in over 130 revertants sequenced. Thus the reversion of hisC9070 remained specifically within the base changes defined by Set VI, C:G to G:C transversions, albeit by two different pathways for the same set of base changes.

(e) Comparison of Set VI with TA4006 and TA4016

The mutant allele, hisC9070, was chosen because it was the basis of TA4006 (hisC9070 galE503 ΔuvrB bio chl1004 rfa1032/pKM101; Levin and Ames, 1986) and was proposed to have a specific reversion pathway. However, TA4006 was not reverted by 5azaC, (0 revertants), even though the TA4016 strain which carries just the mutation, hisC9070, (Table IV of Levin and Ames, 1986) was reported to give 265 revertants per plate with no spontaneous colonies. Since the mutation in hisC9070 was identified to be $arg_{163}$ (CGA) compared to the wild type, $gly_{163}$ (GGA), hisC9070 was reisolated by single colony purification. Even after reisolation, retesting hisC9070 with 5azaC did not induce more than 145±18 revertants per plate in over five independent experiments. This response was virtually identical to the 148±10 revertants per plate induced by 5azaC in TA7016 (hisC9070 Δara9). It was found that of the spontaneous and induced revertants of both hisC9070 strains sequenced, all were specifically of wild type, $gly_{163}$, GGA, or pseudo-wild type, $pro_{163}$, CCA.

Since TA4006 was not reverted by 5azaC, new strains were reconstructed using the herein described novel recipient and donor strains. It was found that 5azaC induced reversion of TA7046 at an average of 270±14 colonies per plate which was about twice as sensitive as our reisolated hisC9070. When TA7006, the comparable rfa derivative to TA4006, was tested with 5azaC, about 250±30 revertants were obtained. When ratios were calculated, TA7046 and TA7006 responded to 5azaC at 37 and 60 times above the spontaneous background frequencies, respectively. When the sensitivity of TA7006 was compared to the published sensitivity for TA4006 (Levin and Ames, 1986), TA7006 was about seven times more sensitive to reversion by ang/UVA than TA4006. Ang/UVA induced 11 revertants per plate in TA4006 which was about 1.5 fold over a spontaneous of 7 revertants in 8±4×10⁸ cells (Levin and Ames, 1986). By comparison, 76±3 revertants per plate were obtained in TA7006 which was about 19 fold over a spontaneous of 4 revertants per plate (in 8±4×10⁸ cells). Similarly, TA7006 was about 10 times more sensitive to induction by methyl glyoxal than was TA4006 when both were preincubated for 20 min.

The observation that TA7046 and TA7006 reverted by two different pathways, both of which indicated the same base change but on opposite strands, was surprising. It was found that $pro_{163}$ was able to substitute successfully for $gly_{163}$ in this site, because a substantial number of His+ revertants were CCA not GGA. Generally, glycine residues give maximal flexibility to the main polypeptide chain, while proline residues introduce very restrictive kinks in the main chain of a polypeptide. When the *S. typhimurium* wild type sequence was aligned with *E. coli* histidinol-phosphate aminotransferase, the corresponding $gly_{163}$ was 1 of 12 invariant residues found in the crystallized *E. coli* aspartate aminotransferase (Mehta et al., 1989). This residue in the aspartate aminotransferase is thought to act as a hinge between two folding domains that make up the active site. It would be interesting to see if pro in this site of the aspartate aminotransferase produces the same crystal structure as the wild type enzyme. If so, the main chain of the peptide held rigid by pro must be the precise angle that is allowed by the flexibility of gly in this position.

All of the testing performed with the six sets of strains of the invention followed the methods described in detail by Maron and Ames (1983) since these protocols have become the standard methods used by many laboratories throughout the world.

Detection and Characterization of Substitution Mutations

Standard methods were used for treatment of the six sets of strains with mutagenic agents as detailed by Maron and Ames, 1983, the content of which is herein incorporated by reference.

A. Selection of Tester Strains

It is preferred that the complete tester strains of the TA700X series, TA7001, TA7002, TA7003, TA7004, TA7005 and TA7006, be used for the initial testing of unknown agents in the absence of the S9 mixture. It is known that the minimum detection limit is an important parameter in determining the sensitivity of any detection system and that the greater the difference in magnitude of the actual test measurement from that limit, the more reliable the test measurement.

There is an upper limit for any detection system where measurements which exceeding this upper limit become unreliable. The upper limit of the Salmonella detection system is determined by the maximal number of distinguishable colonies that can physically grow on a standard agar plate (100×15 mm). However it is more preferable that this number does not exceed the linear response of mechanical colony counters or that which can be counted manually. It is most preferable that the dose of the mutagen be chosen such that the number of revertant colonies are minimally 5 fold over the spontaneous frequencies up to about 500 revertant colonies. This leaves sufficient area on the surface of the plate such that the background lawn can be checked for toxicity or other abnormalities (Maron and Ames, 1983). This is a major advantage of low spontaneous frequencies of the six sets of strains. The spontaneous frequencies of the current Ames tester strains are generally around 250±100 revertants per plate. In this case, induction of two times over background is already 500 colonies which is at the upper limit of what can be counted easily.

The sensitivity of any Salmonella tester strain is defined as the number of revertant colonies induced by a given mutagen as a ratio of the number of spontaneous revertants specific to that particular tester strain. A reproducible dose response curve with a sensitivity of 5 indicates a positive mutagenicity result in the Salmonella mutagenicity assay. Thus, an agent can be classified as a mutagen if the frequency of mutagen induced revertant colonies is 5 times greater than the spontaneous rate of reversion in the absence of the mutagen.

It should be noted that with some mutagens the response with TA704X series, TA7041, TA7042, TA7043, TA7044, TA7045 and TA7046, may be higher than with the TA700X series because these mutagens do not require rfa mutations to have maximal accessibility to DNA. For mutagenic agents like NQNO, the response from TA7045 was about 350±43 times above its spontaneous frequency, while the response from the complete tester strain was 210±30 times above its background rate of reversion (See, FIG. 11A).

If no positive response is observed with the test agent when using the TA700X series, some other derivative strains from the set may be more sensitive. For example, MNNG is most mutagenic in the Set IV representative strain, TA7014 (See, FIG. 11B), which has an intact DNA repair system and a complete outer membrane. The response to MNNG (4 $\mu$g/plate) for TA7014 was over 1800±160 times the background rate of reversion. The ratio in the complete tester strain, TA7004, was only 100±20, but was still respectable. For mutagens like MNNG, the TA701X series was preferable.

Strains other than the complete strain, TA700X, also provide more information as to the mutagenic mechanism of action. For example, mutagens like mitomycin C (MMC) induce the TA702X series at a higher level than the TA700X series (data not shown). Because agents like MMC are capable of interstrand crosslinking of DNA, exposure to MMC is lethal when the cell has been compromised for bulky excision repair. Thus strains like TA700X, TA704X and TA703X (Table 1) that carry the ΔuvrB mutation do not revert as well as TA702X. In addition to the aforementioned strains that revert by base substitution mutations, TA97a and TA98 may be used in conjunction to detect frameshift mutations.

B. Optimization of Concentration of Test Agent

In order to compare the response among the six sets of strains to determine the base substitutions that the test agent induces, a single concentration of the agent must be chosen to be tested with strains from each of the six sets. This concentration must be within the initial linear portion of the dose response curve for the most responsive strain and should result in a sensitivity of preferably about 5. Thus, a dose response curve must be determined for each test agent and should include a concentration that induces the number of revertants to increase at least about 5 fold above the number of spontaneous revertants for the strain used for testing.

If using an automated spiral plater (Spiral Systems Instruments, Bethesda, Md.) that dispenses both the fresh 12 h culture and a known concentration of the test agent or mixture of compounds in each spiral, the optimal dose for all strains can be approximated on six plates, a single plate for a representative strain from each of the six sets. If used in conjunction with a laser scanner (Spiral Systems Instruments, Bethesda, Md.) that counts the number of revertant colonies associated with each spiral, a dose response for each of the six representative strains can be determined directly.

If the test agent is diffusible in agar, it is preferable to use the spot test (Maron and Ames, 1983, p.197) to determine which of the six representative strains is most responsive to the test agent. The dose optimization should be done on the most responsive strain, and then the optimal dose can be used with each of the other five representative strains.

Arbitrary concentrations that span three logs of a test agent may be chosen for the initial testing. In most cases there are other mutagenic agents with similar chemical properties that have been tested and can give a first approximation of an appropriate range of concentrations. The Environmental Mutagen Information Center (EMIC: Maron and Ames, 1983) as well as reports in the literature for similar mutagenic agents are valuable resources. From the linear slope of the dose response curve a concentration can be chosen at about 80% to 90% of the dose that induces the maximal revertants, and that is about 5 times above the spontaneous frequency, to test the remaining five representative strains. The initial slope is correlated to the potency of the mutagen. For example, determination of the dose response for N4amC induction of TA7001 showed approximately 70 revertants per μg of mutagen from a linear regression analysis of the slope (y=132+71X R=0.991, See, FIG. 12). 10 μg of N4amC was chosen from a dose response curve to test other strains to determine which base changes were induced by N4amC. At this dose over 700 revertants from TA7001 were induced by N4amC. TA7004 was found to respond to this dose of N4amC at about 33 times above its spontaneous frequency. None of the four other strains, TA7002, TA7003, TA7005 and TA7006, responded to N4amC, therefore N4amC induced primarily A:T to G:C (Set I, TA7001) and G:C to A:T (Set IV, TA7004) transitions.

To determine the relative potency of mutagenicity of different mutagenic agents, a single Salmonella strain is used to obtain a dose response with each of the tested agents, and the results are expressed as revertants per pmole of mutagenic agent or equivalent thereof from the initial linear slope of the dose response curve.

C. Determination of Base Substitution

The sensitivity of each strain is calculated by dividing the number of revertants induced by treatment with a mutagenic agent by the number of spontaneous revertants for each strain. The sensitivities are then compared among strains to analyze which base substitutions were induced by the mutagenic agent and which were not detected by the set of strains used for testing.

A reference mutagen known to cause the specific base substitution for which a tester strain is diagnostic should be included as a positive control whenever a mutagenic agent is tested. Exemplary reference mutagens and their concentrations are listed in Table 2. Only streptonigrin and NQNO are necessary to test the mutability of all six strains, TA7001, TA7002, TA7003, TA7004, TA7005 and TA7006.

For example, the mutagenicity profile for 4-nitroquinoline-1-oxide (NQNO) illustrated that its interactions were primarily at C:G base pairs (See, FIG. 13A). The solid bars indicate the response from the TA704X strains which do not carry the rfa mutation while the hatched bars represent the response from the complete strains, TA700X. NQNO has been shown to activate the oncogene, Ki-ras and to produce skin tumors in mice. The quinoline ring of NQNO preferentially binds to guanine, giving two major DNA adducts, one in at the N2 position and the other at the C8 position. The relative proportions of these adducts and other products are dependent on the context in which the mutation is situated. NQNO induced the transversions: C:G to A:T (Set V) and C:G to G:C (Set VI) at frequencies of 295±8 and 206±9 times over the spontaneous rates of mutations, respectively. The transition, G:C to A:T (Set IV) was approximately 43±8 times over background rates, while the ratios of mutation frequencies were less than four at T:A base pairs represented by Sets I, II and III (FIG. 13A).

MNNG is known to induce a wide spectrum of mutations by forming adducts with both purines and pyrimidines. However, the predominant adduct, $O^6$-methylguanine mispairs with thymine instead of cytosine. In the next round of replication, thymine is correctly paired with adenine which replaces the original guanine. The resulting G:C to A:T transition as detected by Set IV was about 100±27 times above frequencies of background mutations (See, FIG. 13B).

Similarly, the thymine adduct, $O^4$-methylthymine causes misincorporation of guanine on the opposite strand of DNA, resulting in a A:T to G:C transition as detected by Set I. The response of Set I was about 11±2 times above rates of spontaneous mutations. Ratios for T:A to G:C transversions as detected by Set III was about the same as for Set I. Ratios

TABLE 2

| Set | Strain | Reference Mutagen | Concentration (μg/plate) | Spontaneous revertants 4 to 12 × 10⁸ cells/plate | Mutagen-Induced |
|---|---|---|---|---|---|
| I | TA7041 | N4-aminocytidine | 10 | 2.6 ± 1.6 | 2120 ± 35 |
| A:T→G:C | TA7001 | N4-aminocytidine | 10 | 2.5 ± 1.5 | 990 ± 55 |
| | TA7001 | streptonigrin | 0.1 | 2.5 ± 1.5 | 103 ± 19 |
| II | TA7042 | UVA/angelicin* | 0.1 | 6.8 ± 1.6 | 250 ± 15 |
| T:A→A:T | TA7002 | UVA/angelicin | 0.1 | 9.3 ± 3.0 | 400 ± 20 |
| | TA7002 | Streptonigrin | 0.1 | 9.3 ± 3.0 | 180 ± 7 |
| III | TA7043 | UVA/angelicin | 0.1 | 0.7 ± 0.3 | 153 ± 12 |
| T:A→G:C | TA7003 | UVA/angelicin | 0.1 | 0.1 ± 0.05 | 195 ± 2 |
| | TA7003 | Streptonigrin | 0.1 | 0.1 ± 0.05 | 63 ± 7 |
| IV | TA7044 | MNNG** | 4 | 20 ± 4 | 4900 ± 770 |
| G:C→A:T | TA7004 | MNNG | 4 | 18 ± 3.5 | 1770 ± 170 |
| | TA7044 | NQNO*** | 1 | 20 ± 4 | 870 ± 110 |
| | TA7004 | NQNO | 1 | 18 ± 3.5 | 620 ± 100 |
| V | TA7045 | NQNO | 1 | 20 ± 5 | 5900 ± 420 |
| C:G→A:T | TA7005 | NQNO | 1 | 23 ± 2.3 | 4700 ± 130 |
| | TA7005 | MMS**** | 650 | 23 ± 2.3 | 290 ± 30 |
| VI | TA7046 | NQNO | 1 | 7.4 ± 2.3 | 1150 ± 90 |
| C:G→G:C | TA7006 | NQNO | 1 | 4.0 ± 2.0 | 820 ± 35 |
| | TA7046 | 5-azacytidine | 25 | 7.4 ± 2.3 | 270 ± 14 |
| | TA7006 | 5-azacytidine | 25 | 4.0 ± 2.0 | 250 ± 30 |

*$UVA_{(320-400 \text{ nm})}$0.39 ± 0.01J
**N-methyl-N-nitro-$N^1$-nitrosoguanidine
***4-nitroquinoline-1-oxide
****methyl methanesulfonate Each base substitution is then interpreted as to what chemical adduct of the target base in the original mutant DNA might lead to the pre-mutagenic lesion that resulted in the observed base change.

for the transversions: T:A to A:T (Set II) and C:G to G:C (Set VI) were about 4. While the major type of point mutation is a G:C to A:T transition, the differences among the remaining sets were small.

Angelicin (ang) and other monofunctional psoralens have been the subject of extensive study because of their antiviral properties and their therapeutic potential in treating skin disorders like psoriasis. The major products of the photochemical reactions of ang and DNA are adducts linked by a cyclobutane ring to the 5–6 position of the pyrimidines. Their preference for thymine over cytosine is reflected by the response at T:A base pairs as compared to C:G base pairs (See, FIG. 13C). Furthermore, ang/UVA in the unique context of the mutation of Set III, induced the reversion of T:A to G:C at a frequency of approximately 195±14 times above the rates of spontaneous mutations. This can be compared to about 43±0.3 and 24±2 times for T:A to A:T transversions (Set II) and A:T to G:C transitions (Set I), respectively. Adducts formed at cytosines are much less efficient as reflected by the lower ratios of 19±1 for C:G to G:C (Set VI) and 5.3±0.7 for C:G to A:T (Set V) transversions. The G:C to A:T transition (Set IV) is detected at about 2±0.4 times the rates of spontaneous mutations and this low ratio is sometimes taken as a positive result in the original Salmonella mutagenicity assay. However, to determine whether angelicin/UVA results in G:C to A:T transitions, it should be demonstrated that induction is dose-dependent and that a dose can be found to give a ratio of 5. All Set IV revertants that were obtained from this single dose of angelicin/UVA were G:C to A:T transitions.

D. Modifications that Increase Mutagenicity

1. S9 Fraction

Mutagens that require activation by S9, the microsomal fraction of rat liver homogenate (Maron and Ames, 1983; p.188–190) can be tested by adding S9 to the liquid top agar together with the bacterial cells in the plate incorporation assay. S9 can also be incorporated along with a liquid preincubation period (Maron and Ames, 1983; p. 199) or can be distributed with the automated spiral plater (Spiral System Instruments). This microsomal fraction can be prepared according to Maron and Ames (supra., p.186) or purchased from several companies including Sitek Research Laboratories (Rockville, Md.) or Molecular Toxicology Inc. (Annapolis, Md.).

2. Preincubation Procedure

Tests of t-butyl hydroperoxide (tBHP) and cumene hydroperoxide (CHP) using the liquid preincubation procedure increased the response from a subset of strains, especially for TA7022. In FIG. 14, the solid and adjacent hatched bars represent induction by tBHP; and the open and stippled bars represent induction by CHP. The effect of a 20 min preincubation period before plate incorporation for tBHP can be illustrated by comparing the the hatched bars (20 min) to the solid bars where no liquid preincubation (0 min) was done. Similarly, the stippled bars represent 20 min as compared to the open bars where no liquid preincubation (0 min) was done for CHP. These results indicate that both tBHP and CHP induced primarily T:A to A:T transversion as indicated by the greatest response to TA7022 (FIG. 14). Also, both of these mutagenic agents prefer T:A base pairs as targets since higher levels of induction were obtained with TA7021, TA7022 and TA7023 than the remaining sets which have C:G base pairs at their target mutations.

E. Summary of Testing Strategy

It is recommended that a liquid preincubation period from 0 to 30 min be performed prior to plating as in the standard plate incorporation assay (Maron and Ames, 1983) in the initial screening of test agents to increase the probability of detection to a wide variety of mutagenic agents. This method is described as a separate procedure in Maron and Ames (1983) as a possible modification to the standard plate incorporation assay. In this method, it is recommended that an aliquot of the bacterial culture and the unknown test agent be mixed in a sterile tube and incubated at 37° C., gently shaking for 10 min before adding top agar. The top agar is then added and mixed briefly and plated quickly as in the standard plate incorporation assay. Once a response is detected by any of the strains, then it is most important to demonstrate that the induced response increases with the dose of the test agent. Furthermore, such a dose response relationship must be linear for several doses and the response for the optimal dose should be about 5, preferably at least 5 fold over the spontaneous reversion frequency of the strain used.

It is evident from the above results that the disclosed strains possess useful properties including easy handling of cells, low rates of spontaneous reversion mutation, sensitivity to mutagens and speed in obtaining definitive results. The strains also allow unambiguous characterization of each of the six possible base substitution mutations without the need for DNA sequencing, are sensitive to mutagens, and allow detection of the presence of mutagenic agents which are otherwise not detectable using the original Salmonella Ames strains.

Many advantages ensue from use of the disclosed strains. One can identify the presence of a potential mutagenic agent using strains from the six sets as well as determine the type and ratio of different DNA base substitutions induced by the agent. Furthermore, the relative potency of different mutagens in inducing specific substitution mutations may be determined. Further, where one is interested in ascertaining whether a mutagen induces a specific DNA base substitution mutation, for example because such a specific substitution mutation is implicated in development of specific tumors, derivative strains from the set which is specific for the mutation of interest may be used with advantage.

Further, many compounds in therapeutic use have genotoxic side effects. If those genotoxic attributes can be identified, then rational strategies can be chosen to redesign that part of the compound without destroying its therapeutic usefulness. The six sets of tester strains disclosed herein may be used to indicate which of the six possible base substitutions can be induced by a given compound and therefore, contribute to the understanding of the mechanism(s) of mutagenesis. If a compound cannot be altered to ameliorate its genotoxic properties, then an understanding of the mechanisms of mutagenesis may provide a rational basis for a compensating therapy or for changing the strategy used in its administration.

Furthermore, since an enormous and still growing database exists for mutagenicity as detected by the previous Salmonella tester strains, data obtained from these six sets of strains of the invention are immediately comparable. This provides not only a valuable perspective but an indisputable evaluation of the response of each strain. Users familiar with the available Salmonella strains will be able to use the disclosed TA7000 series of strains without investment of new equipment or supplies.

Furthermore, the low rates of spontaneous mutations of the strains account for the reliability and reproducibility of the data obtained using these strains. The rates of spontaneous mutations are less than 25 revertants per plate (Table 2) and vary as little as ±25% depending on the strain. By comparison, the currently available Salmonella strains TA97A, TA98, TA100, TA102 and TA104 have spontaneous rates of mutation as high as 350 revertants per plate and in some of the current Ames tester strains the spontaneous rates vary as much as ±100% (Agnese et al. 1984).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

BIBLIOGRAPHY

Agnese, G., D. Risso and S. De Flora. 1984. Statistical evaluation of inter- and intra-laboratory variations of the Ames test, as related to the genetic stability of Salmonella tester strains. *Mutat. Res.* 130, 27–44.

Artz, S., D. Holzschu, P. Blum and R. Shand. 1983. Use of M13mp phages to study gene regulation, structure and function: cloning and recombinational analysis of genes of the *Salmonella typhimurium* histidine operon. *Gene,* 26, 147–148.

Barnes, W. M. 1981. Cloning and restriction map of the first part of the histidine operon of *Salmonella typhimurium. J. Bacteriol.* 147, 124–134.

Bernstein, L., J. Kaldor, J. McCann and M. C. Pike. 1982. An empirical approach to the statistical analysis of mutagenesis data from the Salmonella test. *Mutat. Res.* 97, 267–281.

Bossi, L. and J. R. Roth. 1980. The influence of codon context on genetic code translation. *Nature,* 286, 123–127

Blum, P., D. Holzschu, H.-S. Kwan, D. Riggs and S. Artz. 1989. Gene replacement and retrieval with recombinant M13mp bacteriophages. *J. Bacteriol.,* 171, 538–546.

Buckingham, R. H. 1990. Codon Context. *Experientia,* 46, 1126–1133.

Buckingham, R. H., E. J. Murgola, P. Sorensen, F. T. Pagel, K. A. Hijazi, B. H. Mims, N. Figueroa, D. Brechemier-Baey and E. Coppin-Raynal. 1990(a). Effects of codon on the suppression of nonsense and missense mutations in the trpA gene of *Escherichia coli.* in: *The Ribosome: Structure, Function and Evolution,* pp. 541–545. Eds. W. E. Hill, A. Dahlberg, R. A. Garret, P. B. Moore, D. Schllessinger and J. R. Warner. American Society for Microbiology, Washington, D.C.

Buckingham, R. H., P. Sorenson, F. T. Pagel, K. A. Hijazi, B. H. Mims d. Brechemier-Baey, and E. J. Murgola. 1990(b). Third position base changes in codons 5' and 3' adjacent UGA codons affect UGA suppression in vivo. *Biochem. et Biophys. Acta,* 1050, 259–262.

Carlomagno, M. S., F. Blasi and C. B. Bruni. 1983. Gene organization in the distal part of the *Salmonella typhimurium* histidine operons and determination and sequence of the operon transcription terminator. *Mol. Gen. Genet.,* 191, 413–420.

Carlomagno, M. S., L. Chiariotti, P. Alifano, A. G. Nappo and C. B. Bruni. 1988. Structure and Function of the *Salmonella typhimurium* and *Escherichia coli* K-12 histidine operons. *J. Mol. Biol.,* 203, 585–606.

Claxon, L. D., V. S. Houk, L. G. Monteith, L. E. Myers and T. J. Hughes. 1991(a). Assessing the use of known mutagens to calibrate the *Salmonella typhimurium* mutagenicity assay: I. Without exogenous activation. *Mutat. Res.* 253, 137–147.

Claxon, L. D., V. S. Houk, J. R, Warner, L. E. Myers and T. J. Hughes. 1991(b). Assessing the use of known mutagens to calibrate the *Salmonella typhimurium* mutagenicity assay: II. With exogenous activation. *Mutat. Res.* 253, 149–159.

Cupples, C. G. and J. H. Miller. 1989. A set of lacZ mutations in *Escherichia coli* that allow rapid detection of each of the six base substitutions. *Proc. Natl. Acad. Sci. USA,* 86, 5345–5349.

Demerec, M., E. L. Lahr, E. Balbinder, T. Miyake, J. Ishidsu, K. Mizobuchi, and B. Mahler. 1960. Bacterial genetics. *Carnegie Inst. Wash. Yearbook.* 59, 426–441.

Downs D. M. and J. R. Roth. 1987. A novel P22 prophage in *Salmonella typhimurium.* Genetics 117, 367–380.

Elledge, S. L. and G. C. Walker. 1983. The muc genes of pKM101 are induced by DNA Damage. *J. Bacteriol.* 155, 1307–1315.

Fukasawa, T. and H. Nikaido. 1961. Galactase mutants of *Salmonella typhimurium.* Genetics 46, 1295–1303.

Grafe, A., I. E. Mattern and M. Green. 1981. A European collaborative study of the Ames assay. I. Results and general interpretation. *Mutat. Res.* 85, 391–410.

Hames, B. D. and S. J. Higgins, ed. 1987. Nucleic acid hybridisation a practical approach. IRL Press Ltd., Oxford, England.

Hampsey, M. 1991. A tester system for detecting each of the six base-pair substitutions in *Saccharomyces cerevisiae* by selecting for an essential cysteine in iso-1-cytochrome c. *Genetics,* 128, 59–67.

Haroun L. and B. N. Ames, *1977.* Mutagenicity of Selected Chemicals in the Salmonella/Microsome Mutagenicity Test. in: *Comparative Chemical Mutagenesis,* Chap. 4, pp.27–68. Eds. F. J. deSerres and M. D. Shelby, Plenum Press, New York.

Hartman, P. E., Z. Hartman, R. C. Stahl and B. N. Ames. 1971. classification and Mapping of Spontaneous and Induced Mutations in the Histidine Operon of Salmonella. *Adv. Genetics,* 16, 1–34.

Isono, K. and J. Yourno. 1974. Chemical carcinogens as frameshift mutagens: Salmonella DNA sequence sensitive to mutagenesis by polycyclic carcinogens. *Proc. Natl. Acad. Sci. USA* 71, 1612–1617.

Janion, C. 1978. The efficiency and extent of mutagenic activity of some new mutagens of base-analogue type. Mutat. Res. 56, 225–234.

Johnston, H. M. and John R. Roth. 1981. Genetic analysis of the histidine operon control region of *Salmonella typhimurium. J. Mol. Biol.,* 145, 713–734.

Kamitori, S., A. Okamoto, K. Hirotsu, T. Higuchi, S. Kuramitsu, H. Kagamiyama, Y. Matsuura and Y. Katsube. 1990. Three-dimensional structures of aspartate aminotransferase from *Escherichia coli* and its mutant enzyme at 2.5 A resolution. *J. Biochem.,* 108, 175–84.

Kier, L. E., D. J. Brusick, A. E. Auletta, E. S. Von Halle, M. M. Brown, V. F. Simmon, V. Dunkel, J. McCann, K. Mortelmans, M. Prival, T. K. Rao and V. Ray. 1986. The *Salmonella typhimurium*/mammalian microsomal assay report of the U.S. Environmental Protection Agency Gene-Tox Program. *Mutat. Res.* 168, 69–240.

Komine Y., T. Adachi, H. Inokuch and H. Ozeki. 1990. Genomic organization and physical mapping of transfer RNA genes in *Escherichia coli* K12. *J. Mol. Biol., 212, 579–598.*

Kunkel, T. A., J. D. Roberts and R. A. Zakour. 1987. Rapid and efficient site-specific mutagenesis without phenotypic selection. *Methods Enzymol.,* 154, 367–382.

Langer, P. J., W. G. Shanabruch, and G. C. Walker. 1981. Functional organization of plasmid pKM101. *J. Bacteriol.* 145, 1310–1316.

Levin, D. E. and B. N. Ames. 1986. Classifying mutagens as to their specificity in causing the six possible transitions and transversions: A simple analysis using the Salmonella mutagenicity assay. *Environ. Mutagenesis,* 8, 9–28.

Lim, V. I. and C. Venclovas. 1992. A model for interacting codon-anticodon duplexes located at the ribosomal A- and P-sites. *FEBS Let.,* 313, 133–137.

Lipman, D. J. and W. R. Pearson. (1985). Science 227, 1435–1442.

Maden, T. 1993. The translational apparatus, from Berlin. *Trends in Biochem. Sci.,* 18, 155–157.

Maldonado-Rodriguez, R., M. Espinosa-Lara and K. L. Beattie. 1991. Influence of neighboring base sequence on mutagenesis induced by in vitro misincorporation in the lacI gene of *Escherichia coli. Mut. Res.* 251, 217–226.

Maron, D. M. and B. N. Ames. 1983. Revised methods for the Salmonella mutagenicity test. *Mutat. Res.* 113, 173–215.

McCann, J., Spingarn, N. E., Kobori, J. and Ames, B. N. 1975. Detection of Carcinogens as Mutagens: Bacterial Tester Strains with R Factor Plasmids. *Proc. Natl. Acad. Sci. USA* 72, 979–983.

Mehta, P. K., T. I. Hale and P. Christen. 1989. Tyrosine aminotransferase, histidinol-phosphate aminotransferase, and aspartate aminotransferase are homologous proteins. *Eur. J. Biochem.,* 186, 249–253.

Mortelmans, K. 1975. Ph.D. Dissertation, Stanford University.

Murgola, E. J., F. T. Pagel and K. A. Hijazi. 1984. Codon context effects in missense suppression. *J. Mol. Biol.,* 175, 19–27.

Needleman, S. B. and C. D. Wunsch. (1970). J. Mol. Biol. 48, 443–453

Oeschger and Hartman, 1970. ICR-induced frameshift mutations in the histidine operon of Salmonella. *J. Bacteriol.* 101, 490–504.

Osawa, S., A. Muto, Y. Andachi, R. Tanaka and F. Yamao. 1990. Prokaryotic genetic code. *Experientia,* 46, 1097–1106.

Pages, D., K. Hijazi, E. J. Murgola, J. Finelli and R. H. Buckingham. 1991. Suppression of a double missense mutation by a mutant tRNA$^{phe}$ in *Escherichia coli. Nucleic Acids Res.,* 19, 867–869.

Perry, K. L. and G. C. Walker. 1982. Identification of plasmid (pKM101)-coded proteins involved in mutagenesis and UV resistance. *Nature* 300, 278–281.

Rick, P. D. 1987. Lipopolysaccharide biosynthesis in: *Escherichia coli* and *Salmonella typhimurium, Cellular and Molecular Biology,* pp. 648–662. Ed. in chief F. C. Neidhardt. American Society of Microbiology, Washington, D.C.

Saiki R. K., D. H. Gelfand, S. Stoffel, S. J. Scharf, R. Higuchi, G. T. Horn, K. B. Mullis and H. A. Erlich. 1988. Primer-directed enzymatic amplification of DNA with a thermostable DNA polymerase. *Science,* 239, 487–491.

Sanderson, K. E., J. Janzer and J. Head. 1981. Influence of lipopolysaccharide and protein in the cell envelope of recipient capacity in conjugation of *Salmonella typhimurium. J. Bacteriol.,* 148, 283–293.

Sanderson, K. E. and J. A. Hurley, 1990. Linkage map of *Salmonella typhimurium.* in: *Escherichia coli* and *Salmonella typhimurium,* cellular and molecular biology, pp. 877–918, Ed. in Chief, F. C. Neidhardt. American Society for Microbiology, Washington, D. C.

Sanderson, K. E., S. K. Kadam and P. R. MacLachlan. 1983. Derepression of F factor function in *Salmonella typhimurium. Can. J. Microbiol.* 29, 1205–1212.

Sanderson, K. E. and B. A. D. Stocker. 1987. *Salmonella typhimurium* strains used in genetic analysis. in: *Escherichia coli* and *Salmonella typhimurium,* cellular and molecular biology, pp. 1220–1224. Ed. in Chief. F. C. Neidhardt. American Society for Microbiolgy, Washington, D.C.

Schaff, D. A., R. A. Jarrett, S. R. Dlouhy, S. Ponniah, M. Stockelman, P. J. Stambrook and J. A. Tischfield. (1990). Mouse transgenes in human cells detect specific base substitutions. Proc. Natl. Acad. Sci. U.S.A. 87, 8675–8679.

Schmieger, H. 1972. Phage P22-Mutants with increased or decreased transduction abilities. *Molec. Gen. Genet.* 119, 75–82.

Shpaeer, E. G. 1986. Constraints on codon context in *Escherichia coli* genes; their possible role in modulating the efficiency of translation. *J. Mol. Biol.,* 188, 555–564.

Simarov, B. V., L. N. Mironova and S. G. Inge-Vechtomov. 1971. Nonsense-missense suppression in yeast. *Molec. Gen. Genetics,* 113, 302–307.

Sledziewska-Gojska, E., E. Grzesuik, A. Plachta and C. Janion. 1992. Mutagenesis of *Escherichia coli:* a method for determining mutagenic specificity by analysis of tRNA suppressors. *Mutagenesis,* 7, 41–46.

Smith, H. O. and M. Levine. 1967. A phage P22 gene controlling integration of prophage. *Virology* 31, 207–216.

Sorenson, M. A. and S. Pedersen. 1991. Absolute in vitro translation rates of individual codons in *Escherichia coli;* the two glutamic acid codons GAA and GAG are translated with a threefold difference in rate. *J. Mol. Biol.* 222, 265–280.

Stambrook P. J. and J. A. Tischfield. (1988). Methods and kits for identifying mutagenic agents and molecular mutations in DNA in mammalian cells. U.S. Pat. No. 4,792,520, issued Dec. 20, 1988.

Tucker, S. D., E. J. Murgola and F. T. Pagel. 1989. Missense and nonsense suppressors can correct frameshift mutations. *Biochimie,* 70, 729–739.

Turnbough, C. L. and B. R. Bochner. 1985. Toxicity of pyridine biosynthetic pathway intermediate carbanyl aspartate in *Salmonella typhimurium. J. Bacteriol.* 163, 500–505.

Wilkinson, R. G., P. Gemski, Jr. and B. A. D. Stocker. 1972. Non-smooth mutants of *Salmonella typhimurium:* differentiation by phage sensitivity and genetic mapping. *J. Gen. Microbiol.,* 70, 527–554.

Winston, F., D. Botstein and J. H. Miller. 1979. Characterization of amber and ochre suppressors in *Salmonella typhimurium. J. of Bacteriol.,* 137, 433–439.

Zinder, N. D. and J. Lederberg. 1952. Genetic exchange in Salmonella. J. Bacteriol. 64, 679–699.

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 900 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
ATG TTA GAC AAC ACC CGC TTA CGC ATA GCT ATT CAG AAA TCA GGC CGT      48
Met Leu Asp Asn Thr Arg Leu Arg Ile Ala Ile Gln Lys Ser Gly Arg
 1               5                  10                  15

TTA AGC GAT GAT TCA CGA GAA TTG CTG GCC CGC TGC GGC ATA AAA ATT      96
Leu Ser Asp Asp Ser Arg Glu Leu Leu Ala Arg Cys Gly Ile Lys Ile
             20                  25                  30

AAT TTA CAC ACT CAG CGC CTG ATT GCG ATG GCG GAA AAC ATG CCG ATT     144
Asn Leu His Thr Gln Arg Leu Ile Ala Met Ala Glu Asn Met Pro Ile
         35                  40                  45

GAT ATC CTG CGC GTG CGT GAT GAT GAC ATT CCG GGT CTG GTA ATG GAT     192
Asp Ile Leu Arg Val Arg Asp Asp Asp Ile Pro Gly Leu Val Met Asp
     50                  55                  60

GGC GTG GTC GAT CTC GGT ATT ATC GGC GAA AAC GTG CTG GAA GAA GAG     240
Gly Val Val Asp Leu Gly Ile Ile Gly Glu Asn Val Leu Glu Glu Glu
 65                  70                  75                  80

CTA CTC AAC CGC CGC GCA CAG GGC GAA GAT CCA CGC TAT TTA ACC CTG     288
Leu Leu Asn Arg Arg Ala Gln Gly Glu Asp Pro Arg Tyr Leu Thr Leu
                 85                  90                  95

CGC CGT CTT GAC TTC GGC GGC TGC CGT TTA TCG CTG GCA ACA CCG GTT     336
Arg Arg Leu Asp Phe Gly Gly Cys Arg Leu Ser Leu Ala Thr Pro Val
            100                 105                 110

GAC GAA GCC TGG GAC GGC CCG GCC GCG CTG GAC GGT AAA CGT ATC GCT     384
Asp Glu Ala Trp Asp Gly Pro Ala Ala Leu Asp Gly Lys Arg Ile Ala
        115                 120                 125

ACC TCA TAT CCG CAC CTC CTC AAA CGC TAC CTC GAC CAG AAA GGC GTC     432
Thr Ser Tyr Pro His Leu Leu Lys Arg Tyr Leu Asp Gln Lys Gly Val
    130                 135                 140

TCT TTT AAA TCG TGT CTG TTA AAT GGT TCT GTC GAA GTC GCG CCG CGC     480
Ser Phe Lys Ser Cys Leu Leu Asn Gly Ser Val Glu Val Ala Pro Arg
145                 150                 155                 160

GCG GGG CTG GCC GAC GCT ATC TGC GAT TTG GTC TCT ACC GGC GCG ACG     528
Ala Gly Leu Ala Asp Ala Ile Cys Asp Leu Val Ser Thr Gly Ala Thr
                165                 170                 175

CTT GAA GCT AAC GGC CTG CGT GAA GTC GAA GTT ATC TAC CGC TCT AAA     576
Leu Glu Ala Asn Gly Leu Arg Glu Val Glu Val Ile Tyr Arg Ser Lys
            180                 185                 190

GCC TGT CTG ATT CAG CGC GAC GGT GAG ATG GCA CAG AGC AAG CAA GAG     624
Ala Cys Leu Ile Gln Arg Asp Gly Glu Met Ala Gln Ser Lys Gln Glu
        195                 200                 205

CTG ATC GAT AAA TTG CTG ACC CGT ATT CAG GGC GTG ATT CAG GCG CGC     672
Leu Ile Asp Lys Leu Leu Thr Arg Ile Gln Gly Val Ile Gln Ala Arg
    210                 215                 220

GAA TCG AAA TAC ATC ATG ATG CAC GCG CCA AGT GAA CGC TGG GAA GAG     720
Glu Ser Lys Tyr Ile Met Met His Ala Pro Ser Glu Arg Leu Glu Glu
225                 230                 235                 240

GTT ATC GCC CTG CTG CCA GGC GCC GAA AGG CCG ACA ATT CTG CCG CTG     768
Val Ile Ala Leu Leu Pro Gly Ala Glu Arg Pro Thr Ile Leu Pro Leu
```

|     |     |     |     |     |     |     |     | 245 |     |     |     |     | 250 |     |     |     |     | 255 |     |     |
|-----|-----|-----|-----|-----|-----|-----|-----|-----|-----|-----|-----|-----|-----|-----|-----|-----|-----|-----|-----|-----|

```
GCA  GGC  GAG  CAA  CAG  CGC  GTG  GCG  ATG  CAC  ATG  GTC  AGC  AGC  GAA  ACG         816
Ala  Gly  Glu  Gln  Gln  Arg  Val  Ala  Met  His  Met  Val  Ser  Ser  Glu  Thr
               260                          265                 270

TTG  TTC  TGG  GAA  ACC  ATG  GAG  AAA  CTG  AAA  GCG  CTT  GGC  GCC  AGC  TCG         864
Leu  Phe  Trp  Glu  Thr  Met  Glu  Lys  Leu  Lys  Ala  Leu  Gly  Ala  Ser  Ser
          275                          280                 285

ATT  CTG  GTA  CTG  CCG  ATC  GAG  AAG  ATG  ATG  GAG  TGA                             900
Ile  Leu  Val  Leu  Pro  Ile  Glu  Lys  Met  Met  Glu   *
          290                     295
```

( 2 ) INFORMATION FOR SEQ ID NO:2:

( i ) SEQUENCE CHARACTERISTICS:
        ( A ) LENGTH: 299 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Leu  Asp  Asn  Thr  Arg  Leu  Arg  Ile  Ala  Ile  Gln  Lys  Ser  Gly  Arg
 1                   5                        10                      15

Leu  Ser  Asp  Asp  Ser  Arg  Glu  Leu  Leu  Ala  Arg  Cys  Gly  Ile  Lys  Ile
                20                        25                      30

Asn  Leu  His  Thr  Gln  Arg  Leu  Ile  Ala  Met  Ala  Glu  Asn  Met  Pro  Ile
                35                        40                      45

Asp  Ile  Leu  Arg  Val  Arg  Asp  Asp  Ile  Pro  Gly  Leu  Val  Met  Asp
           50                        55                      60

Gly  Val  Val  Asp  Leu  Gly  Ile  Ile  Gly  Glu  Asn  Val  Leu  Glu  Glu
 65                       70                        75                      80

Leu  Leu  Asn  Arg  Arg  Ala  Gln  Gly  Glu  Asp  Pro  Arg  Tyr  Leu  Thr  Leu
                85                        90                      95

Arg  Arg  Leu  Asp  Phe  Gly  Gly  Cys  Arg  Leu  Ser  Leu  Ala  Thr  Pro  Val
               100                       105                     110

Asp  Glu  Ala  Trp  Asp  Gly  Pro  Ala  Ala  Leu  Asp  Gly  Lys  Arg  Ile  Ala
               115                       120                     125

Thr  Ser  Tyr  Pro  His  Leu  Leu  Lys  Arg  Tyr  Leu  Asp  Gln  Lys  Gly  Val
     130                       135                       140

Ser  Phe  Lys  Ser  Cys  Leu  Leu  Asn  Gly  Ser  Val  Glu  Val  Ala  Pro  Arg
145                       150                       155                     160

Ala  Gly  Leu  Ala  Asp  Ala  Ile  Cys  Asp  Leu  Val  Ser  Thr  Gly  Ala  Thr
                    165                       170                     175

Leu  Glu  Ala  Asn  Gly  Leu  Arg  Glu  Val  Glu  Val  Ile  Tyr  Arg  Ser  Lys
                180                       185                     190

Ala  Cys  Leu  Ile  Gln  Arg  Asp  Gly  Glu  Met  Ala  Gln  Ser  Lys  Gln  Glu
          195                       200                     205

Leu  Ile  Asp  Lys  Leu  Leu  Thr  Arg  Ile  Gln  Gly  Val  Ile  Gln  Ala  Arg
     210                       215                       220

Glu  Ser  Lys  Tyr  Ile  Met  Met  His  Ala  Pro  Ser  Glu  Arg  Leu  Glu  Glu
225                       230                       235                     240

Val  Ile  Ala  Leu  Leu  Pro  Gly  Ala  Glu  Arg  Pro  Thr  Ile  Leu  Pro  Leu
                    245                       250                     255

Ala  Gly  Glu  Gln  Gln  Arg  Val  Ala  Met  His  Met  Val  Ser  Ser  Glu  Thr
               260                       265                     270

Leu  Phe  Trp  Glu  Thr  Met  Glu  Lys  Leu  Lys  Ala  Leu  Gly  Ala  Ser  Ser
          275                       280                     285
```

```
Ile  Leu  Val  Leu  Pro  Ile  Glu  Lys  Met  Met  Glu
     290                 295
```

( 2 ) INFORMATION FOR SEQ ID NO:3:

( i ) SEQUENCE CHARACTERISTICS:
        ( A ) LENGTH: 1080 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
ATG  AGC  ACT  GAA  AAC  ACT  CTC  AGC  GTC  GCT  GAC  TTA  GCC  CGT  GAA  AAT       48
Met  Ser  Thr  Glu  Asn  Thr  Leu  Ser  Val  Ala  Asp  Leu  Ala  Arg  Glu  Asn
 1                   5                        10                       15

GTC  CGC  AAC  CTG  GTA  CCG  TAT  CAG  TCT  GCC  CGC  CGT  CTG  GGC  GGT  AAC       96
Val  Arg  Asn  Leu  Val  Pro  Tyr  Gln  Ser  Ala  Arg  Arg  Leu  Gly  Gly  Asn
                     20                       25                      30

GGC  GAT  GTC  TGG  CTG  AAC  GCG  AAT  GAA  TTC  CCG  ACA  GCG  GTG  GAG  TTT      144
Gly  Asp  Val  Trp  Leu  Asn  Ala  Asn  Glu  Phe  Pro  Thr  Ala  Val  Glu  Phe
                35                        40                       45

CAG  CTC  ACC  CAA  CAA  ACG  CTT  AAC  CGC  TAC  CCG  GAA  TGC  CAG  CCA  AAG      192
Gln  Leu  Thr  Gln  Gln  Thr  Leu  Asn  Arg  Tyr  Pro  Glu  Cys  Gln  Pro  Lys
     50                       55                        60

GCC  GTG  ATT  GAA  AAC  TAC  GCG  CAA  TAT  GCT  GGC  GTA  AAG  CCG  GAG  CAG      240
Ala  Val  Ile  Glu  Asn  Tyr  Ala  Gln  Tyr  Ala  Gly  Val  Lys  Pro  Glu  Gln
 65                       70                       75                        80

GTG  CTG  GTC  AGC  CGC  GGC  GCG  GAT  GAA  GGG  ATC  GAG  CTG  GTG  ATC  CGC      288
Val  Leu  Val  Ser  Arg  Gly  Ala  Asp  Glu  Gly  Ile  Glu  Leu  Val  Ile  Arg
                     85                       90                       95

GCC  TTC  TGT  GAA  CCG  GGG  AAA  GAC  GCC  ATT  CTC  TAC  TGT  CCG  CCC  ACT      336
Ala  Phe  Cys  Glu  Pro  Gly  Lys  Asp  Ala  Ile  Leu  Tyr  Cys  Pro  Pro  Thr
                    100                      105                     110

TAC  GGT  ATG  TAC  AGC  GTC  AGC  GCC  GAA  ACC  ATT  GGC  GTA  GAG  CGC  CGG      384
Tyr  Gly  Met  Tyr  Ser  Val  Ser  Ala  Glu  Thr  Ile  Gly  Val  Glu  Arg  Arg
          115                      120                      125

ACG  GTT  CCC  GCG  CTT  GAA  AAC  TGG  CAG  CTG  GAT  CTA  CAG  GGG  ATT  TCC      432
Thr  Val  Pro  Ala  Leu  Glu  Asn  Trp  Gln  Leu  Asp  Leu  Gln  Gly  Ile  Ser
     130                      135                      140

GAC  AAC  CTT  GAC  GGC  ACA  AAA  GTG  GTG  TTC  GTT  TGT  AGC  CCC  AAT  AAT      480
Asp  Asn  Leu  Asp  Gly  Thr  Lys  Val  Val  Phe  Val  Cys  Ser  Pro  Asn  Asn
145                      150                      155                     160

CCT  ACC  GGA  CAA  CTT  ATC  AAC  CCG  CAG  GAT  CTG  CGC  ACG  CTG  CTG  GAG      528
Pro  Thr  Gly  Gln  Leu  Ile  Asn  Pro  Gln  Asp  Leu  Arg  Thr  Leu  Leu  Glu
                          165                      170                     175

TTG  ACA  CGC  GGT  AAA  GCG  ATA  GTC  GTC  GCC  GAC  GAA  GCT  TAT  ATT  GAG      576
Leu  Thr  Arg  Gly  Lys  Ala  Ile  Val  Val  Ala  Asp  Glu  Ala  Tyr  Ile  Glu
                    180                      185                     190

TTT  TGC  CCG  CAG  GCC  ACG  CTG  ACA  GGC  TGG  CTG  GTT  GAA  TAT  CCT  CAT      624
Phe  Cys  Pro  Gln  Ala  Thr  Leu  Thr  Gly  Trp  Leu  Val  Glu  Tyr  Pro  His
          195                      200                      205

CTG  GTT  ATC  CTG  CGC  ACA  TTG  TCG  AAA  GCT  TTT  GCG  CTG  GCG  GGT  CTG      672
Leu  Val  Ile  Leu  Arg  Thr  Leu  Ser  Lys  Ala  Phe  Ala  Leu  Ala  Gly  Leu
     210                      215                      220

CGC  TGC  GGC  TTT  ACA  CTG  GCT  AAT  GAA  GAG  GTG  ATC  AAC  CTG  CTG  TTA      720
Arg  Cys  Gly  Phe  Thr  Leu  Ala  Asn  Glu  Glu  Val  Ile  Asn  Leu  Leu  Leu
225                      230                      235                     240

AAA  GTG  ATC  GCC  CCT  TAT  CCG  CTT  TCT  ACG  CCA  GTG  GCG  GAT  ATC  GCC      768
Lys  Val  Ile  Ala  Pro  Tyr  Pro  Leu  Ser  Thr  Pro  Val  Ala  Asp  Ile  Ala
                          245                      250                     255

GCC  CAG  GCG  CTG  TGC  CCG  CAG  GGA  ATA  AAC  GCA  ATG  CGC  GAT  CGC  GTG      816
Ala  Gln  Ala  Leu  Cys  Pro  Gln  Gly  Ile  Asn  Ala  Met  Arg  Asp  Arg  Val
```

|                          |                          |                          |      |
|--------------------------|--------------------------|--------------------------|------|
| 260                      | 265                      | 270                      |      |
| GCG CAG ACA GTG CAG GAA CGT CAG TAT CTG GTG AAT GCC CTG CAA CAG | | | 864 |
| Ala Gln Thr Val Gln Glu Arg Gln Tyr Leu Val Asn Ala Leu Gln Gln | | | |
| 275                      | 280                      | 285                      |      |
| ACC GCC TGC GTA GAA CAC GTC TTT GAC TCT GAA ACC AAC TAT ATT CTG | | | 912 |
| Thr Ala Cys Val Glu His Val Phe Asp Ser Glu Thr Asn Tyr Ile Leu | | | |
| 290                      | 295                      | 300                      |      |
| GCG CGG TTT ACC GCC TCC AGC AGC GTG TTT AAA TCC TTA TGG GAT CAG | | | 960 |
| Ala Arg Phe Thr Ala Ser Ser Ser Val Phe Lys Ser Leu Trp Asp Gln | | | |
| 305                      | 310                      | 315                      | 320  |
| GGC ATT ATC TTA CGC GAT CAG AAT AAA CAA CCT TCT TTA AGC GGC TGC | | | 1008 |
| Gly Ile Ile Leu Arg Asp Gln Asn Lys Gln Pro Ser Leu Ser Gly Cys | | | |
|                          | 325                      | 330                      | 335  |
| CTG CGG ATT ACG GTC GGC ACC CGC CAG GAA AAC CAG CGC GTC ATT GAC | | | 1056 |
| Leu Arg Ile Thr Val Gly Thr Arg Gln Glu Asn Gln Arg Val Ile Asp | | | |
|                          | 340                      | 345                      | 350  |
| GCC TTA CGT GCG GAG CCA GTA TGA | | | 1080 |
| Ala Leu Arg Ala Glu Pro Val   *  | | | |
| 355 | | | |

( 2 ) INFORMATION FOR SEQ ID NO:4:

( i ) SEQUENCE CHARACTERISTICS:
        ( A ) LENGTH: 359 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ser | Thr | Glu | Asn | Thr | Leu | Ser | Val | Ala | Asp | Leu | Ala | Arg | Glu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Arg | Asn | Leu | Val | Pro | Tyr | Gln | Ser | Ala | Arg | Arg | Leu | Gly | Gly | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Asp | Val | Trp | Leu | Asn | Ala | Asn | Glu | Phe | Pro | Thr | Ala | Val | Glu | Phe |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Gln | Leu | Thr | Gln | Gln | Thr | Leu | Asn | Arg | Tyr | Pro | Glu | Cys | Gln | Pro | Lys |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Ala | Val | Ile | Glu | Asn | Tyr | Ala | Gln | Tyr | Ala | Gly | Val | Lys | Pro | Glu | Gln |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Val | Leu | Val | Ser | Arg | Gly | Ala | Asp | Glu | Gly | Ile | Glu | Leu | Val | Ile | Arg |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Phe | Cys | Glu | Pro | Gly | Lys | Asp | Ala | Ile | Leu | Tyr | Cys | Pro | Pro | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Tyr | Gly | Met | Tyr | Ser | Val | Ser | Ala | Glu | Thr | Ile | Gly | Val | Glu | Arg | Arg |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Thr | Val | Pro | Ala | Leu | Glu | Asn | Trp | Gln | Leu | Asp | Leu | Gln | Gly | Ile | Ser |
|-----|-----|-----|-----|-----|-----|-----|-----|-----|-----|-----|-----|-----|-----|-----|-----|
|     |     | 130 |     |     |     |     | 135 |     |     |     |     | 140 |     |     |     |

| Asp | Asn | Leu | Asp | Gly | Thr | Lys | Val | Val | Phe | Val | Cys | Ser | Pro | Asn | Asn |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Pro | Thr | Gly | Gln | Leu | Ile | Asn | Pro | Gln | Asp | Leu | Arg | Thr | Leu | Leu | Glu |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Leu | Thr | Arg | Gly | Lys | Ala | Ile | Val | Val | Ala | Asp | Glu | Ala | Tyr | Ile | Glu |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Phe | Cys | Pro | Gln | Ala | Thr | Leu | Thr | Gly | Trp | Leu | Val | Glu | Tyr | Pro | His |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Leu | Val | Ile | Leu | Arg | Thr | Leu | Ser | Lys | Ala | Phe | Ala | Leu | Ala | Gly | Leu |
|-----|-----|-----|-----|-----|-----|-----|-----|-----|-----|-----|-----|-----|-----|-----|-----|
|     |     | 210 |     |     |     |     | 215 |     |     |     |     | 220 |     |     |     |

| | | | | | | | | | | | | | |
|---|---|---|---|---|---|---|---|---|---|---|---|---|---|
| Arg 225 | Cys | Gly | Phe | Thr 230 | Leu | Ala | Asn | Glu | Val 235 | Ile | Asn | Leu | Leu 240 |
| Lys | Val | Ile | Ala | Pro 245 | Tyr | Pro | Leu | Ser | Thr 250 | Pro | Val | Ala | Asp | Ile 255 | Ala |
| Ala | Gln | Ala | Leu 260 | Cys | Pro | Gln | Gly | Ile 265 | Asn | Ala | Met | Arg | Asp 270 | Arg | Val |
| Ala | Gln | Thr 275 | Val | Gln | Glu | Arg | Gln 280 | Tyr | Leu | Val | Asn | Ala 285 | Leu | Gln | Gln |
| Thr | Ala 290 | Cys | Val | Glu | His | Val 295 | Phe | Asp | Ser | Glu | Thr 300 | Asn | Tyr | Ile | Leu |
| Ala 305 | Arg | Phe | Thr | Ala | Ser 310 | Ser | Ser | Val | Phe | Lys 315 | Ser | Leu | Trp | Asp | Gln 320 |
| Gly | Ile | Ile | Leu | Arg 325 | Asp | Gln | Asn | Lys | Gln 330 | Pro | Ser | Leu | Ser | Gly 335 | Cys |
| Leu | Arg | Ile | Thr 340 | Val | Gly | Thr | Arg | Gln 345 | Glu | Asn | Gln | Arg | Val 350 | Ile | Asp |
| Ala | Leu | Arg 355 | Ala | Glu | Pro | Val | | | | | | | | | |

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:5:

```
GTC TGT TAA ATG ATT CTG TC                                        20
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:6:

```
GTC TGT TAA ATG GTT CTG TC                                        20
```

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:7:

```
CGC ACA TTG TCG ATA GCT TTT G                                     22
```

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:8:

```
CGC ACA TTG TCG AAA GCT TTT G                                     22
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GAC AGA AAC ATT TAA CAG AC    20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:10:

GTC TGT TAA ATG TTT CTG TC    20

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:11:

GAC CAA CTC GCA GAT AGC GTC    21

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:12:

GAC GCT ATC TGC GAT TTG GTC    21

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GAC GCT ATC TGC GAG TTG GTC    21

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GAG ACC AAC CCG CAG ATA GCG TC    23

( 2 ) INFORMATION FOR SEQ ID NO:15:

(i) SEQUENCE CHARACTERISTICS:
    (A) LENGTH: 23 base pairs
    (B) TYPE: nucleic acid
    (C) STRANDEDNESS: double
    (D) TOPOLOGY: linear (xi) SEQUENCE DESCRIPTION: SEQ ID NO:15:

GAC GCT ATC TGC GAG TTG GTC TC                    23

(2) INFORMATION FOR SEQ ID NO:16:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (xi) SEQUENCE DESCRIPTION: SEQ ID NO:16:

GAC GCT ATC TGC GGG TTG GTC TC                    23

(2) INFORMATION FOR SEQ ID NO:17:

(i) SEQUENCE CHARACTERISTICS:
    (A) LENGTH: 23 base pairs
    (B) TYPE: nucleic acid
    (C) STRANDEDNESS: double
    (D) TOPOLOGY: linear (xi) SEQUENCE DESCRIPTION: SEQ ID NO:17:

GAG ACC AAC GCG CAG ATA GCG TC                    23

(2) INFORMATION FOR SEQ ID NO:18:

(i) SEQUENCE CHARACTERISTICS:
    (A) LENGTH: 23 base pairs
    (B) TYPE: nucleic acid
    (C) STRANDEDNESS: double
    (D) TOPOLOGY: linear (xi) SEQUENCE DESCRIPTION: SEQ ID NO:18:

GAC GCT ATC TGC GCG TTG GTC TC                    23

(2) INFORMATION FOR SEQ ID NO:19:

(i) SEQUENCE CHARACTERISTICS:
    (A) LENGTH: 21 base pairs
    (B) TYPE: nucleic acid
    (C) STRANDEDNESS: double
    (D) TOPOLOGY: linear (xi) SEQUENCE DESCRIPTION: SEQ ID NO:19:

AAT CCT ACC CGA CAA CTT ATC                       21

(2) INFORMATION FOR SEQ ID NO:20:

(i) SEQUENCE CHARACTERISTICS:
    (A) LENGTH: 21 base pairs
    (B) TYPE: nucleic acid
    (C) STRANDEDNESS: double
    (D) TOPOLOGY: linear (xi) SEQUENCE DESCRIPTION: SEQ ID NO:20:

AAT CCT ACC GGA CAA CTT ATC                       21

(2) INFORMATION FOR SEQ ID NO:21:

(i) SEQUENCE CHARACTERISTICS:
    (A) LENGTH: 21 base pairs

-continued ( B ) TYPE: nucleic acid
( C ) STRANDEDNESS: double
( D ) TOPOLOGY: linear ( x i ) SEQUENCE DESCRIPTION: SEQ ID NO:21:

ATT CCT ACC CCA CAA CTT ATC                                            2 1

What is claimed is:

1. A Salmonella bacterium comprising a DNA sequence having a substitution of thymine for adenine at a specific nucleotide, said substitution rendering said bacterium non-selectable for a known Salmonella characteristic, said bacterium reverting to a cell selectable for said characteristic only from a substitution of adenine for thymine at said specific nucleotide and wherein a culture of said bacterium has an average reversion rate to cells selectable for said characteristic of at least about 10 times greater than spontaneous frequency when 8 plus or minus $4 \times 10^8$ of said cells of the culture are treated with 0.1 µg angelicin activated by UVA irradiation.

2. A method for identifying a mutagen that induces thymine to adenine transversion mutations, said method comprising:
   (a) exposing a Salmonella bacterium according to claim 1 to said mutagen for a time sufficient to allow DNA mutations to occur, wherein said Salmonella bacterium according to claim 1 is non-selectable for a known Salmonella characteristic;
   (b) culturing said bacterium in a cell culture medium which is selective for the growth of cells having said known Salmonella characteristic; and
   (c) identifying the number of said bacterium that grow in the cell culture medium of (b), wherein the number of bacterium that grow in the cell culture medium of (b) is directly proportional to the ability of said mutagen to induce thymine to adenine transversion mutations.

3. A Salmonella bacterium comprising a DNA sequence having a substitution of thymine for guanine at a specific nucleotide, said substitution rendering said bacterium non-selectable for a known Salmonella characteristic, said bacterium reverting to a cell selectable for said characteristic only from a substitution of guanine for thymine at said specific nucleotide and wherein a culture of said bacterium has an average reversion rate to cells selectable for said characteristic of at least about 10 times greater than spontaneous frequency when 8 plus or minus $4 \times 10^8$ of said cells of the culture are treated with 0.1 µg angelicin activated by UVA irradiation.

4. A method for identifying a mutagen that induces thymine to guanine transition mutations, said method comprising:
   (a) exposing a Salmonella bacterium according to claim 3 to said mutagen for a time sufficient to allow DNA mutations to occur, wherein said Salmonella bacterium according to claim 3 is non-selectable for a known Salmonella characteristic;
   (b) culturing said bacterium in a cell culture medium which is selective for the growth of cells having said known Salmonella characteristic; and
   (c) identifying the number of said bacterium that grow in the cell culture medium of (b), wherein the number of bacterium that grow in the cell culture medium of (b) is directly proportional to the ability of said mutagen to induce thymine to guanine transition mutations.

5. A Salmonella bacterium comprising a DNA sequence having a substitution of guanine for adenine at a specific nucleotide, said substitution rendering said bacterium non-selectable for a known Salmonella characteristic, said bacterium reverting to a cell selectable for said characteristic only from a substitution of adenine for guanine at said specific nucleotide and wherein a culture of said bacterium has an average reversion rate to cells selectable for said characteristic of at least about 10 times greater than spontaneous frequency when 8 plus or minus $4 \times 10^8$ of said cells of the culture are treated with 4 µg of N-methyl-N'-nitro-N-nitrosoguanidine.

6. A method for identifying a mutagen that induces guanine to adenine transition mutations, said method comprising:
   (a) exposing a Salmonella bacterium according to claim 5 to said mutagen for a time sufficient to allow DNA mutations to occur, wherein said Salmonella bacterium according to claim 5 is non-selectable for a known Salmonella characteristic;
   (b) culturing said bacterium in a cell culture medium which is selective for the growth of cells having said known Salmonella characteristic; and
   (c) identifying the number of said bacterium that grow in the cell culture medium of (b), wherein the number of bacterium that grow in the cell culture medium of (b) is directly proportional to the ability of said mutagen to induce guanine to adenine transition mutations.

7. A Salmonella bacterium comprising a DNA sequence having a substitution of cytosine for adenine at a specific nucleotide, said substitution rendering said bacterium non-selectable for a known Salmonella characteristic, said bacterium reverting to a cell selectable for said characteristic only from a substitution of adenine for cytosine at said specific nucleotide and wherein a culture of said bacterium has an average reversion rate to cells selectable for said characteristic of at least about 10 times greater than spontaneous frequency when 8 plus or minus $4 \times 10^8$ of said cells of the culture are treated with 30 µg of methyl glyoxal.

8. A method for identifying a mutagen that induces cytosine to adenine transition mutations, said method comprising:
   (a) exposing a Salmonella bacterium according to claim 7 to said mutagen for a time sufficient to allow DNA mutations to occur, wherein said Salmonella bacterium according to claim 7 is non-selectable for a known Salmonella characteristic;
   (b) culturing said bacterium in a cell culture medium which is selective for the growth of cells having said known Salmonella characteristic; and
   (c) identifying the number of said bacterium that grow in the cell culture medium of (b), wherein the number of bacterium that grow in the cell culture medium of (b) is directly proportional to the ability of said mutagen to induce cytosine to adenine transition mutations.

9. A kit comprising a bacterium selected from the group consisting of the bacterium of claim 1, the bacterium of claim 3, the bacterium of claim 5 and the bacterium of claim 7.

* * * * *